US010023886B2

(12) United States Patent
Schurmann et al.

(10) Patent No.: US 10,023,886 B2
(45) Date of Patent: Jul. 17, 2018

(54) (R)-SELECTIVE AMINATION

(71) Applicant: DPX Holdings B.V., Amsterdam (NL)

(72) Inventors: Martin Schurmann, Echt (NL); Wijnand Peter Helena Peeters, Echt (NL); Natascha Hubertina Johannes Smeets, Echt (NL); Helmut Schwab, Graz (AT); Kerstin Steiner, Graz (AT); Kateryna Mykolayivna Lypetska, Graz (AT); Gernot Strohmeier, Hengsberg (AT)

(73) Assignee: Patheon Holdings I B.V., Amsterdam (NL)

( * ) Notice: Subject to any disclaimer, the term of this patent is extended or adjusted under 35 U.S.C. 154(b) by 0 days.

(21) Appl. No.: 14/885,622

(22) Filed: Oct. 16, 2015

(65) Prior Publication Data
US 2016/0032335 A1    Feb. 4, 2016

Related U.S. Application Data

(63) Continuation of application No. 13/810,004, filed as application No. PCT/EP2011/062056 on Jul. 14, 2011, now abandoned.

(30) Foreign Application Priority Data

Jul. 14, 2010  (EP) .................................. 10169573

(51) Int. Cl.
C12P 13/00    (2006.01)
C12N 9/10    (2006.01)

(52) U.S. Cl.
CPC .......... C12P 13/001 (2013.01); C12N 9/1096 (2013.01); *C12Y 206/01* (2013.01)

(58) Field of Classification Search
CPC .... C12P 13/001; C12P 41/006; C12N 9/1096; C12N 9/90
USPC ............ 435/108, 128, 193, 16, 252.1, 254.1
See application file for complete search history.

(56) References Cited

U.S. PATENT DOCUMENTS

| 6,413,752 B1 | 7/2002 | Takashima et al. |
| 7,169,592 B2 | 1/2007 | Yamada et al. |
| 2002/0192786 A1 | 12/2002 | Yamada et al. |

FOREIGN PATENT DOCUMENTS

| EP | 987332 A1 | 3/2000 |
| EP | 1038953 B1 | 9/2004 |
| EP | 1513946 A1 | 3/2005 |
| EP | 1897956 A1 | 3/2008 |
| EP | 0987332 B1 | 8/2009 |
| JP | 2000-342276 | 12/2000 |
| JP | 4213771 B2 | 11/2008 |
| WO | 03106691 A1 | 12/2003 |
| WO | 2008000632 A1 | 1/2008 |
| WO | 2011026556 A1 | 3/2011 |
| WO | 2012007548 A1 | 1/2012 |

OTHER PUBLICATIONS

Gawley et al. J. org. chem. 2006, 71(6) pp. 2411-2416.*
Balzer, et al. "KorB protein of promiscuous plasmid RP4 recognizes inverted sequence repetitions in regions essential for conjugative plasmid transfer" Nucleic Acids Research; 1992; vol. 20; No. 8; pp. 1851-1858.
Altschul, et al. "Basic Local Alignment Search Tool" Journal Mol. Biol.; 1990; vol. 215; pp. 403-410.
Larkin, et al. "Clustal W and Clustal X version 2.0" Bioinformatics; 2007; vol. 23; No. 21; pp. 2947-2948.
Bradford "A Rapid and Sensitive Method for the Quantitation of Microgram Quantities of Protein Utilizing the Principle of Protein-Dye Binding" Analytical Biochemistry; 1976; vol. 72; pp. 248-254.
Bloom, et al. "In the light of directed evolution: Pathways of adaptive protein evolution" PNAS; Jun. 16, 2009; vol. 106; Suppln. 1; pp. 9995-10000.

(Continued)

*Primary Examiner* — Tekchand Saidha
*Assistant Examiner* — Mohammad Y Meah
(74) *Attorney, Agent, or Firm* — Pierce Atwood LLP; Raymond G. Arner

(57) ABSTRACT

The present invention relates to a method for the enzymatic synthesis of enantiomerically enriched (R)-amines of general formula [1][c]

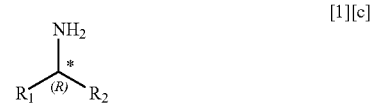

from the corresponding ketones of the general formula [1][a]

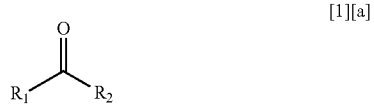

by using novel transaminases.
These novel transaminases are selected from two different groups: either from a group of some 20 proteins with sequences as specified herein, or from a group of proteins having transaminase activity and isolated from a microorganism selected from the group of organisms consisting of *Rahnella aquatilis, Ochrobactrum anthropi, Ochrobactrum tritici, Sinorhizobium morelense, Curtobacterium pusiffium, Paecilomyces lilacinus, Microbacterium ginsengisoli, Microbacterium trichothecenolyticum, Pseudomonas citronellolis, Yersinia kristensenii, Achromobacter spanius, Achromobacter insolitus, Mycobacterium fortuitum, Mycobacterium frederiksbergense, Mycobacterium sacrum, Mycobacterium fluoranthenivorans, Burkhoideria sp., Burkhoideria tropica, Cosmospora episphaeria,* and *Fusarium oxysporum*.

12 Claims, No Drawings

(56) References Cited

OTHER PUBLICATIONS

European Office Action for European Patent Application No. 11733837.6 dated Jan. 28, 2015 (6 pages).
Chinese Office Action for Chinese Patent Application No. 201180034658.9 dated May 13, 2014 (6 pages).
European Office Action for European Patent Application No. 11733837.6 dated Nov. 29, 2013 (5 pages).
Shin, et al. "Purification, characterization, and molecular cloning of a novel amine:pyruvate transaminase from Vibrio fluvialis JS17" Applied Microbiology and Biotechnology; Jun. 2003; vol. 61, Issue 5-6; pp. 463-471.
Constable, et al. "Key green chemistry research areas—a perspective from pharmaceutical manufacturers" Green Chemistry; 2007; vol. 9; pp. 411-420.
Muzny et al., "D-Amino-Acid Transaminase", Achromobacter Piechaudii ATCC, XP-000002656962, last modified Mar. 8, 2011, 3 pages.
Iwasaki et al., "Microbial Synthesis of Chiral Amines by (R)-specific transmination with Arthrobacter sp. KNK168", Applied Microbiology and Biotechnology, 2006, vol. 69, pp. 499-505.
Iwasaki et al., "Microbial synthesis of (R)- and (S)-3,4-dimethoxyamphetamines through stereoselcti ve transami nation", Biotechnology Letters, vol. 25, 2003, pp. 1843-1846.
Savile et al: "Biocatalytic asymmetric synthesis of chiral amines from ketones applied to sitagliptin manufacture", Science, vol. 329, Jun. 17, 2010, pp. 305-309.
Koszelewski et al: "Omega-transami nases for the synthesis of non-racemic alpha-chiral primary amines", Trends in Biotechnology, vol. 28, Jun. 2010 (Jun. 2010), pp. 324-332.
Hohne et al: "Rational assignment of key motifs for function guides in silico enzyme identification", Nature Chemical Biology, vol. 6, Sep. 2010 (Sep. 2010), pp. 807-813.
Lucas et al: "Branched-chain amino acid aminotransferase", XP000002656963, Database accession No. E8XMM8, Apr. 2011 (Apr. 2011).
Hoehne et al: "Sequence Listing", Sequence Listing of WO 2011/026556, 1-17, (published without Sequence Listing), Mar. 10, 2011 (Mar. 10, 2011), XP000002656964, Retrieved from the Internet: URL:www.wipo.int/pctdb/en/search-struct.jsp [retrieved on Aug. 17, 2011].
International Search Report and Written Opinion for PCT/EP2011/062056 dated Aug. 29, 2011.
UNIPROT D4X4Z8, last modified Jun. 15, 2010, accessed at http://www.uniprot.org/uniprot/D4X4Z8.
UNIPROT E8XMM8, dated Apr. 5, 2011, accessed at http://www.uniprot.org/uniprot/E8XMM8.txt?version=1.
Birren et al., "conserved hypothetical protein [Aspergillus terreus NIH2624]," Genbank Accession XP_001209325.1, dated Mar. 31, 2008.
Badger, JH. Aminotransferase, class IV (Hyphomonas neptunium ATCC 15444). GenBank: ABI75539.1 (2 pages).
Chinese Office Action for Chinese Patent Application No. CN201180034658.9, dated Apr. 8, 2015 (14 pages).
Rejection Decision for Chinese Patent Application No. CN201180034658.9, dated Nov. 3, 2015 (10 pages).
Copeland, A. Branched-chain amino acid: 2-keto-4-methylthiobutyrate aminotransferase [Burkholderia sp. 383]. GenBank: ABB05831.1 (1 page).
Copeland, A. Branched-chain amino acid: 2-keto-4-methylthiobutyrate aminotransferase [Burkholderia cenocepacia HI2424] GenBank: ABK12047.1 (1 page).
Copeland, A. Branched-chain amino acid: 2-keto-4-methylthiobutyrate aminotransferase [Mycobacterium vanbaalenii PYR-1]. GenBank: ABM15291.1. (1 page).

Communication pursuant to Article 94(3) EPC, in European Application No. 11 733 837.6-1501, dated Jun. 23, 2014 (6 pages).
Notice of Reasons for Rejection in Japanese Patent Application No. JP2013-5191031 (11 pages).
Keneko, T. Branched-chain amino acid aminotransferase [Mesorhizobium loti MAFF303099]. GenBank: BAB54591.1. (1 page).
Monteiro-Vitorello, C. Branched-chain amino acid aminotransferase [Leifsonia xyli subsp. xyli str. CTCB07]. GenBank: AAT89149.1 (1 page).
International Preliminary Report on Patentability, PCT/EP2011/062056, dated Jan. 24, 2013. (9 pages).
Pel, HJ. Unnamed protein product [Aspergillus niger]. GenBank: CAK38950.1 (2 pages).
van den Berg, M.A. Pc22g00160 [Penicillium chrysogenum Wisconsin 54-1255]. GenBank: CAP97304.1 (1 page).
Final Notice of Reasons for Rejection, Japanese Patent Application No. P2013-519103, 9 pages.
Unnamed protein product [Aspergillus niger], GenBank: CAK38950.1, 3 pages.
Branched-chain amino acid aminotransferase [Leifsonia xyli subsp. xyli str. CTCB07]GenBank: AAT89149.1, 3 pages.
Branched chain amino acid: 2-keto-4-methylthiobutyrate aminotransferase [Burkholderia lata] GenBank: ABB05831.1, 3 pages.
Aminotransferase, class IV [Hyphomonas neptunium ATCC 15444] GenBank: ABI75539.1, 2 pages.
Branched chain amino acid: 2-keto-4-methylthiobutyrate aminotransferase [Burkholderia cenocepacia HI2424] GenBank: ABK12047.1, 3 pages.
Branched chain amino acid: 2-keto-4-methylthiobutyrate aminotransferase [Mycobacterium vanbaalenii PYR-1] GenBank: ABM15291.1, 2 pages.
Branched-chain amino acid aminotransferase [Pectobacterium carotovorum subsp. carotovorum PC1] GenBank: ACT15045.1, 2 pages.
Branched-chain amino acid aminotransferase (plasmid) [Mesorhizobium loti MAFF303099] GenBank: BAB54591.1, 2 pages.
Pc22g00160 [Penicillium rubens Wisconsin 54-1255] GenBank: CAP97304.1, 2 pages.
Putative D-amino-acid transaminase [Achromobacter piechaudii ATCC 43553] GenBank: EFF78320.1, 3 pages.
Gawley, Robert E.; "Do the Terms "%ee" and "%de" Make Sense as Expressions of Stereoisomer Commposition or Stereoselectivity"; NIH Public Access Author Manuscript; J. Org. Chem.; Mar. 17, 2006; vol. 71; No. 6; pp. 2411-2416.
The Third Office Action from corresponding Chinese Patent Application No. 201180034658.9 dated Aug. 1, 2016, 8 pages.
The Fourth Office Action from corresponding Chinese Patent Application No. 201180034658.9 dated Apr. 10, 2017, 9 pages.
European Communication from corresponding European Patent Application No. 11733837.6 dated Jun. 23, 2014.
European Communication from corresponding European Patent Application No. 11733837.6 dated Mar. 23, 2016, 5 pages.
Lyskowski, A., et al., "Crystal Structure of an (R)-Selective v-Transaminase from Aspergillus terreus," PLOS One 9(1): e87350, Jan. 2014.
Chinese Notice of Registration and Notice of Grant of a Patent Right from corresponding Chinese Patent Application No. 201180034658.9 dated Oct. 11, 2017, 5 pages.
Lucas et al., "Branched-chain Amino Acid Aminotransferase," XP000002656963, last modified Jul. 27, 2011.

* cited by examiner

(R)-SELECTIVE AMINATION

RELATED APPLICATIONS

This application is a continuation of U.S. application Ser. No. 13/810,004, filed Mar. 12, 2014, now abandoned, which is the U.S. national stage application of International Application No. PCT/EP2011/062056, filed Jul. 14, 2011, which claims priority to EP 10169573.2, filed Jul. 14, 2010, the entire contents of each of which are hereby incorporated by reference.

The present invention relates to a method for the (R)-selective amination of ketones and to enzymes for use in this method.

A considerable number of pharmaceutically active compounds (existing and under development) contain a chiral amine functionality which can not be directly derived synthetically from natural amino acids. According to pharmaceutical manufacturers, asymmetric synthesis of amines from ketones is one of the most desirable reactions for the future (Constable et al., Green Chem. 2007, 9, 411). Furthermore, it is a goal of the pharmaceutical manufacturers to rely as much as possible on "green" routes in the synthesis of their pharmaceutically active compounds. Biocatalytic conversions are therefore preferred.

An attractive route for biocatalytic production of chiral amines is stereoselective transamination starting from a ketone and an amine donor, according to reaction [1]:

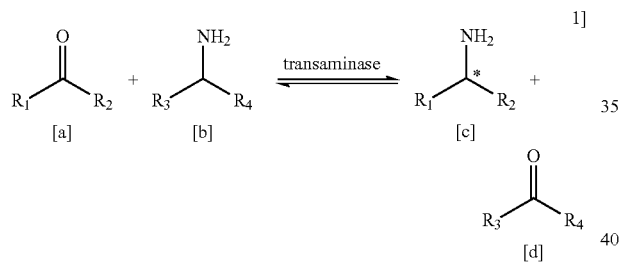

The required stereoselective enzymes (interchangeably called transaminases, aminotransferases or aminopherases) have been reported for instance the (S)-selective ω-transaminase from *Vibrio fluvialis* (Shin et al., Appl. Microbiol. Biotechnol. 2003, 61, 463), although (S)-selective enzymes are by far more abundant than (R)-selective enzymes.

Stereoselective transaminases have for example been described in the European patent publications EP1038953 and EP987332.

EP1038953 relates to a DNA encoding a transaminase capable of synthesizing optically active (R)-α-methylbenzylamine in the presence of sec-butylamine.

EP987332 relates in particular to a transaminase from a *Mycobacterium aurum* species which can catalyze the stereoselective transamination of acetophenone and sec-butylamine to an enantiomerically enriched (R)-α-methylbenzylamine and 2-butanone. The same transaminase was also used for the racemic resolution or (RS)-α-methylbenzylamine to obtain enantiomerically enriched (S)-α-methylbenzylamine as well as the synthesis of enantiomerically enriched D-alanine and D-serine.

U.S. Pat. No. 7,169,592 relates to a DNA from an *Arthrobacter* species encoding a recombinant transaminase, which can catalyze the (R)-stereoselective transamination of several ketones in the presence of an amino donor to produce enantiomerically enriched (R)-amines.

There is a need for further stereoselective transaminases in order to be able to apply stereoselective transamination reactions to a wider spectrum of compounds.

The present invention relates to a method for the enzymatic synthesis of enantiomerically enriched (R)-amines of general formula [1][c] from the corresponding ketones of the general formula [1][a] by using novel transaminases.

These novel transaminases are selected from the group consisting of
  a) a protein having at least 90% identity to the amino acid sequence of SEQ ID No. 1;
  b) a protein having at least 90% identity to the amino acid sequence of SEQ ID No. 3;
  c) a protein having at least 90% identity to the amino acid sequence of SEQ ID No. 5;
  d) a protein having at least 90% identity to the amino acid sequence of SEQ ID No. 7;
  e) a protein having at least 90% identity to the amino acid sequence of SEQ ID No. 9;
  f) a protein having at least 90% identity to the amino acid sequence of SEQ ID No. 11;
  g) a protein having at least 90% identity to the amino acid sequence of SEQ ID No. 13;
  h) a protein having at least 90% identity to the amino acid sequence of SEQ ID No. 15;
  i) a protein having at least 90% identity to the amino acid sequence of SEQ ID No. 17;
  j) a protein having at least 90% identity to the amino acid sequence of SEQ ID No. 19;
  k) a protein having at least 90% identity to the amino acid sequence of SEQ ID No. 21;
  l) a protein having at least 90% identity to the amino acid sequence of SEQ ID No. 23;
  m) a protein having at least 90% identity to the amino acid sequence of SEQ ID No. 25;
  n) a protein having at least 90% identity to the amino acid sequence of SEQ ID No. 30;
  o) a protein having at least 90% identity to the amino acid sequence of SEQ ID No. 33;
  p) a protein having at least 90% identity to the amino acid sequence of SEQ ID No. 35;
  q) a protein having at least 90% identity to the amino acid sequence of SEQ ID No. 38;
  r) a protein having at least 90% identity to the amino acid sequence of SEQ ID No. 40;
  s) a protein having at least 90% identity to the amino acid sequence of SEQ ID No. 43;
  t) a protein having at least 90% identity to the amino acid sequence of SEQ ID No. 46 and
  u) a protein having transaminase activity and isolated from a microorganism selected from the group of organisms consisting of *Rahnella aquatilis, Ochrobactrum anthropi, Ochrobactrum tritici, Sinorhizobium morelense, Curtobacterium pusillium, Paecilomyces lilacinus, Microbacterium ginsengisoli, Microbacterium trichothecenolyticum, Pseudomonas citronellolis, Yersinia kristensenii, Achromobacter spanius, Achromobacter insolitus, Mycobacterium fortuitum, Mycobacterium frederiksbergense, Mycobacterium sacrum, Mycobacterium fluoranthenivorans, Burkholderia* sp., *Burkholderia tropica, Cosmospora episphaeria,* and *Fusarium oxysporum.*

According to the present invention it has been found, in sequence alignment studies using ClustalW2 multiple sequence alignment at default settings (Larkin et al., Bioinformatics 2007, 23, 2947, available at URL: www.ebi. ac.ukJTools/clustaiw2), that the transaminases of SEQ ID No. 1, 3, 5, 7, 9, 11, 13, 15, 17, 19, 21, 23, and 25 according to this invention vary over a broad range of identity percentage with the wild-type amino acid sequence of SEQ ID No. 1 of the transaminase. Even at an identity percentage of about 30% to SEQ ID No. 1 still very suitable transaminases are being found according to the present invention.

The inventors have found, however, that the transaminases as can be used in the present invention (and the mutants derived there from) all have in common, that they have at least 37 conserved amino acids, namely A32, A44, D50, G52, D57. Y60, V65, G68, F71, L73, R79, V106, V116, R122, G123, P145, P177, K180, N181, W183, D185, E213, G216, N218, P230, L235, G237, R240, V243, E269, A276, G277, G278, P281, G296, W307, and Y321, when being compared to the wild-type amino acid sequence of SEQ ID No. 1 at the positions corresponding to the above positions in the amino acid sequence of SEQ ID No. 1.

Amino acid residues of wild-type or mutated protein sequences corresponding to positions of the amino acid residues in the wild-type amino acid sequence of the transaminase of SEQ ID No. 1 can be identified by performing ClustalW2 multiple sequence alignments at default settings. Amino acid residues, which are placed in the same column as an amino acid residue of the transaminase sequence as given in SEQ ID No. 1 in such alignments, are defined to be positions corresponding to this respective amino acid residue of the transaminase sequence of SEQ ID No. 1.

Samples of each of the microorganisms *Rahnella aquatilis, Ochrobactrum anthropi, Ochrobactrum tritici, Sinorhizobium morelense, Curtobacterium pusillium, Paecilomyces lilacinus, Microbacterium ginsengisoli, Microbacterium trichothecenolyticum, Pseudomonas citronellolis, Yersinia kristensenii, Achromobacter spanius, Achromobacter insolitus, Mycobacterium fortuitum, Mycobacterium frederiksbergense, Mycobacterium sacrum, Mycobacterium fluoranthenivorans, Burkholderia* sp., *Burkholderia tropica, Cosmospora episphaeria,* and *Fusarium oxysporum* were deposited at the German Collection of Microorganisms and Cell Cultures (DSMZ) at Braunschweig, Germany on Jul. 13, 2010.

In the above chemical structures [1][a] and [1][c] $R_1$ and $R_2$ are different and can be independently linear or branched aliphatic, hetero-aliphatic, aromatic, hetero-aromatic or form a cyclic structure.

More in particular, $R_1$ and $R_2$ are different and $R_1$ and $R_2$ independently contain 1 to 30 carbon atoms and $R_1$ and $R_2$ are independently substituted or unsubstituted aliphatic; substituted or unsubstituted branched aliphatic; substituted or unsubstituted cyclic aliphatic; substituted or unsubstituted hetercyclic aliphatic, containing at least one oxygen, sulfur or nitrogen atom; substituted or unsubstituted aromatic; substituted or unsubstituted hetero-aromatic containing at least one sulfur, oxygen or nitrogen atom; or together form a substituted or unsubstituted cyclic structure or heterocyclic structure, containing at least one oxygen, sulfur or nitrogen atom; wherein the substituents are selected from, but not limited to, the group consisting of a halogen atom, an alkyl group having 1 to 6 carbon atoms, hydroxyl group, methoxy group, monofluoromethyl, difluoromethyl and trifluoromethyl group.

Preferably the final concentration of the enantiomerically enriched (R)-amine product lies between 1 and 50 weight % of the reaction mixture. Most preferably final concentration of the enantiomerically enriched (R)-amine product lies between 5 and 35 weight % of the reaction mixture.

A process according to this invention can be carried out in a aqueous reaction mixture with all reactions dissolved or in slurries with some of the reactants at least partially dissolved and some of the reactions at least partially as solid material.

The use of a non water-miscible solvent such as an organic solvent forming a second liquid phase next to the buffered aqueous phase containing a transaminase can be advantageous in transaminase reactions over purely aqueous or aqueous slurry reactions, because the organic solvent can act as a reservoir for poorly water-soluble ketones and amino donors. It can increase the mass transfer rate for the dissolution of poorly water-soluble ketones or amino donors into the transaminase containing aqueous phase compared to slurry reactions (solid-aqueous). Further it can reduce potential substrate or product inhibition by extractive removal of these potential inhibitors. Furthermore such extractive removal of at least one of the transaminase reaction products can pull the equilibrium of the transaminase reaction in the aqueous phase to the products side, thereby improving the yield and/or the efficiency of the transaminase catalysed reaction.

A process according to this invention can be carried out in a reaction mixture comprising an aqueous phase and second organic phase. In case a reaction mixture comprising an aqueous phase and second organic phase is used, the reaction mixture preferably comprises an aqueous phase and second organic phase and the volumetric ratio of water:organic phase is between 100 and 0.01. More preferably the reaction mixture comprises an aqueous phase and second organic phase and the volumetric ratio of water:organic phase is between 20 and 0.1. Most preferably the reaction mixture comprises an aqueous phase and second organic phase and the volumetric ratio of water:organic phase is between 20 and 1.

Suitable organic solvents can for instance be selected from the group of, but are not restricted to cyclohexanone, dichloromethane, pentane, heptane, MTBE (methyl-tert-butylether), toluene, 2-methyl-tetrahydrofurane, butylacetate and ethylacetate.

The transaminase a) through m) above according to the present invention have been identified in database searches in public nucleotide and polypeptide databases like EMBL/GenBank/DDBJ, Swiss-Prot/UniProtKB (released on Jun. 15, 2010), RefSeq or Non-redundant via the EMBL-EBI (URL: www.ebi.ac.uk) or NCBI (URL: www.ncbi.nlm.nih.gov) servers annotated as "hypothetical protein" with highest similarity to branched chain L-amino acid aminotransferases or 4-amino-4-deoxychorismate lyases (EC4.1.3.38) belonging to Pyridoxal 5'-Phosphate Dependent Enzymes class IV (PLPDE_IV) superfamily. Functional expression and activity have so far not been reported to support the annotation.

Surprisingly, it has been found that transaminase a) through m) are in fact (R)-selective ω-transaminases instead of (S)-selective amino acid aminotransferases as will be described below. Further the transaminases a) through m) differ in substrate spectrum than the (R)-transaminases described in EP1038953, EP987332 and U.S. Pat. No. 7,169,592.

The transaminases a) through t) above according to the present invention have been characterized by their activity and enantioselectivity in one or more of the following ω-transaminase conversions:

(i) Racemic Resolution of (RS)-α-Methylbenzylamine.

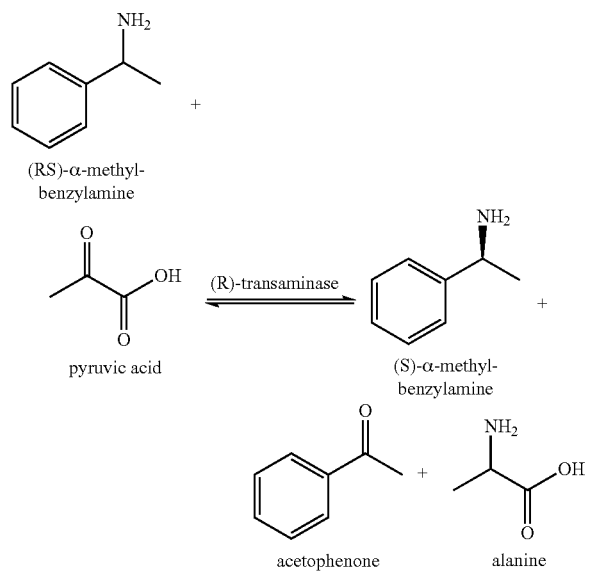

The enantioselectivity of enzymes in general and transaminases specifically can be determined in a racemic resolution of a racemic mixture of a substrate comprising a chiral center. According to this invention an (R)-selective transaminase is an enzyme which preferentially transaminates (R)-α-methylbenzylamine (MBA) from racemic MBA in the presence of a ketone substrate such as pyruvic acid. An (R)-transaminase according to this invention is an enzyme which preferentially converts the (R)-over (S)-enantiomer of α-methylbenzylamine in the presence of pyruvic acid resulting in the enrichment of the remaining (S)-enantiomer with an enantiomeric excess (e.e.) of at least 10%. Preferably the resulting e.e. of (S)-MBA is at least 50%. More preferably the e.e. is at least 60%. Even more preferably the e.e. is at least 70%. Even more preferably the e.e. is at least 80%. Even more preferably the e.e. is at least 90%. Even more preferably the e.e. is at least 95%. Even more preferably the e.e. is at least 96%. Even more preferably the e.e. is at least 97%. Even more preferably the e.e. is at least 98%. Most preferably the e.e. is at least 99%.

Typically 80 mM of racemic α-methylbenzylamine (MBA) are reacted with 40 mM sodium pyruvate in 100 mM potassium phosphate (KP$_i$) buffer pH 7.0 containing 0.1 mM pyridoxal 5'-phosphate (PLP) at 28° C. for 20 h in the presence of a transaminase. The concentrations and enantiomeric excesses of (R)- and/or (S)-MBA can for instance be determined by high performance liquid chromatography (HPLC) or gas chromatography (GC) with suitable chiral column materials. The formulation of the (R)-transaminase is not critical; it can be added as (partially) purified enzyme, cell-free extract (CFE) or crude cell extract; liquid, powder or immobilized form; permeabilised cells, whole cells or culture broth containing cells comprising the transaminase or in any other form.

(ii) Activity and Selectivity on the Pure Enantiomers of α-Methylbenzylamine.

The enantioselectivity of an enzyme is also characterized by its specific activities towards the individual enantiomers of a specific substrate. These can be determined in separate activity assays with the individual enantiopure forms of the substrate. According to this invention the specific transaminase activities towards the two enantiomers of α-methylbenzylamine (MBA) are a measure for the (R)-selectivity of a transaminase. In the context of this invention the ratio of the specific activities on (R)-MBA over the specific activities on (S)-MBA is defined as the Transaminase Enantioselectivity Value (TEV). An (R)-selective transaminase is defined as a transaminase with a TEV value of >1. A good (R)-selectivity of a transaminase is defined as a specific activity ratio on (R)-over (S)-MBA of TEV 10. A high (R)-selectivity of a transaminase is defined as a specific activity ratio on (R)-over (S)-MBA of TEV≥100.

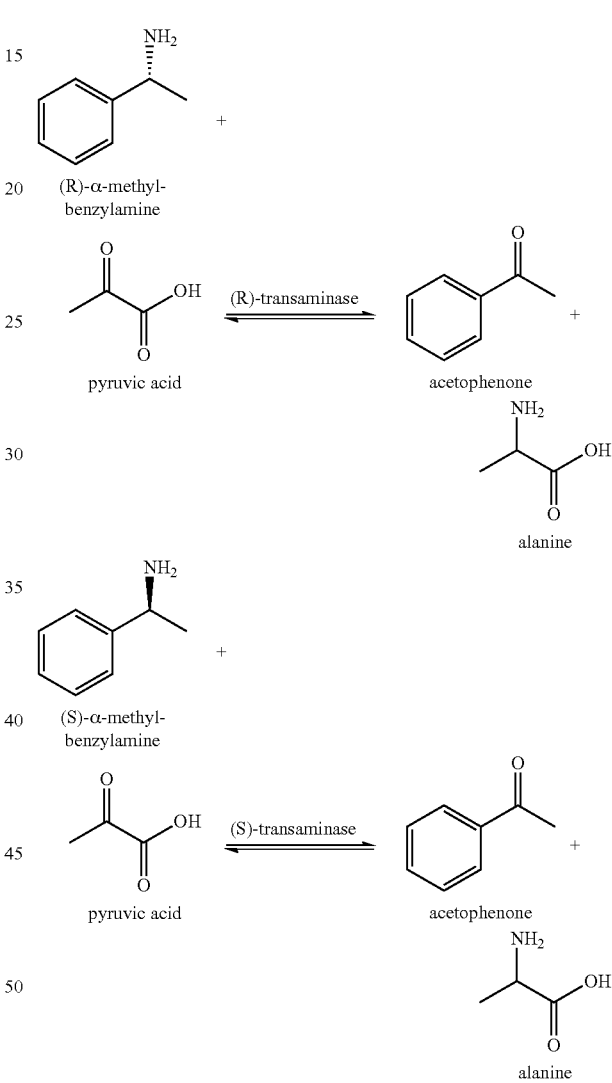

The specific transaminase activities on (R)- and (S)-MBA are separately determined using a spectrophotometric assay. In a final reaction volume of 1 ml 50 µl of a suitable dilution of a transaminase in liquid form is mixed in a cuvette with 12.5 mM (R)- or (S)-MBA and 5 mM sodium pyruvate in the presence of 50 mM KP$_i$ buffer pH 7.5 containing 0.1 mM PLP. The reactions are started by addition of 10 µl of 0.5 M sodium pyruvate (in 50 mM KR buffer pH 7.5, 0.1 mM PLP) to the other assay components, after pre-incubation at 30° C. for 5 min. After addition of sodium pyruvate the absorption at 300 nm is recorded and the transaminase activity in the samples is calculated according to the law of Lambert-Beer using the molar extinction coefficient for acetophenone at 300 nm of ε=0.28 cm$^2$/μmol. One unit (U) of transaminase activity is defined as 1 μmol of acetophenone formed from 12.5 mM (R)-MBA or (S)-MBA and 5 mM sodium pyruvate at 30° C. in 50 mM KP$_i$ buffer pH 7.5 containing 0.1 mM PLP per minute. The specific transaminase activities of the CFEs (U/mg total CFE protein) are calculated by dividing the volumetric activity values (U/ml CFE) by the total protein concentration in the liquid transaminase sample. The Transaminase Enantioselectivity Value (TEV) is calculated by dividing the volumetric or specific activity on (R)-MBA by the volumetric or specific activity, respectively, on (S)-MBA.

Preferably the (R)-transaminase has a TEV of at least 1, more preferably the (R)-transaminase has a TEV of at least 10, even more preferably the (R)-transaminase has a TEV of at least 100.

(iii) Synthesis of Enantiomerically Enriched (R)-Amines from the Corresponding Ketones and Suitable Amino Donors Such as Benzylamine or α-Methylbenzylamine.

The typical desired outcome of a reaction catalysed by an (R)-selective transaminase is the formation of an enantiomerically enriched (R)-amine according to formula 1 [c] from an amino donor and a ketone substrate. Suitable amino donors for (R)-selective transaminase reactions comprise for instance racemic or (R)-MBA, racemic or (R)-1-aminoindan, racemic or (R)-1-aminotetralin, racemic or D-alanine, isopropylamine, benzylamine, racemic or (R)-sec-butylamine (2-aminobutane), β-alanine or racemic or D-3-aminobutyric acid.

Generally, with a particular transaminase, certain amino donors are preferred. Surprisingly, we have found that with the transaminase of SEQ ID No. 1, SEQ ID No. 3, SEQ ID No. 7, SEQ ID No. 9, SEQ ID No. 13, SEQ ID No. 15, SEQ ID No. 17, SEQ ID No. 21, SEQ NO ID 23, and SEQ ID No. 43 the preferred amino donors are racemic or (R)-MBA or racemic or (R)-sec-butylamine.

Typically 70 mM of amino donor is reacted with 70 mM of ketone substrate in the presence of an (R)-transaminase in an aqueous reaction mixture buffered with 100 mM potassium phosphate (KR) at pH 7.5 at 28° C. Optionally water miscible or immiscible solvents can be used to solubilise amino donor or ketone substrate. An (R)-selective transaminase according to this invention will exhibit at least low conversion of at least 0.5% to the desired enantiomerically enriched (R)-amine starting from equimolar amounts of amino donor and ketone substrate with the enantiomerically enriched (R)-amine having an enantiomeric excess of at least 50% after over night reaction at 28° C. The form of the (R)-transaminase is not critical; it can be added as (partially) purified enzyme, cell-free extract or crude cell extract; liquid, powder or immobilized form; permeabilised cells, whole cells or culture broth containing cells comprising the transaminase or in any other form.

It is known to the person skilled in the art that transaminase reactions are reversible reactions and the degree of conversion is influenced by the equilibrium of the specific substrates and products. Further it is known to the person skilled in the art that the degree of substrate conversion at equimolar amino donor and ketone substrate concentrations can be increased by for instance in situ product removal by evaporation of one of the reaction products or using resins, or addition of enzymes which further convert one of the reaction products such as pyruvate decarboxylase or lactate dehydrogenase. Further it is known that the degree of conversion of ketone substrate 1[a] to amine product 1[c] can be increased by an excess of amino donor 1[b].

Preferably the produced enantiomerically enriched (R)-amine has an e.e. of at least 50%. More preferably the e.e. is at least 60%. Even more preferably the e.e. is at least 70%. Even more preferably the e.e. is at least 80%. Even more preferably the e.e. is at least 90%. Even more preferably the e.e. is at least 95%. Even more preferably the e.e. is at least 96%. Even more preferably the e.e. is at least 97%. Even more preferably the e.e. is at least 98%. Even more preferably the e.e. is at least 99%. Most preferably the produced enantiomerically enriched (R)-amine has an e.e. of larger than 99%.

In the present application "a protein having at least 90% sequence identity to the amino acid sequence of (a reference sequence)" means that such protein is a homologue of the respective reference sequence having an amino acid sequence, which is for at least 90% identical to the amino acid sequence of the reference sequence as determined in sequence alignments performed with sequence alignment tools such as BLASTP (URL: blast.ncbi.nlm.nih.gov/Blast), ClustalW (URL: www.ebi.ac.uk/Tools/clustalw2) or Align Plus 5 (Scientific & Educational Software, Cary, N.C., USA).

The term "homologue" is used herein in particular for polynucleotides or polypeptides having a sequence identity of at least 60%, preferably at least 65%, more preferably at least 70%, more preferably at least 75%, more preferably at least 80%, in particular at least 85%, more in particular at least 90%, at least 91%, at least 92%, at least 93%, at least 94%, at least 95%, at least 96%, at least 97%, at least 98% or at least 99%. The term homologue is also meant to include nucleic acid sequences (polynucleotide sequences) which differ from another nucleic acid sequence due to the degeneracy of the genetic code and encode the same polypeptide sequence.

Sequence identity or similarity is herein defined as a relationship between two or more polypeptide sequences or two or more nucleic acid sequences, as determined by comparing the sequences. Usually, sequence identities or similarities are compared over the whole length of the sequences, but may however also be compared only for a part of the sequences aligning with each other. In the art, "identity" or "similarity" also means the degree of sequence relatedness between polypeptide sequences or nucleic acid sequences, as the case may be, as determined by the match between such sequences. Preferred methods to determine identity or similarity are designed to give the largest match between the sequences tested. In context of this invention a preferred computer program method to determine identity and similarity between two sequences includes BLASTP and BLASTN (Altschul, S. F. et al., *J. Mol. Biol.* 1990, 215, 403-410, publicly available from NCBI and other sources (BLAST Manual, Altschul, S. et al., NCBI NLM NIH, Bethesda, Md., USA). Preferred parameters for polypeptide sequence comparison using BLASTP are gap open 10.0, gap extend 0.5, Blosum 62 matrix. Preferred parameters for nucleic acid sequence comparison using BLASTN are gap open 10.0, gap extend 0.5, DNA full matrix (DNA identity matrix).

The transaminase according to this invention may be used in any form. For example, the transaminase may be used—for example in the form of a dispersion, a solution or in immobilized form—as crude enzyme, as a commercially available enzyme, as an enzyme further purified from a commercially available preparation, as an enzyme obtained from its source by a combination of known purification methods, in whole (optionally permeabilized and/or immobilized) cells that naturally or through genetic modification possess the required tranasminase activity, or in a lysate of cells with such activity.

A cell comprising a transaminase in a method of the invention can be constructed using molecular biological techniques, which are known in the art per se. For instance, if a transaminase is to be produced in a heterologous system, such techniques can be used to provide a vector which comprises a gene encoding a transaminase.

A gene encoding a polypeptide with transaminase activity can be adapted to the preferred codon usage of the host cell used for the production of the polypeptide to improve expression level of the polypeptide. A suitable method to achieve such an adaptation is for instance Codon-Pair-Optimization as described in WO08000632.

A vector comprising such a gene can comprise one or more regulatory elements, e.g. one or more promoters, which may be operably linked to a gene encoding a transaminase. Examples of such vectors comprise plasmids like pBAD/Myc-HisC, pBAD-DEST49, pET-DEST42 (all Invitrogen, Carlsbad, Calif., USA), plasmids of the pET series for instance pET-26b(+) (Novagen, Nottingham, UK) or pMS470Δ8 (Balzer et al., *Nucleic Acids Research*, 1992, 20 (8): 1851-1858).

As used herein, the term "operably linked" refers to a linkage of polynucleotide elements (or coding sequences or nucleic acid sequence) in a functional relationship. A nucleic acid sequence is "operably linked" when it is placed into a functional relationship with another nucleic acid sequence. For instance, a promoter or enhancer is operably linked to a coding sequence if it affects the transcription of the coding sequence.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skilled in the art to act directly or indirectly to regulate the amount of transcription from the promoter. A "constitutive" promoter is a promoter that is active under most environmental and developmental conditions. An "inducible" promoter is a promoter that is active under environmental or developmental regulation. The term "homologous" when used to indicate the relation between a given (recombinant) nucleic acid or polypeptide molecule and a given host organism or host cell, is understood to mean that in nature the nucleic acid or polypeptide molecule is produced by a host cell or organisms of the same species, preferably of the same variety or strain.

The promoter that could be used to achieve the expression of the nucleotide sequences coding for an enzyme for use in a method of the invention, in particular a transaminase, such as described herein above may be native to the nucleotide sequence coding for the enzyme to be expressed, or may be heterologous to the nucleotide sequence (coding sequence) to which it is operably linked. Preferably, the promoter is homologous, i.e. endogenous to the host cell.

If a heterologous promoter (to the nucleotide sequence encoding for the enzyme of interest) is used, the heterologous promoter is preferably capable of producing a higher steady state level of the transcript comprising the coding sequence (or is capable of producing more transcript molecules, i.e. mRNA molecules, per unit of time) than is the promoter that is native to the coding sequence. Suitable promoters in this context include both constitutive and inducible natural promoters as well as engineered promoters, which are well known to the person skilled in the art.

A "strong constitutive promoter" is one which causes mRNAs to be initiated at high frequency compared to a native host cell.

Examples of such strong constitutive promoters in Gram-positive micro-organisms include SP01-26, SP01-15, veg, pyc (pyruvate carboxylase promoter), and amyE.

Examples of inducible promoters in Gram-positive microorganisms include, the IPTG inducible Pspac promoter, the xylose inducible PxyIA promoter.

Examples of constitutive and inducible promoters in Gram-negative microorganisms include, but are not limited to tac, tet, trp-tet, lpp, lac, lpp-lac, laclq, T7, T5, T3, gal, trc, ara ($P_{BAD}$), SP6, $\lambda$-$P_R$, and $\lambda$-$P_L$.

Examples of constitutive and inducible promoters in eukaryotic microorganisms such as yeasts and fungi include, but are not limited to, the AOX-, GAP-, and TEF-promoter.

The term "heterologous" when used with respect to a nucleic acid (DNA or RNA) or protein refers to a nucleic acid or protein that does not occur naturally as part of the organism, cell, genome or DNA or RNA sequence in which it is present, or that is found in a cell or location or locations in the genome or DNA or RNA sequence that differ from that in which it is found in nature. Heterologous nucleic acids or proteins are not endogenous to the cell into which it is introduced, but has been obtained from another cell or synthetically or recombinantly produced. Generally, though not necessarily, such nucleic acids encode proteins that are not normally produced by the cell in which the DNA is transcribed or expressed. Similarly exogenous RNA encodes for proteins not normally expressed in the cell in which the exogenous RNA is present. Heterologous nucleic acids and proteins may also be referred to as foreign nucleic acids or proteins. Any nucleic acid or protein that one of skill in the art would recognize as heterologous or foreign to the cell in which it is expressed is herein encompassed by the term heterologous nucleic acid or protein.

The host cell or micro-organism may in particular be selected from the group of genera consisting of *Aspergillus, Bacillus, Corynebacterium, Escherichia, Saccharomyces, Pseudomonas, Gluconobacter, Penicillium*, and *Pichia*. In particular, the host strain and, thus, host cell suitable for the production of a transinase may be selected from the group of *Escherichia coli, Bacillus subtilis, Bacillus amyloliquefaciens, Corynebacterium glutamicum, Aspergillus niger, Penicillium chrysogenum*, and *Pichia pastoris* host cells.

The proteins having transaminase activity mentioned under n) above are produced by microorganisms present in soil samples collected in the Netherlands and Germany. These microorganisms were enriched from these soil samples in a culture medium using an (R)-amine as the sole nitrogen source for the microorganism for growth. To this end the following six structurally diverse (R)-amines were used as only nitrogen source: (R)-2-aminobutane, (R)-3,3-dimethyl-2-aminobutane, (R)-α-methylbenzylamine, (R)-α-ethylbenzylamine, (R)-1-aminoindan and (R)-1-aminotetralin.

Subsequent to enrichment in liquid medium, the microorganisms were isolated on agar plates containing the respective (R)-amine as sole nitrogen source, pure cultures were grown in the respective liquid enrichment medium again and used for transaminase reactions in whole cell systems. The resulting conversions and enantiomeric excesses of the produced (R)-amines were monitored by HPLC or GC analysis.

The typical desired outcome of a reaction catalysed by an (R)-selective transaminase is the formation of an enantiomerically enriched (R)-amine according to formula 1 [c] from an amino donor and a ketone substrate. Suitable amino donors for (R)-selective transaminase reactions comprise for instance racemic or (R)-MBA, racemic or (R)-1-aminoindan, racemic or (R)-1-aminotetralin, racemic or D-alanine, isopropylamine, benzylamine, racemic or (R)-sec-butylamine (2-aminobutane), β-alanine or racemic or D-3-aminobutyric acid.

Typically 80 mM of amino donor is reacted with 40 mM of ketone substrate in the presence of an (R)-transaminase in an aqueous reaction mixture buffered with 100 mM potassium phosphate (KR) at pH 7.5 at 28° C. Preferably at least 100 mM of ketone substrate are used in the presence of an (R)-transaminase in an aqueous reaction mixture buffered with 100 mM potassium phosphate (KR) at pH 7.5 at 28° C. Optionally water miscible or immiscible solvents can be used to solubilise amino donor or ketone substrate. An (R)-selective transaminase according to this invention will exhibit at least low conversion of 0.5% to the desired enantiomerically enriched (R)-amine starting from equimolar amounts of amino donor and ketone substrate with the enantiomerically enriched (R)-amine having an enantiomeric excess of at least 50% after over night reaction at 28° C.

The form of the (R)-transaminase is not critical; it can be added as (partially) purified enzyme, cell-free extract or crude cell extract; liquid, powder or immobilized form; permeabilised cells, whole cells or culture broth containing cells comprising the transaminase or in any other form.

It is known to the person skilled in the art that transaminase reactions are reversible reactions and the degree of conversion is influenced by the equilibrium of the specific substrates and products. Further it is known to the person skilled in the art that the degree of substrate conversion at equimolar amino donor and ketone substrate concentrations can be increased by for instance in situ product removal by evaporation of one of the reaction products or using resins, or addition of enzymes which further convert one of the reaction products such as pyruvate decarboxylase or lactate dehydrogenase.

Preferably the produced enantiomerically enriched (R)-amine has an e.e. of at least 50%. More preferably the e.e. is at least 60%. Even more preferably the e.e. is at least 70%. Even more preferably the e.e. is at least 80%. Even more preferably the e.e. is at least 90%. Even more preferably the e.e. is at least 95%. Even more preferably the e.e. is at least 96%. Even more preferably the e.e. is at least 97%. Most preferably the produced enantiomerically enriched (R)-amine has an e.e. of at least 99%.

The final result was a collection of 31 microorganisms, which were characterized as shown in table 1.

TABLE 1

The deposits at German Collection of Microorganisms and Cell Cultures (DSMZ) at Braunschweig, Germany were made on Jul. 13th, 2010

| Code | Microorganism (scientific name) | DSMZ deposition number |
|---|---|---|
| 3Na | Rahnella aquatilis | DSM 23797 |
| 3Kb | Rahnella aquatilis | not applicable |
| 3Ba | Ochrobactrum anthropi | not applicable |

TABLE 1-continued

The deposits at German Collection of Microorganisms and Cell Cultures (DSMZ) at Braunschweig, Germany were made on Jul. 13th, 2010

| Code | Microorganism (scientific name) | DSMZ deposition number |
|---|---|---|
| 3Db | Ochrobactrum anthropi | DSM 23793 |
| 3H1 | Sinorhizobium morelense | DSM 23794 |
| 5BaB | Curtobacterium pusillum | DSM 23787 |
| 5BaS | Paecilomyces lilacinus | DSM 23771 |
| 2A2 | Microbacterium ginsengisoli | not applicable |
| 2Ca | Microbacterium ginsengisoli | not applicable |
| 2Cb | Ochrobactrum anthropi | not applicable |
| 2M1 | Pseudomonas citronellolis | DSM 23795 |
| 2Da | Yersinia kristensenii | DSM 23792 |
| 2K1 | Ochrobactrum anthropi | not applicable |
| 6Ab | Ochrobactrum tritici | DSM 23786 |
| 6Bb | Mycobacterium fortuitum | DSM 23789 |
| 6I | Achromobacter spanius | DSM 23791 |
| 6F | Achromobacter spanius | not applicable |
| 1Ea | Achromobacter insolitus | DSM 23790 |
| 1Ia | Mycobacterium frederiksbergense | DSM 23798 |
| 1Ib | Mycobacterium sacrum | DSM 23785 |
| 1Eb | Mycobacterium fluoranthenivorans | not applicable |
| 1A2 | Mycobacterium fluoranthenivorans | not applicable |
| 1Nb | Mycobacterium fluoranthenivorans | DSM 23796 |
| 1Ja | Mycobacterium fluoranthenivorans | not applicable |
| 1A1 | Microbacterium ginsengisoli | DSM 23784 |
| 4D1 | Burkholderia sp. | not applicable |
| 4F1 | Burkholderia tropica | DSM 23799 |
| 4Bd | Cosmospora episphaeria | DSM 23772 |
| 4I | Rahnella aquatilis | not applicable |
| 4Ba | Fusarium oxysporum | DSM 23770 |
| 4Bc | Microbacterium trichothecenolyticum | DSM 23788 |

For the synthesis of enantiomerically enriched (R)-aminotetralin from tetralon preferably the microorganism Sinorhizobium morelense, Rahnella aquatilis or Ochrobactrum anthropi or a transaminase obtainable from any of these species is used. More preferably the microorganism Rahnella aquatilis or Ochrobactrum anthropi or a transaminase obtainable from any of these species. Most preferably the microorganism Ochrobactrum anthropi or a transaminase obtainable from this species is used.

For the synthesis of enantiomerically enriched (R)-aminoindan from indanon preferably the microorganism Paecilomyces filacinus or Curtobacterium pusillum or a transaminase obtainable from any of these species is used. Most preferably the microorganism Curtobacterium pusillum or a transaminase obtainable from this species is used.

For the synthesis of enantiomerically enriched (R)-α-ethylbenzylamine from propiophenone preferably the microorganism Microbacterium ginsengisoli, Yersinia kristensenii, Pseudomonas citronellolis or Ochrobactrum anthropi or a transaminase obtainable from any of these species is used. More preferably the microorganism Yersinia kristensenii, Pseudomonas citronellolis or Ochrobactrum anthropi or a transaminase obtainable from any of these species is used. Even more preferably the microorganism Pseudomonas citronellolis or Ochrobactrum anthropi or a transaminase obtainable from any of these species is used. Most preferably the microorganism Ochrobactrum anthropi or a transaminase obtainable from this species is used.

For the synthesis of enantiomerically enriched (R)-α-methylbenzylamine from acetophenone preferably the microorganism Mycobacterium fortuitum, Ochrobactrum tritici or Achromobacter spanius or a transaminase obtainable from any of these species is used. More preferably the microorganism Ochrobactrum tritici or Achromobacter spanius or a transaminase obtainable from any of these species is used. Most preferably the microorganism *Achromobacter spanius* or a transaminase obtainable from this species is used.

For the synthesis of enantiomerically enriched (R)-3,3-dimethyl-2-aminobutane from 3,3-dimethyl-2-butanone preferably a microorganism of the genus *Mycobacterium* or a transaminase obtainable from this genus is used. More preferably a microorganism from the group of *Mycobacterium frederiksbergense, Mycobacterium sacrum* or *Mycobacterium fluoranthenivorans*, or a transaminase obtainable from one of these species, respectively, is used. Even more preferably the microorganism *Microbacterium ginsengisoli* or *Achromobacter insolitus* or a transaminase obtainable from any of these species is used. Most preferably the microorganism *Achromobacter insolitus* or a transaminase obtainable from this species is used.

For the synthesis of enantiomerically enriched (R)-2-aminobutane from 2-butanone preferably a microorganism of the genus *Burkholderia* or a transaminase obtainable from this genus is used. More preferably a microorganism from the group of *Cosmospora episphaeria* or *Fusarium oxysporum* or a transaminase obtainable from any of these species, respectively, is used. Even more preferably the microorganism *Microbacterium trichothecenolyticum* or a transaminase obtainable from this species is used. Most preferably a microorganism from the group of *Burkholderia* sp., *Burkholderia tropica* or *Rahnella aquatilis*, or a transaminase obtainable from any of these species, respectively, is used.

The re-isolation of the individual microorganisms from the pools deposited can be achieved by plating of suitable dilutions of the pooled microorganisms and re-streaking on the selective enrichment medium containing the respective (R)-amine, on which they have been enriched originally. Repeated re-streaking on the respective (R)-amine containing selective enrichment medium is carried out until only colonies of uniform morphology are obtained. Subsequently 16S rRNA or D2-LSU rRNA sequencing is performed, e.g. by using the validated MicroSEQ® (Applied Biosystems, Carlsbad, Calif., USA) system, to re-identify the individual microorganisms.

Transaminases obtainable from the strains in table 1 include enzymes derived from transaminase gene sequences of the strains in table 1. These gene sequences can be identified and isolated by various methods known to the person skilled in the art such as genome sequencing and sequence comparison with known transaminase sequences, DNA isolation and using probes with DNA sequences having a high degree of identity (at least 80%) to known transaminase genes, enzyme purification and enzyme sequencing, transformation of DNA derived from these strains in other host organisms and selection for growth on (R)-amines followed by DNA sequencing, or combinations of these approaches (Ausubel et al., eds., "Current protocols in molecular biology", Green Publishing and Wiley Interscience, New York 1987).

Accordingly, the present invention also relates to a microorganism comprising an enzyme having (R)-transaminase activity from the group of organisms consisting of *Rahnella aquatilis* (deposited as DSM 23797), *Ochrobactrum anthropi* (deposited as DSM 23793), *Ochrobactrum tritici* (deposited as DSM 23786), *Sinorhizobium morelense* (deposited as DSM 23794), *Curtobacterium pusillium* (deposited as DSM 23787), *Paecilomyces lilacinus* (deposited as DSM 23771), *Microbacterium ginsengisoli, Microbacterium trichothecenolyticum* (deposited as DSM 23788), *Pseudomonas citronellolis* (deposited as DSM 23795), *Yersinia kristensenii* (deposited as DSM 23792), *Achromobacter spanius* (deposited as DSM 23791), *Achromobacter insolitus* (deposited as DSM 23790), *Mycobacterium fortuitum* (deposited as DSM 23789), *Mycobacterium frederiksbergense* (deposited as DSM 23798), *Mycobacterium sacrum* (deposited as DSM 23785), *Mycobacterium fluoranthenivorans* (deposited as DSM 23796), *Burkholderia* sp., *Burkholderia tropica* (deposited as DSM 23799), *Cosmospora episphaeria* (deposited as DSM 23772), and *Fusarium oxysporum* (deposited as DSM 23770).

According to a further embodiment the present invention relates to a microorganism comprising an enzyme having (R)-transaminase activity selected from the group consisting of Cpu-TA1 [SEQ ID No.30], Cpu-TA2 [SEQ ID No.33], Cpu-TA3 [SEQ ID No.35], Raq-TA2 [SEQ ID No.38], Raq-TA3 [SEQ ID No.40], Asp-TA1 [SEQ ID No.43] and Mgi-TA1 [SEQ ID No. 46] or a protein having at least 90%, preferably at least 91%, preferably at least 92%, preferably at least 93%, preferably at least 94%, preferably at least 95%, preferably at least 96%, preferably at least 97%, preferably at least 98%, preferably at least 99% identity to any of these amino acid sequences.

According to a further embodiment the present invention relates to a polypeptide having (R)-transaminase activity and obtainable from an organism selected from the group of organisms consisting of *Rahnella aquatilis* (deposited as DSM 23797), *Ochrobactrum anthropi* (deposited as DSM 23793), *Ochrobactrum tritici* (deposited as DSM 23786), *Sinorhizobium morelense* (deposited as DSM 23794), *Curtobacterium pusillium* (deposited as DSM 23787), *Paecilomyces lilacinus* (deposited as DSM 23771), *Microbacterium ginsengisoli, Microbacterium trichothecenolyticum* (deposited as DSM 23788), *Pseudomonas citronellolis* (deposited as DSM 23795), *Yersinia kristensenii* (deposited as DSM 23792), *Achromobacter spanius* (deposited as DSM 23791), *Achromobacter insolitus* (deposited as DSM 23790), *Mycobacterium fortuitum* (deposited as DSM 23789), *Mycobacterium frederiksbergense* (deposited as DSM 23798), *Mycobacterium sacrum* (deposited as DSM 23785), *Mycobacterium fluoranthenivorans* (deposited as DSM 23796), *Burkholderia* sp., *Burkholderia tropica* (deposited as DSM 23799), *Cosmospora episphaeria* (deposited as DSM 23772), and *Fusarium oxysporum* (deposited as DSM 23770).

According to a further embodiment the invention relates to a polypeptide having (R)-transaminase activity and at least 90%, preferably at least 91%, preferably at least 92%, preferably at least 93%, preferably at least 94%, preferably at least 95%, preferably at least 96%, preferably at least 97%, preferably at least 98%, preferably at least 99% sequence identity to a polypeptide having (R)-transaminase activity and obtainable from an organism selected from the group of organisms consisting of *Rahnella aquatilis* (deposited as DSM 23797), *Ochrobactrum anthropi* (deposited as DSM 23793), *Ochrobactrum tritici* (deposited as DSM 23786), *Sinorhizobium morelense* (deposited as DSM 23794), *Curtobacterium pusillium* (deposited as DSM 23787), *Paecilomyces lilacinus* (deposited as DSM 23771), *Microbacterium ginsengisoli, Microbacterium trichothecenolyticum* (deposited as DSM 23788), *Pseudomonas citronellolis* (deposited as DSM 23795), *Yersinia kristensenii* (deposited as DSM 23792), *Achromobacter spanius* (deposited as DSM 23791), *Achromobacter insolitus* (deposited as DSM 23790), *Mycobacterium fortuitum* (deposited as DSM 23789), *Mycobacterium frederiksbergense* (deposited as DSM 23798), *Mycobacterium sacrum* (deposited as DSM 23785), *Mycobacterium fluoranthenivorans* (deposited as DSM 23796), *Burkholderia* sp., *Burkholderia tropica*

(deposited as DSM 23799), *Cosmospora episphaeria* (deposited as DSM 23772), and *Fusarium oxysporum* (deposited as DSM 23770).

According to a further embodiment the invention relates to a polypeptide having (R)-transaminase activity selected from the group consisting of Cpu-TA1 [SEQ ID No.30], Cpu-TA2 [SEQ ID No.33], Cpu-TA3 [SEQ ID No.35], Raq-TA2 [SEQ ID No.38], Raq-TA3 [SEQ ID No.40], Asp-TA1 [SEQ ID No.43] and Mgi-TA1 [SEQ ID No. 46] or a protein having at least 90%, preferably at least 91%, preferably at least 92%, preferably at least 93%, preferably at least 94%, preferably at least 95%, preferably at least 96%, preferably at least 97%, preferably at least 98%, preferably at least 99% identity to any of these polypeptide sequences.

According to a further embodiment the present invention relates to a nucleic acid comprising a sequence encoding a polypeptide having (R)-transaminase activity and at least 90%, preferably at least 91%, preferably at least 92%, preferably at least 93%, preferably at least 94%, preferably at least 95%, preferably at least 96%, preferably at least 97%, preferably at least 98%, preferably at least 99% sequence identity to a polypeptide having (R)-transaminase activity and obtainable from an organism selected from the group of organisms consisting of *Rahnella aquatilis* (deposited as DSM 23797), *Ochrobactrum anthropi* (deposited as DSM 23793), *Ochrobactrum tritici* (deposited as DSM 23786), *Sinorhizobium morelense* (deposited as DSM 23794), *Curtobacterium pusillium* (deposited as DSM 23787), *Paecilomyces lilacinus* (deposited as DSM 23771), *Microbacterium ginsengisoli*, *Microbacterium trichothecenolyticum* (deposited as DSM 23788), *Pseudomonas citronellolis* (deposited as DSM 23795), *Yersinia kristensenii* (deposited as DSM 23792), *Achromobacter spanius* (deposited as DSM 23791), *Achromobacter insolitus* (deposited as DSM 23790), *Mycobacterium fortuitum* (deposited as DSM 23789), *Mycobacterium frederiksbergense* (deposited as DSM 23798), *Mycobacterium sacrum* (deposited as DSM 23785), *Mycobacterium fluoranthenivorans* (deposited as DSM 23796), *Burkholderia* sp., *Burkholderia tropica* (deposited as DSM 23799), *Cosmospora episphaeria* (deposited as DSM 23772), and *Fusarium oxysporum* (deposited as DSM 23770).

According to a further embodiment the present invention relates to a nucleic acid comprising a sequence encoding a polypeptide having (R)-transaminase activity selected from the group consisting of Cpu-TA1 [SEQ ID No.30], Cpu-TA2 [SEQ ID No.33], Cpu-TA3 [SEQ ID No.35], Raq-TA2 [SEQ ID No.38], Raq-TA3 [SEQ ID No.40], Asp-TA1 [SEQ ID No.43] and Mgi-TA1 [SEQ ID No. 46] or a protein having at least 90%, preferably at least 91%, preferably at least 92%, preferably at least 93%, preferably at least 94%, preferably at least 95%, preferably at least 96%, preferably at least 97%, preferably at least 98%, preferably at least 99% identity to any of these polypeptide sequences.

Enzymes derived from gene sequences of the strains in table 1 also include enzymes with sequence identities of at least 90%, preferably at least 91%, preferably at least 92%, preferably at least 93%, preferably at least 94%, preferably at least 95%, preferably at least 96%, preferably at least 97%, preferably at least 98%, preferably at least 99% which are obtained by mutagenesis of genes derived from the strains in table 1. Mutagenesis methods are known to the person skilled in the art and include gene synthesis as well as mutagenesis methods using mutagenic primers (Bloom & Arnold, *Proc Natl Acad Sci USA* 2009, 106, 9995).

EXAMPLES

General

Microbial Growth Media
LB (Luria Bertani) Medium
10 g/l Bacto Tryptone (BD, Le Pont de Claix, France)
5 g/l Bacto Yeast Extract (BD, Le Pont de Claix, France)
5 g/l NaCl (Sigma-Aldrich, Steinheim, Germany)
15 g/l Bacto Agar (for solid media, BD, Le Pont de Claix, France)

The components were dissolved in demineralised water and if necessary the pH was adjusted to 7.0. The media were sterilized by autoclaving for 20 min at 121° C. For solid media agar was added before autoclaving. Antibiotics were added after the autoclaved medium had cooled down to 60° C.

Selective Enrichment Media (SEM)
10 g/l Difco Yeast Carbon Base (YCB, BD, Sparks, Md., USA)
55 mM glycerol (Merck, Darmstadt, Germany)
10 mM pyruvic acid (Sigma-Aldrich, Steinheim, Germany)
5 mM (R)-amine substrate
15 g/l Difco Agar Noble (BD, Le Pont de Claix, France)

A stock solution of YCB medium (100 g/l), 550 mM glycerol and 100 mM pyruvic acid was prepared in MilliQ water (Millipore, Billerica, Mass., USA) and sterilized by filtration through 0.22 μm sterile filters. Liquid enrichment media were prepared by adding an (R)-amine substrate selected from the group (R)-2-aminobutane, (R)-3,3-dimethyl-2-aminobutane, (R)-α-methylbenzylamine, (R)-α-ethylbenzylamine, (R)-1-aminoindan and (R)-1-aminotetralin to a 1:10 with sterile MilliQ water diluted stock solution of the enrichment medium. Solid enrichment media were prepared accordingly with autoclaved MilliQ water containing Agar Noble to obtain a final concentration of 15 g/l.

Antibiotics

LB medium containing carbenicillin or neomycine in final concentrations of 100 μg/ml was used to select and cultivate recombinant *Escherichia coli* strains containing expression vectors comprising [SEQ IDs No. 2, 4, 6, 8, 10, 12, 14, 16, 18, 20, 22, 24, 26] to maintain the plasmids. Carbenicllin and neomycine stock solutions (50 mg/ml) were sterilized by filtration through 0.22 μm sterile filters.

Molecular and Genetic Techniques

Standard genetic and molecular biology techniques are generally known in the art and have been previously described (Maniatis et al. 1982 "Molecular cloning: a laboratory manual". Cold Spring Harbor Laboratory, Cold Spring Harbor, N.Y.; Miller 1972 "Experiments in molecular genetics", Cold Spring Harbor Laboratory, Cold Spring Harbor; Sambrook and Russell 2001 "Molecular cloning: a laboratory manual" (3rd edition), Cold Spring Harbor Laboratory, Cold Spring Harbor Laboratory Press; F. Ausubel et al, eds., "Current protocols in molecular biology", Green Publishing and Wiley Interscience, New York 1987).

Plasmids and Strains

*E. coli* strains TOP10 (Invitrogen, Carlsbad, Calif., USA) was used for all cloning procedures. *E. coli* was also used for protein expression. For induction of gene expression L-arabinose was used at a final concentration of 0.02% (w/v).

Cloning of Target Genes

The target genes according to [SEQ IDs No. 2, 4, 6, 8, 10, 12, 14, 16, 18, 20, 22, 24, 26] were codon pair optimised according to a procedure described in WO08000632. attB sites were added to all genes upstream of the ribosomal binding site and start codon and downstream of the stop codon to facilitate cloning using the Gateway technology (Invitrogen, Carlsbad, Calif., USA). Synthetic genes were obtained from Geneart (Regensburg, Germany). The gene constructs were cloned into a pBAD/Myc-HisC (Invitrogen, Carlsbad, Calif., USA) derived expression vector using the Gateway technology (Invitrogen) via the introduced attB sites and pDONR201 (Invitrogen) as entry vector as described in the manufacturer's protocols (www.invitrogen.com). This way the pBAD expression vectors were obtained, respectively. The corresponding expression strains were obtained by transformation of chemically competent *E. coli* cells with the respective pBAD-expression vectors.

Identification of Plasmids

Plasmids carrying the different genes were identified by genetic, biochemical, and/or phenotypic means generally known in the art, such as resistance of transformants to antibiotics, PCR diagnostic analysis of transformant or purification of plasmid DNA, restriction analysis of the purified plasmid DNA or DNA sequence analysis.

Determination Protein Concentrations in Solution

The concentrations of proteins in solutions such as cell-free extracts (CFEs) were determined using a modified protein-dye binding method as described by Bradford in *Anal. Biochem.* 72: 248-254 (1976). Of each sample 50 μl in an appropriate dilution was incubated with 950 μl reagent (100 mg Brilliant Blue G250 dissolved in 46 ml ethanol and 100 ml 85% ortho-phosphoric acid, filled up to 1,000 ml with milli-Q water) for at least five minutes at room temperature. The absorption of each sample at a wavelength of 595 nm was measured in a Perkin Elmer Lambda20 or a Lambda35 UV/VIS spectrophotometer. Using a calibration line determined with solutions containing known concentrations of bovine serum albumin (BSA, ranging from 0.0125 mg/ml to 0.20 mg/ml) the protein concentration in the samples was calculated.

Analysis

High-Pressure Liquid Chromatography (HPLC) Analysis

Ketones and amines containing aromatic groups were analysed on a Prevail C18 15 cm column. For the separation and quantification of the enantiomers of α-methylbenzylamine, α-ethylbenzylamine, 2-aminotetralin a Crownpak Cr (+) column (Daicel) with post-column dervatisation of the amines using o-phtalaldehyde plus mercaptoethanol and fluorescence detection was used. For the separation and quantification of the enantiomers of 1-aminotetralin and 1-aminoindan a Prevail C18 15 cm plus Crownpak Cr (+) columns were used with post-column dervatisation of the amines using o-phtalaldehyde plus mercaptoethanol and fluorescence detection was used.

Gas Chromatography

Alkyl ketones and alkyl amines such as 2-butanone, 2-aminobutane, 3,3-dimethyl-butanone, and 3,3-dimethyl-2-aminobutane were analysed on a CP-Sil 8 CB column (Varian) for amines column using commercially available reference materials (Sigma-Aldrich). For the separation and quantification of the (R)- and (S)-alkyl amines a Chiralsil-CB column (Agilent) was used.

Example 1—Enrichment of Microorganisms on (R)-Amines as Only Nitrogen Source

Soil samples from various places in the Netherlands and Germany were suspended in 100 mM potassium phosphate ($KP_i$) buffer pH 7.0 and incubated with shaking at 180 rotations per minute (rpm) and 28° C. for 1 hour. The suspensions were filtered through Whatman filter paper. 100 μl of filtrate, each, was used to inoculate 100 ml Erlenmeyer flasks containing 10 ml SEM containing one of the six (R)-amines selected from the group (R)-2-aminobutane, (R)-3,3-dimethyl-2-aminobutane, (R)-α-methylbenzylamine, (R)-α-ethylbenzylamine, (R)-1-aminoindan and (R)-1-aminotetralin. The flasks were incubated with shaking on an orbitary shaker at 180 rpm and 28° C. When microbial growth was obtained in form of significant turbidity of the culture medium or "cell aggregates", 100 μl of this culture medium was used to inoculate SEM containing 5 mM of the same (R)-amine. After two such passages 100 μl of a 1:100 dilution of the last culture medium was plated on SEM agar plates containing 5 mM of the corresponding (R)-amine. Additionally approximately 10 μl of the undiluted culture was streaked out on SEM agar plates containing 5 mM of the corresponding (R)-amine. The inoculated agar plates were incubated at 28° C. until growth was observed. Colonies with different morphology were restreaked on fresh SEM plates to separate different microbial species. The re-streaking was continued until pure cultures with uniform morphologies were obtained after incubation at 28° C. and storage at 4° C.

Selected micro-organisms were sent for MicroSEQ® (Applied Biosystems, Carlsbad, Calif., USA) Identification to BaseClear (Leiden, The Netherlands). The bacterial or fungal 16S or D2-LSU rRNA sequences obtained were compared to the validated MicroSEQ® sequence database (at BaseClear, Leiden, The Netherlands) and in case no identity above 99% was obtained compared to the non-redundant (nr) nucleotide database using the BlastN algorithm on the NCBI Blast homepage (URL: www.ncbi.nlm.nih.gov/BLAST/). An overview of the results of these sequence analyses is given in table 2.

TABLE 2

Identification of enrichment isolates by MicroSeq Identification

| (R)-amine | Isolate | Genus | species | % match |
|---|---|---|---|---|
| 1-aminotetralin | 3Na | *Rahnella* | *aquatilis* | 99.8 |
| 1-aminotetralin | 3Kb | *Rahnella* | *aquatilis* | 99.8 |
| 1-aminotetralin | 3Ba | *Ochrobactrum* | *anthropi* | 100 |
| 1-aminotetralin | 3Db | *Ochrobactrum* | *anthropi* | 100 |
| 1-aminotetralin | 3H1 | *Sinorhizobium* | *morelense* | 100 |
| 1-aminoindan | 5BaB | *Curtobacterium* | *pusillum* | 100 |
| 1-aminoindan | 5BaS | *Paecilomyces* | *lilacinus* | 100 |
| α-ethylbenzylamine | 2A2 | *Microbacterium* | *ginsengisoli* | 99.8 |
| α-ethylbenzylamine | 2Ca | *Microbacterium* | *ginsengisoli* | 99.8 |
| α-ethylbenzylamine | 2Cb | *Ochrobactrum* | *anthropi* | 100 |
| α-ethylbenzylamine | 2M1 | *Pseudomonas* | *citronellolis* | 99.0 |

TABLE 2-continued

Identification of enrichment isolates by MicroSeq Identification

| (R)-amine | Isolate | Genus | species | % match |
|---|---|---|---|---|
| α-ethylbenzylamine | 2Da | *Yersinia* | *kristensenii* | 99.1 |
| α-ethylbenzylamine | 2K1 | *Ochrobactrum* | *anthropi* | 100 |
| α-methylbenzylamine | 6Ab | *Ochrobactrum* | *tritici* | 100 |
| α-methylbenzylamine | 6Bb | *Mycobacterium* | *fortuitum* | 99.3 |
| α-methylbenzylamine | 6I | *Achromobacter* | *spanius* | 100 |
| α-methylbenzylamine | 6F | *Achromobacter* | *spanius* | 100 |
| 3,3-dimethyl-2-aminobutane | 1Ea | *Achromobacter* | *insolitus* | 99.6 |
| 3,3-dimethyl-2-aminobutane | 1Ia | *Mycobacterium* | *frederiksbergense* | 99.4 |
| 3,3-dimethyl-2-aminobutane | 1Ib | *Mycobacterium* | *sacrum* | 99.4 |
| 3,3-dimethyl-2-aminobutane | 1Eb | *Mycobacterium* | *fluoranthenivorans* | 100 |
| 3,3-dimethyl-2-aminobutane | 1A2 | *Mycobacterium* | *fluoranthenivorans* | 99.8 |
| 3,3-dimethyl-2-aminobutane | 1Nb | *Mycobacterium* | *fluoranthenivorans* | 100 |
| 3,3-dimethyl-2-aminobutane | 1Ja | *Mycobacterium* | *fluoranthenivorans* | 100 |
| 3,3-dimethyl-2-aminobutane | 1A1 | *Microbacterium* | *ginsengisoli* | 99.8 |
| 2-aminobutane | 4D1 | *Burkholderia* | sp. | 100 |
| 2-aminobutane | 4F1 | *Burkholderia* | *tropica* | 100 |
| 2-aminobutane | 4Bd | *Cosmospora* | *episphaeria* | 99.0 |
| 2-aminobutane | 4I | *Rahnella* | *aquatilis* | 99.8 |
| 2-aminobutane | 4Ba | *Fusarium* | *oxysporum* | 100 |
| 2-aminobutane | 4Bc | *Microbacterium* | *trichothecenolyticum* | 99.8 |

Example-2 Detection of (R)-Transaminase Activity in Enrichment Isolates

From the pure cultures of the enrichment isolates on SEM agar plates 25 ml liquid SEM cultures containing 5 mM of the respective (R)-amine, on which the microorganisms had been enriched on, were inculated and cultivated on an orbitary shaker at 180 rotations per minute (rpm) and at 28° C. until the cultures turned turbid. Subsequently the cultures were transferred to 50 ml centrifuge tubes and centrifuged for 10 min at 50,000×g in JA-25.50 rotor in Beckman Avanti J-20 XPI centrifuge (Beckman-Coulter, Woerden, The Netherlands). The cell pellets were resuspended in 2 ml 100 mM potassium phosphate ($KP_i$) buffer pH 7.0 containing 0.1 mM pyridoxal 5'-phosphate (PLP). The cell suspensions were used to determine (R)-transaminase activity using 40 mM of amino donor and ketone substrate. Cell suspensions of enrichment isolates 3Kb, 3Na, 3Ba, 3Db, and 3H1 were tested with 40 mM (R)-α-methylbenzylamine as amine donor and 1-tetralone as ketone substrate yielding acetophenone and 1-aminotetraline as products. Cell suspensions of enrichment isolates 5BaB and 5BaS were tested with 40 mM (R)-α-methylbenzylamine as amine donor and 1-aminoindane as ketone substrate yielding acetophenone and 1-aminoindane as products. Cell suspensions of enrichment isolates 2A2, 2Ca, 2Cb, 2M1, 2 Da, and 2K1 were tested with 40 mM (R)-α-methylbenzylamine as amine donor and propiophenone as ketone substrate yielding acetophenone and α-ethylbenzylamine as products. Cell suspensions of enrichment isolates 5BaB and 5BaS were tested with 40 mM (R)-α-methylbenzylamine as amine donor and 1-aminoindane as ketone substrate yielding acetophenone and 1-aminoindane as products. Cell suspensions of enrichment isolates 6Ab, 6Bb, 6I, and 6F were tested with 40 mM benzylamine as amine donor and acetophenone as ketone substrate yielding benzaldehyde and α-methylbenzylamine as products. The concentrations and the enantiomeric excess (e.e.) of the formed amine products were determined by HPLC as described in the general part. The results of the HPLC analyses are summarised in table 3.

TABLE 3

Concentrations and enantiomeric excesses of (R)-amines produced by the enriched microorganisms from amino donors and ketone substrates.

| (R)-amine produced | Isolate | Amine product [g/l] | e.e. (R) |
|---|---|---|---|
| 1-aminotetralin | 3Na | 0.31 | 99 |
| 1-aminotetralin | 3Kb | 0.24 | 99.6 |
| 1-aminotetralin | 3Ba | 0.40 | 98 |
| 1-aminotetralin | 3Db | 0.41 | 99 |
| 1-aminotetralin | 3H1 | 0.12 | 88 |
| 1-aminoindan | 5BaB | 0.17 | 99.8 |
| 1-aminoindan | 5BaS | 0.17 | 99.8 |
| α-ethylbenzylamine | 2A2 | 0.32 | 95 |
| α-ethyibenzylamine | 2Ca | 0.29 | 98 |
| α-ethylbenzylamine | 2Cb | 0.25 | 98 |
| α-ethylbenzylamine | 2M1 | 0.33 | 98 |
| α-ethylbenzylamine | 2Da | 0.34 | 96 |
| α-ethylbenzylamine | 2K1 | 0.30 | 98 |
| α-methylbenzylamine | 6Ab | 0.08 | 94 |
| α-methylbenzylamine | 6Bb | 0.17 | 64 |
| α-methylbenzylamine | 6I | 0.09 | 94 |
| α-methylbenzylamine | 6F | 0.10 | 70 |

These results demonstrate the presence of transaminases with good to excellent (R)-selectivity in the enriched microorganisms.

Example 3—Expression of (R)-Transaminases from Public Databases

The codon pair optimised genes encoding the polypeptides of the putative transaminases as summarized in table 4 were cloned into a pBAD/Myc-HisC derived expression vector (as described in EP1513946) using the Gateway technology (Invitrogen) according to the manufacturer's protocols (www.invitrogen.com) as described in the general part.

TABLE 4

Overview of the polypeptide, nucleotide sequnces, and accession numbers

| Polypeptide (amino acid sequence) | Nucleotide (codon-pair-optimised gene) | Protein accession number | Plasmid name |
|---|---|---|---|
| SEQ ID No. 1 | SEQ ID No. 2 | XP_001209325 | pBAD-XP_001209325 |
| SEQ ID No. 3 | SEQ ID No. 4 | XP_002564064 | pBAD-XP_002564064 |
| SEQ ID No. 5 | SEQ ID No. 6 | EEU44019 | pBAD-EEU44019 |
| SEQ ID No. 7 | SEQ ID No. 8 | XP_001402221 | pBAD-XP_001402221 |
| SEQ ID No. 9 | SEQ ID No. 10 | YP_761201 | pBAD-YP_761201 |
| SEQ ID No. 11 | SEQ ID No. 12 | YP_838940 | pBAD-YP_838940 |
| SEQ ID No. 13 | SEQ ID No. 14 | YP_955297 | pBAD-YP_955297 |
| SEQ ID No. 15 | SEQ ID No. 16 | EDI73966 | pBAD-EDI73966 |
| SEQ ID No. 17 | SEQ ID No. 18 | NP_085750 | pBAD-NP_085750 |
| SEQ ID No. 19 | SEQ ID No. 20 | EDH25885 | pBAD-EDH25885 |
| SEQ ID No. 21 | SEQ ID No. 22 | EBP64591 | pBAD-EBP64591 |
| SEQ ID No. 23 | SEQ ID No. 24 | ECU93014 | pBAD-ECU93014 |
| SEQ ID No. 25 | SEQ ID No. 26 | YP_366475 | pBAD-YP_366475 |

Additionally codon-pair optimised synthetic genes encoding for the polypeptides L-threonine aldolase (LTA_SAV, accession number Q82N15) from *Streptomyces avelmitilis* (as negative control), and (R)-transaminases ABN35871 (Sequence 2 from U.S. Pat. No. 7,169,592) and AAN21261 (Sequence 1 from U.S. Pat. No. 6,413,752) were ordered and cloned as described above. After transformation of competent *E. coli* TOP10 cells and plating on selective LB agar plates containing 100 µg/ml antibiotic, the respective recombinant *E. coli* pBAD strains as given in table 4 were obtained. 5 ml LB precultures plus 50 µg/ml antibiotic preculturures were inocululated with from the respective agar plates and cultivated over night at 28° C. and 180 rpm on an orbitary shaker. From such precultures expression cultures were inoculated in Erlenmeyer flasks containing 50-100 ml LB plus 50 µg/ml antibiotic to a start cell density of $OD_{620}=0.05$. These cultures were incubated at 28° C. and 180 rpm on an orbitary shaker. In the middle of the exponential growth phase ($OD_{620}$ of about 0.6) the expression of the target genes was induced by the addition of 0.02% (w/v) L-arabinose to the culture flasks. After induction the cultivation was continued at 28° C. and 180 rpm on an orbitary shaker over night (about 20 h). Subsequently the cells were harvested by centrifugation at 5,000×g for 10 min at 4° C. The supernatant was discarded and the cells were resuspended in twice the volume of wet weight of ice-cold 50 mM $KP_i$ buffer pH 7.5 containing 0.1 mM PLP. Cell-free extracts (CFEs) were obtained by sonification of the cell suspensions using a Sonics (Meyrin/Satigny, Switzerland) Vibra-Cell VCX130 sonifier (output 100%, 10 s on/10 s off, for 10 min) with cooling in an ice/acetone bath and centrifugation in an Eppendorf (Hamburg, Germany) 5415R centrifuge at 13,000×g and 4° C. for 30 min. The supernatants (=CFEs) were transferred to fresh tubes and stored on ice for immediate use or stored at −20° C. Protein concentrations in the CFEs were determined using a modified method according to Bradford as described in the general part Example 4—Racemic Resolution of (RS)-α-Methylbenzylamine Cell-free extracts (CFEs) with heterologously in *E. coli* expressed transaminases XP_001209325 and EDH25885 were tested for (R)-transaminase activity and compared with CFEs containing heterologously in *E. coli* expressed L-threonine aldolase (LTA_SAV, accession number Q82N15) from *Streptomyces avelmitilis* (as negative control), and (R)-transaminases ABN35871 (Sequence 2 from U.S. Pat. No. 7,169,592) and AAN21261 (Sequence 1 from EP987332) in the racemic resolution of (RS)-α-methylbenzylamine. In a total reaction volume of 0.25 ml 0.1 ml of the CFEs were mixed with 80 mM (RS)-α-methylbenzylamine (MBA), 40 mM sodium pyruvate in 100 mM $KP_i$ buffer containing 0.1 mM PLP and incubated at 28° C. for 20 h. The reactions were stopped by addition of 0.9 ml stopping reagent (50% (v/v) acetonitrile in $H_2O$ containing 0.1% (v/v) formic acid) to 0.1 ml reaction volume and analysed by HPLC on a chiral phase as described in the general part. The results of the HPLC analysis are given in table 5.

TABLE 5 concentration and e.e. of α-MBA in transaminase reactions

| Enzyme | % e.e. (S)-α-MBA | (S)-α-MBA [g/l] | (R)-α-MBA [g/l] |
|---|---|---|---|
| ABN35871 | 63 | 0.5 | 0.1 |
| AAN21261 | 22 | 0.5 | 0.3 |
| EDH25885 | 10 | 0.5 | 0.4 |
| XP_001209325 | >99 | 0.5 | <0.01 |
| LTA_SAV | <2 | 0.5 | 0.5 |

These results show that XP_001209325 is a very efficient and selective (R)-transaminase, because it selectively converted all (R)-α-MBA but not (S)-α-MBA. Other (R)-transaminases like ABN35871 or AAN21261 were also selective, but at clearly lower productivities resulting in lower e.e.s in the racemic resolution of (RS)-α-MBA. EDH25885 also exhibited low (R)-selective trnasminase activity on (RS)-α-MBA.

Example 5—Synthesis of Enantiomerically Enriched (R)-Amines

In a final volume of 0.25 µl buffered with 100 mM potassium phosphate ($KP_i$) at pH 7.5 equimolar amounts of 70 mM of amino donor and 70 mM of ketone substrate were reacted in the presence of 0.1 ml CFE of a transaminase at 28° C. for 24 h. CFE comprising transaminases XP_001209325, AAN21261 and ABN35871, respectively, was incubated with benzylacetone and α-methylbenzylamine yielding 4-phenyl-2-butylamine and acetophenone; propiophenone and α-methylbenzylamine yielding α-ethylbenzylamine and acetophenone; 1-indanone and α-methylbenzylamine yielding 1-aminoindan and acetophenone; 1-tetralone and α-methylbenzylamine yielding 1-aminotetralin and acetophenone; 2-tetralone and α-methylbenzylamine yielding 2-aminotetralin and acetophenone; butanone and α-methylbenzylamine yielding 2-aminobutane and acetophenone; and 3,3-dimethyl-2-butanone and α-methylbenzylamine yielding 3,3-dimethyl-2-aminobutane and acetophenone, respectively. The reactions were stopped by addition of 0.75 ml stopping reagent (50% (v/v) acetonitrile in H$_2$O containing 0.1% (v/v) formic acid) to 0.25 ml reaction volume. The product concentrations and enantiomeric excesses were analysed by HPLC as described in the general part. The results of the HPLC analysis are given in table 6.

TABLE 6

Amine product concentrations and e.e.s with transaminase XP_001209325 compared to transaminases AAN21261 and ABN35871. n.d.: not determined

| | (R)-amine product | | | | | |
|---|---|---|---|---|---|---|
| | XP_001209325 | | AAN21261 | | ABN35871 | |
| | amine [mM] | e.e. [%] | amine [mM] | e.e. [%] | amine [mM] | e.e. [%] |
| 4-phenyl-2-butylamine | 16.0 | n.d. | <0.1 | n.d. | <0.1 | n.d. |
| 2-aminobutane | 6.2 | 69 | 0.9 | n.d. | 6.9 | −27 |
| 3,3-dimethyl-butylamine | 0.7 | 50 | 0.3 | n.d. | 6.4 | 97 |
| 1-aminoindan | <0.1 | n.d. | <0.1 | n.d. | <0.1 | n.d. |
| α-ethylbenzylamine | 1.7 | 99 | 7.9 | 99 | 2.3 | 99 |
| 1-aminotetralin | <0.1 | n.d. | <0.1 | n.d. | <0.1 | n.d. |
| 2-aminotetralin | 0.4 | 96 | 0.7 | 61 | 0.3 | 97 |

Further CFE comprising transaminase YP_955297 was incubated with propiophenone and α-methylbenzylamine yielding α-ethylbenzylamine and acetophenone. The reaction was stopped by addition of 0.75 ml stopping reagent (50% (v/v) acetonitrile in H$_2$O containing 0.1% (v/v) formic acid) to 0.25 ml reaction volume. The product concentration and enantiomeric excess was analysed by HPLC as described in the general part. After 24 h incubation at 28° C. 0.87 mmol/l (R)-α-ethylbenzylamine was obtained with an e.e. of 99%.

The above results show transaminases XP_001209325 and YP_955297 are highly selective (R)-transaminases. Further it becomes clear that XP_001209325 has a different substrate spectrum than the transaminases AAN21261 and ABN35871: 4-phenyl-2-butylamine was formed in significant concentrations by XP_001209325 but not by transaminases AAN21261 and ABN35871 (table 6). Additionally XP_001209325 produced enantiomerically enriched (R)-2-aminobutane from 2-butanone, while ABN35871 delivered enantiomerically enriched (S)-2-aminobutane (table 6).

Example 6—Selectivity of (R)-Transaminases on Chiral α-Methylbenzylamines

To examine the enantioselectivity of (R)-transaminases they were tested in the conversion of the pure enantiomers forms of α-methylbenzylamine (MBA). Cell-free extracts containing transaminses as prepared in EXAMPLE 3 were tested separately in their activity on (R)-MBA and (S)-MBA, respectively, with pyruvate as ketone substrate in a spectrophotometric assay in a Perkin Elmer Lambda35 UV/VIS spectrophotometer thermostated at 30° C. at a wavelength of 300 nm.

In a final reaction volume of 1 ml 50 µl of a suitable dilution of a CFE containing transaminase were mixed in disposable plastic UV or quartz cuvettes with 12.5 mM (R)- or (S)-MBA and 5 mM sodium pyruvate in the presence of 50 mM KP$_i$ buffer pH 7.5 containing 0.1 mM PLP. The reactions were started by addition of 10 µl of 0.5 M sodium pyruvate (in 50 mM KP$_i$ buffer pH 7.5, 0.1 mM PLP) to the other assay components, which had been pre-incubated in the photometer at 30° C. for 5 min. After addition of sodium pyruvate the absorption at 300 nm was recorded and the transaminase activity in the samples (CFEs) was calculated according to the law of Lambert-Beer with an molar extinction coefficient for acetophenone of ε=0.28 cm$^2$/µmol. One unit (U) of transaminase activity is defined as 1 µmol of acetophenone formed from 12.5 mM (R)-MBA or (S)-MBA and 5 mM sodium pyruvate at 30° C. in 50 mM KP$_i$ buffer pH 7.5 containing 0.1 mM PLP per minute. The specific transaminase activities of the CFEs (U/mg total CFE protein) were calculated by dividing the volumetric activity values (U/ml CFE) by the total protein concentration as determined according to the general procedures. The ratio of specific transaminase activities on (R)-over (S)-MBA are defined as the Transaminase Enantioselectivity Value (TEV). An (R)-selective transaminase is defined as a transaminase with a TEV value of >1. A good (R)-selectivity is defined as a specific activity ratio on (R)-over (S)-MBA of TEV 5. A high (R)-selectivity is defined as a specific activity ratio on (R)-over (S)-MBA of TEV≥10. The specific activities of the transaminases in the CFEs on (R)- and (S)-MBA and the TEVs as determined in these experiments are given in table 7.

TABLE 7 specific transaminase activities on (R)- and (S)-MBA and TEVs

| Transaminase | Activity (R)-MBA [mU/mg] | Activity (S)-MBA [mU/mg] | TEV |
|---|---|---|---|
| XP_001209325 | 559 | 38 | 15 |
| XP_002564064 | 12 | 0.9 | 13 |
| YP_761201 | 32 | 7.2 | 4 |
| YP_955297 | 210 | 26 | 8 |
| NP_085750 | 4.6 | 0.6 | 8 |
| EBP64591 | 18 | 13 | 1.3 |
| EDI73966 | 15 | 14 | 1.1 |
| ABN35871 | 1111 | 20 | 56 |
| AAN21261 | 578 | 39 | 15 |

As becomes clear from this experiment the transaminases XP_001209325, XP_002564064, YP_761201, YP_955297, NP_085750, EBP64591, and EDI73966 are (R)-selective transaminases as are transaminases ABN35871 and AAN21261. Transaminases YP_955297 and NP_085750 exhibited good (R)-selectivity with TEVs of above 5, while XP_001209325 and XP_002564064 and even showed high (R)-selectivity with TEVs of above 10.

Example 7—Re-Isolation of Microorganisms from Pooled Deposits

The re-isolation of the individual microorganisms from the pooled deposit is be achieved by plating of 1:1000, 1:10,000 and further dilutions of the pooled deposit on selective enrichment medium (SEM) agar plates containing one of the six (R)-amines as sole nitrogen source as described in the general part and EXAMPLE 1. By repeated re-streaking on the SEM agar plates containing the respective (R)-amine, on which they have been enriched originally, pure cultures are obtained. Repeated re-streaking on the respective (R)-amine containing selective enrichment medium is carried out until only colonies of uniform morphology are obtained. Subsequently 16S rRNA or D2-LSU rRNA sequencing is performed using the validated MicroSEQ® (Applied Biosystems, Carlsbad, Calif., USA) system, to re-identify the individual microorganisms.

Example 8—Enzymatic Transamination of Phenoxyacetone

Cell-free extract with heterologously in *E. coli* expressed (R)-transaminase XP_001209325 [SEQ ID No.1] (2 U/ml) as produced and assayed as in EXAMPLE 3 and EXAMPLE 6 was incubated with 0.1 M of ketone substrate phenoxyacetone and 0.5 M of the amino donor isopropylamine, (RS)-2-butylamine (effectively 0.25 M (R)-2-butylamine) and (RS)-α-methylbenzylamine (effectively 0.25 M (R)-MBA), respectively, in 50 mM $KP_i$ buffer pH 7.5 containing 0.1 mM PLP at 30° C. for 24 h. The amount of 1-phenoxy-2-propylamine formed was measured by HPLC analysis. The HPLC conditions were as follows:

50 µl of reaction mixture was added to 950 µl of a 50:50 mixture of acetonitrile/water with 0.01% (v/v) formic acid and centrifuged for 5 min at 13,000 rpm.
HPLC Conditions:
Column: Purospher Star RP C18 (250×4.0, 5 µm)
Eluent A: 0.01% formic acid in water
Eluent B: Acetonitrile
Flow: 0.8 ml/min
Column temperature: 30° C.
Injection volume: 4 µl
Detection: UV 210 nm (or 254 nm)
The results of these experiments are given in table 8.

TABLE 8

Conversion of phenoxyacetone to 1-phenoxy-2-propylamine catalysed by the (R)-transaminase XP_001209325 [SEQ ID No. 1]

| Donor | Conversion ketone [%] | 1-Phenoxy-2-propylamine [mol/l] | [wt %] |
|---|---|---|---|
| 2-butylamine | 64 | 0.064 | 1.0 |
| MBA | 32 | 0.032 | 0.5 |
| isopropylamine | 31 | 0.031 | 0.5 |

2-butylamine and MBA are effectively better amino donors than isopropylamine for the (R)-selective transaminase XP_001209325 [SEQ ID No.1] as the actual concentration of (R)-2-butylamine and (R)-MBA are 0.25 M compared to 0.5 M of the achiral amino donor isopropylamine. Thus comparable or even better conversions are obtained with the amino donors 2-butylamine and MBA, respectively, at relatively lower amino donor concentrations compared to the amino donor isopropylamine. Even high product concentrations of 1.0 wt % were obtained (with 2-butylamine as amino donor).

Example 9—Transamination of Benzylacetone in the Presence of a Second Organic Solvent Phase Cell-free extract with heterologously in *E. coli* expressed (R)-transaminase XP_001209325 [SEQ ID No.1] (2 U/ml) as produced and assayed as in EXAMPLE 3 and EXAMPLE 6 was incubated with 0.1 M of ketone substrate benzylacetone and 0.25 M of the amino donor (RS)-α-methylbenzylamine in 50 mM $KP_i$ buffer pH 7.5 containing 0.5 mM PLP at 30° C. for 24 h. The reactions were carried out in the presence and absence of 15% (v/v) of the non water-miscible organic solvent cyclohexane. The amount of 4-phenyl-2-propylamine formed and the enantiomeric excess (e.e.) of the reactions were measured by HPLC analysis as described in EXAMPLE 8. The determination of enantiomeric excesses was performed by HPLC analysis on a chiral stationary phase as follows:

20 µl of the reaction mixture was mixed with 50 µl of Marfey's reagent solution (1% w/v N-α-[2,4-dinitrophenyl-5-fluorophenyl]-L-alanine amide in acetone) and 10 µl saturated solution of $NaHCO_3$. After incubation of the mixture at 40° C. for 1 hour 10 µl 2 N HCl and 920 µl acetonitrile were added and the sample was centrifuged for 5 min prior to injection.
HPLC Conditions:
Column: Purospher Star RP C18 (250×4.0, 5 µm)
Eluent A: 0.01% formic acid in water
Eluent B: Acetonitrile
Flow: 1 ml/min
Column temperature: 30° C.
Injection volume: 2 µl
Detection: UV 338.1 nm
Isocratic 50/50 eluent A/eluent B
The results of these experiments are given in table 9.

TABLE 9

Conversion and e.e. of (R)-4-phenyl-2-propylamine formed by XP_001209325 [SEQ ID No. 1] from benzylacetone in the presence and absence of the non water-miscible organic solvent cyclohexane

| Condition | Conversion to 4-phenyl-2-propylamine [%] | e.e. (R)-4-phenyl-2-propylamine [%] |
|---|---|---|
| no organic solvent | 32 | >99.9 |
| 15% (v/v) cyclohexane | 22 | >99.9 |

These results show that the (R)-selective transaminase XP_001209325 [SEQ ID No.1] well tolerates the presence of the non water-miscible organic solvent cyclohexane and that its presence does not affect the enantioselectivity of the enzyme reaction.

Example 10—Recombinant (R)-Transaminases from Genomes of the Enriched Microorganisms From the six strains, which were enriched on selective media for their (R)-selective transaminase activity (EXAMPLE 1 and 2), *Rahnella aquatilis* 3Kb, *Microbacterium ginsengisoli* 1A1 DSM 23784, *Sinorhizobium morelense* 3H1 DSM 23794, *Curtobacterium pusillum* 5BaB DSM 23787, *Mycobacterium frederiksbergense* 1Ia DSM 23798, and *Achromobacter spanius* 61 DSM 23791 genomic DNA was isolated with the Easy-DNA kit (Invitrogen) according to the manufacturer's manual and finally eluted with TE buffer. The quality of the DNA was checked photometrically as well as by digest with Bsp143I or BamHI (Fermentas, St. Leon-Rot) followed by agarose gel electrophoresis. The thus isolated genomic DNA samples from *Rahnella aquatilis* 3Kb, *Microbacterium ginsengisoli* 1A1 DSM 23784, *Curtobacterium pusillum* 5BaB DSM 23787, *Achromobacter spanius* 61 DSM 23791, and *Microbacterium ginsengisoli* 1A1 DSM 23784 were use for genome sequencing.

These genomic sequences were uploaded to a server and BLAST searches were conducted against the known (R)-transaminase sequences SEQ ID No.1 and against hits found in one of the genomes. Several hits with different degree of similarity were identified and chosen for subsequent NdeI/HindIII cloning into pMS470Δ8 (Balzer et al., *Nucleic Acids Research*, 1992, 20 (8): 1851-1858) and expression in *E. coli*. Three of the genes could not be amplified by PCR and one contained NdeI and HindIII in the native sequence and thus Asp-TA1, Cpu-TA1, Cpu-TA3 Raq-TA2 and Mgi-TA1 were ordered codon optimised for the expression in *E. coli* from Geneart/life technologies (Regensburg, Germany).

TABLE 10

BLAST search identity to the (R)-transaminase of SEQ ID No. 1

| protein | Source organism | SEQ ID No. | Sequence identity to SEQ ID No. 1 |
|---|---|---|---|
| Cpu-TA1 | *Curtobacterium pusillum* 5BaB DSM 23787 | 30 | 26% |
| Cpu-TA2 | *Curtobacterium pusillum* 5BaB DSM 23787 | 33 | 32% |
| Cpu-TA3 | *Curtobacterium pusillum* 5BaB DSM 23787 | 35 | 27% |
| Raq-TA2 | *Rahnella aquatilis* 3Kb | 38 | 27% |
| Raq-TA3 | *Rahnella aquatilis* 3Kb | 40 | 22% |
| Asp-TA1 | *Achromobacter spanius* 6I DSM 23791 | 43 | 27% |
| Mgi-TA1 | *Microbacterium ginsengisoli* 1A1 DSM 23784 | 46 | 24% |

The 6 target genes were expressed in *E. coli* TOP1 OF' in LB medium supplemented with Ampicillin (100 µg/ml) after induction with 0.5 mM IPTG at 25° C. o/n. As a control served an *E. coli* TOP10F' culture containing a pMS470 vector without an inserted transaminase gene. The cells were harvested and lysed by sonication in 50 mM $KP_i$ buffer pH 7.5 containing 0.1 mM PLP and centrifuged. The lysates were concentrated using VivaSpin concentrators (Sartorius, Vienna, Austria). The protein concentrations of the lysates were determined by Bradford protein assay.

All lysates were tested in transamination reactions using the corresponding bulky amines on which the donor microorganism had been enriched on as a donor and pyruvate as an acceptor. Five times excess of a racemic or enantiopure amine (50 mM) was used over pyruvic acid (10 mM) in 50 mM $KP_i$ buffer pH 7.5 containing 0.1 mM PLP at 30° C. for 24 h. In the reactions with Mgi-TA1 10 mM of pyruvic acid and 10 mM of amino donor MBA or 1-aminotetralin, respectively, were applied in 50 mM KP; buffer pH 7.5 containing 0.1 mM PLP at 30° C. for 19 h. The formation of corresponding ketone was detected on HPLC as described in EXAMPLES 8 and 9. The selectivity of new transaminases was determined by formation of L- or D-alanine and the reactivity of different enantiomers of the respective amines. The new transaminases Cpu-TA1 [SEQ ID No.30], Cpu-TA2 [SEQ ID No.33], Cpu-TA3 [SEQ ID No.35], Raq-TA2 [SEQ ID No.38], Raq-TA3 [SEQ ID No.40], Asp-TA1 [SEQ ID No.43], and Mgi-TA1 [SEQ ID No. 46] showed (R)-selectivity (table 11). Cpu-TA2 was also tested with MBA and alanine as amino donors and phenoxyacetone and acetophenone as acceptor ketones, respectively. The amine products of these two reactions were enantiomerically enriched (R)-1-phenoxy-2-propylamine and (R)-MBA, respectively (table 11).

These results show that the new transaminases Cpu-TA1 [SEQ ID No. 30], Cpu-TA2 [SEQ ID No. 33], Cpu-TA3 [SEQ ID No. 35], Raq-TA2 [SEQ ID No. 38], Raq-TA3 [SEQ ID No. 40], Asp-TA1 [SEQ ID No. 43] and Mgi-TA1 [SEQ ID No. 46] are indeed (R)-selective transaminases.

TABLE 11

Transamination reactions catalyzed by new transaminases and their selectivities.

| Enzyme | Amino donor | Acceptor ketone | Conversion ketone [%] | Product | Selectivity product |
|---|---|---|---|---|---|
| Asp-TA1 | MBA | Pyruvate | 1.5 | alanine | (R) (=D) |
| Cpu-TA1 | 1-aminoindan | Pyruvate | 89.0 | alanine | (R) (=D) |
|  | (R)-1-aminoindan | Pyruvate | 96.7 | alanine | (R) (=D) |
| Cpu-TA2 | 1-aminoindan | Pyruvate | 15.4 | alanine | (R) (=D) |
|  | MBA | Phenoxyacetone | 1.1 | 1-phenoxy-2-propylamine | (R) |
|  | alanine | Acetophenone | 1.3 | MBA | (R) |
| Cpu-TA3 | 1-aminoindan | Pyruvate | 26.6 | alanine | (R) (=D) |
|  | (R)-1-aminoindan | Pyruvate | 17.4 | alanine | (R) (=D) |
| Raq-TA2 | 1-aminotetralin | Pyruvate | 19.2 | alanine | (R) (=D) |
|  | (R)-1-aminotetralin | Pyruvate | 17.9 | alanine | (R) (=D) |
| Raq-TA3 | 1-aminotetralin | Pyruvate | 17.0 | alanine | (R) (=D) |
|  | (R)-1-aminotetralin | Pyruvate | 62.5 | alanine | (R) (=D) |
|  | (S)-1-aminotetralin | Pyruvate | 6.5 | alanine | (R) (=D) |
| Mgi-TA1 | MBA | Pyruvate | 21.0 | alanine | (R) (=D) |
|  | 1-aminotetralin | Pyruvate | 34.0 | alanine | (R) (=D) |
| pMS vector w/o transaminase insert (−control) | MBA | Pyruvate | 0.6 |  |  |

Example 11—Synthesis of 4-Phenyl-2-Propylamine from Benzylacetone and (R)-α-Methylbenzylamine in the Presence of Non Water-Miscible Organic Solvent Cell-free extract with heterologously in *E. coli* expressed (R)-transaminase XP_001209325 [SEQ ID No. 1] as produced and assayed as in EXAMPLE 3 and EXAMPLE 6 was incubated with 0.08 M of the amino donor (R)-α-methylbenzylamine (MBA) and a 1.5 fold excess of the ketone substrate benzylacetone (0.12 M) in 50 mM $KP_i$ buffer pH 7.5 containing 0.1 mM PLP at 28° C. for 20 h. The reactions were carried out in the presence and absence of 10% (v/v) of the non water-miscible organic solvent cyclohexane. The amount of 4-phenyl-2-propylamine formed was measured by HPLC analysis as described in the general part.

Without addition of cyclohexanone 42.8 mM 4-phenyl-2-propylamine was formed, while with 10% (v/v) cyclohexanone an even higher concentration of 44.3 mM 4-phenyl-2-propylamine was formed from benzylacetone with (R)-MBA as amino donor.

Example 12—Enzymatic Synthesis of (R)-Sec-Butylamine from (R)-α-Methylbenzylamine The transaminases XP_001209325 [SEQ ID No. 1], XP_002564064 [SEQ ID No. 3], EEU44019 [SEQ ID No. 5], XP_001402221 [SEQ ID No. 7], YP_761201 [SEQ ID No. 9], YP_838940 [SEQ ID No. 11], YP_955297 [SEQ ID No. 13], EDI73966 [SEQ ID No. 15], NP_085750 [SEQ ID No. 17], EDH25885 [SEQ ID No. 19], EBP64591 [SEQ ID No. 21], and ECU93014 [SEQ ID No. 23] as well as ABN35871 and AAN21261 were produced as described in EXAMPLE 3. Cell-free extracts containing the heterologously expressed transaminases were reacted with 25 mM butanone and 50 mM (R)-α-methylbenzylamine at 28° C. with shaking at 400 rpm for 24 h in 100 mM KR buffer pH 7.5 containing 0.1 mM PLP in a total volume of 1 ml. After 20 h the reactions were quenched by addition of a 100 μl sample of each reaction to 50 μl of 2-hexanone solution and 850 μl acetonitrile and centrifugation for 10 min at 3000×g. The samples were analysed by GC-FID detection on a CpSil 8 for amines column (30 m×0.25×0.5) using commercial MBA, acetophenone, butanone and sec-butylamine as references (Sigma-Aldrich). The results are summarized in table 12.

TABLE 12

Concentration of sec-butylamine in mM formed from (R)-MBA and butanone after 24 h using the respective transaminases

| Transaminase | sec-Butylamine [mM] |
| --- | --- |
| ABN35871 | 0.99 |
| AAN21261 | 7.96 |
| YP_955297 | 1.52 |

TABLE 12-continued

Concentration of sec-butylamine in mM formed from (R)-MBA and butanone after 24 h using the respective transaminases

| Transaminase | sec-Butylamine [mM] |
| --- | --- |
| YP_838940 | 0.45 |
| XP_001209325 | 15.74 |
| EBP64591 | 0.06 |
| EDI73966 | 0.42 |
| XP_002564064 b | 0.63 |
| YP_761201 | 0.42 |
| EEU44019 b | 0.23 |
| XP_001402221 | 0.71 |
| NP_085750 b | 0.08 |

Example 13—Enzymatic Synthesis of (R)-3,3-Dimethyl-2-Butylamine from (R)-MBA and 3,3-Dimethyl-Butanone Cell-free extracts containing the heterologously expressed transaminases XP_001209325 [SEQ ID No. 1], YP_955297 [SEQ ID No. 13], ABN35871 and AAN21261 produced as described in EXAMPLE 3 were reacted with 25 mM 3,3-dimethyl-butanone and 50 mM (R)-α-methylbenzylamine at 28° C. with shaking at 400 rpm for 24 h in 100 mM KR buffer pH 7.5 containing 0.1 mM PLP in a total volume of 1 ml. After 20 h the reactions were quenched by addition of a 100 μl sample of each reaction to 50 μl of 2-hexanone solution and 850 μl acetonitrile and centrifugation for 10 min at 3000×g. The samples were analysed by GC-FID detection on a CpSil 8 for amines column (30 m×0.25×0.5) using commercial MBA, acetophenone, butanone and sec-butylamine as references (Sigma-Aldrich). The results are summarized in table 13.

TABLE 13

Concentration of sec-butylamine in mM formed from (R)-MBA and 3,3-dimethyl-butanone after 24 h using the respective transaminases

| Transaminase | 3,3-dimethyl-2-butylamine [mM] |
| --- | --- |
| ABN35871 | 0.00 |
| AAN21261 | 3.28 |
| YP_955297 | 0.34 |
| XP_001209325 | 1.49 |

The invention claimed is:

1. A process for the enzymatic synthesis of an enantiomerically enriched (R)-amine of general formula [1][c]

[1][c]

from the corresponding ketone of the general formula [1][a]

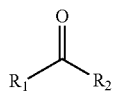

[1][a]

and a suitable amino donor, wherein $R_1$ and $R_2$ are different and are independently linear or branched aliphatic, aromatic, hetero-aromatic or form a cyclic structure, by using a transaminase selected from the group consisting of a protein having at least 90% identity to the amino acid sequence of SEQ ID No. 1, wherein the transaminase has a transaminase enantioselectivity value (TEV) of at least approximately 5.

2. A process according to claim 1, wherein $R_1$ and $R_2$ are different and $R_1$ and $R_2$ independently contain 1 to 30 carbon atoms and $R_1$ and $R_2$ are independently substituted or unsubstituted aliphatic; substituted or unsubstituted branched aliphatic; substituted or unsubstituted cyclic aliphatic; substituted or unsubstituted heterocyclic aliphatic, containing at least one oxygen, sulfur or nitrogen atom; substituted or unsubstituted aromatic; substituted or unsubstituted hetero-aromatic containing at least one sulfur or nitrogen atom; or together form a substituted or unsubstituted cyclic structure or heterocyclic structure, containing at least one oxygen, sulfur or nitrogen atom; wherein the substituents are selected from but not limited to the group consisting of a halogen atom, an alkyl group having 1 to 6 carbon atoms, hydroxyl group, methoxy group, monofluoromethyl, difluoromethyl and trifluoromethyl group.

3. A process according to claim 1, wherein the final concentration of the enantiomerically enriched (R)-amine product lies between 1 and 50 weight % of the reaction mixture.

4. A process according to claim 1, wherein the amino donor is α-methylbenzylamine.

5. A process according to claim 1, wherein the amino donor is sec-butylamine.

6. A process according to claim 1, wherein the final concentration of the enantiomerically enriched (R)-amine product lies between 5 and 35 weight % of the reaction mixture.

7. A process according to claim 1, wherein the reaction mixture comprises an aqueous phase and second organic phase.

8. A process according to claim 1, wherein the reaction mixture comprises an aqueous phase and second organic phase and the volumetric ratio of water:organic phase is between 100 and 0.01.

9. A process according to claim 1, wherein the reaction mixture comprises an aqueous phase and second organic phase and the volumetric ratio of water:organic phase is between 20 and 0.1.

10. A process according to claim 1, wherein the reaction mixture comprises an aqueous phase and second organic phase and the volumetric ratio of water:organic phase is between 20 and 1.

11. A process according to claim 1, wherein the TEV is at least approximately 10.

12. A process according to claim 1, wherein the TEV is at least approximately 15.

* * * * *

UNITED STATES PATENT AND TRADEMARK OFFICE
CERTIFICATE OF CORRECTION

PATENT NO. : 10,023,886 B2
APPLICATION NO. : 14/885622
DATED : July 17, 2018
INVENTOR(S) : Schurmann et al.

It is certified that error appears in the above-identified patent and that said Letters Patent is hereby corrected as shown below:

In the Specification

At Column 6/Line 9: "TEV 10" should read --TEV$\geq$10--

At Column 6/Line 63: "KR" should read --$KP_i$--

At Column 7/Line 41: "(KR)" should read --$(KP_i)$--

At Column 11/Line 17: "(KR)" should read --$(KP_i)$--

At Column 11/Line 20: "(KR)" should read --$(KP_i)$--

At Column 19/Line 55: "2 Da," should read --2Da,--

At Column 24/Line 28: "TEV 5" should read --TEV$\geq$5--

At Column 27/Line 32: "TOP1 OF$^1$" should read --TOP10F$^1$--

At Column 28/Line 8: "KP;" should read --$KP_i$--

At Column 29/Line 27: "KR" should read --$KP_i$--

At Column 30/Line 26: "KR" should read --$KP_i$--

Signed and Sealed this
Thirtieth Day of July, 2019

Andrei Iancu
*Director of the United States Patent and Trademark Office*

SEQUENCE LISTING

```
<160> NUMBER OF SEQ ID NOS: 46

<210> SEQ ID NO 1
<211> LENGTH: 325
<212> TYPE: PRT
<213> ORGANISM: Aspergillus terreus

<400> SEQUENCE: 1

Met Ala Ser Met Asp Lys Val Phe Ala Gly Tyr Ala Ala Arg Gln Ala
1               5                   10                  15

Ile Leu Glu Ser Thr Glu Thr Thr Asn Pro Phe Ala Lys Gly Ile Ala
            20                  25                  30

Trp Val Glu Gly Glu Leu Val Pro Leu Ala Glu Ala Arg Ile Pro Leu
        35                  40                  45
```

```
Leu Asp Gln Gly Phe Met His Ser Asp Leu Thr Tyr Asp Val Pro Ser
 50                  55                  60

Val Trp Asp Gly Arg Phe Phe Arg Leu Asp Asp His Ile Thr Arg Leu
 65                  70                  75                  80

Glu Ala Ser Cys Thr Lys Leu Arg Leu Arg Leu Pro Leu Pro Arg Asp
                 85                  90                  95

Gln Val Lys Gln Ile Leu Val Glu Met Val Ala Lys Ser Gly Ile Arg
                100                 105                 110

Asp Ala Phe Val Glu Leu Ile Val Thr Arg Gly Leu Lys Gly Val Arg
                115                 120                 125

Gly Thr Arg Pro Glu Asp Ile Val Asn Asn Leu Tyr Met Phe Val Gln
130                 135                 140

Pro Tyr Val Trp Val Met Glu Pro Asp Met Gln Arg Val Gly Gly Ser
145                 150                 155                 160

Ala Val Val Ala Arg Thr Val Arg Arg Val Pro Pro Gly Ala Ile Asp
                165                 170                 175

Pro Thr Val Lys Asn Leu Gln Trp Gly Asp Leu Val Arg Gly Met Phe
                180                 185                 190

Glu Ala Ala Asp Arg Gly Ala Thr Tyr Pro Phe Leu Thr Asp Gly Asp
                195                 200                 205

Ala His Leu Thr Glu Gly Ser Gly Phe Asn Ile Val Leu Val Lys Asp
210                 215                 220

Gly Val Leu Tyr Thr Pro Asp Arg Gly Val Leu Gln Gly Val Thr Arg
225                 230                 235                 240

Lys Ser Val Ile Asn Ala Ala Glu Ala Phe Gly Ile Glu Val Arg Val
                245                 250                 255

Glu Phe Val Pro Val Glu Leu Ala Tyr Arg Cys Asp Glu Ile Phe Met
                260                 265                 270

Cys Thr Thr Ala Gly Gly Ile Met Pro Ile Thr Thr Leu Asp Gly Met
                275                 280                 285

Pro Val Asn Gly Gly Gln Ile Gly Pro Ile Thr Lys Lys Ile Trp Asp
                290                 295                 300

Gly Tyr Trp Ala Met His Tyr Asp Ala Ala Tyr Ser Phe Glu Ile Asp
305                 310                 315                 320

Tyr Asn Glu Arg Asn
                325
```

<210> SEQ ID NO 2
<211> LENGTH: 978
<212> TYPE: DNA
<213> ORGANISM: artificial sequence
<220> FEATURE:
<223> OTHER INFORMATION: Codon optimized sequence coding for SEQ ID 1

<400> SEQUENCE: 2

```
atggcgtcta tggacaaagt attcgctggt tacgctgcac gtcaggctat cctggaatcc     60
actgaaacta ccaacccgtt cgctaaaggt atcgcatggg ttgaaggtga actggtaccg    120
ctggctgaag cgcgtatccc gctgctggat cagggcttca tgcactctga cctgacttac    180
gacgttccgt ctgtatggga cggtcgtttc ttccgtctgg atgaccacat cactcgtctg    240
gaagcgtcct gcaccaaact gcgtctgcgt ctgccgctgc cgcgcgacca ggttaagcag    300
atcctggttg aaatggttgc taaatctggt atccgtgacg cattcgttga gctgatcgtt    360
actcgcggtc tgaaaggcgt tcgtggtact cgtccggaag atatcgttaa caacctgtac    420
atgttcgttc agccgtacgt atgggtaatg gaaccggata tgcagcgcgt tggtggttct    480
```

```
gctgttgttg cgcgtaccgt tcgtcgcgtt ccgccaggtg caatcgaccc gaccgttaaa      540
aacctgcagt ggggcgacct ggttcgtggt atgttcgaag cagctgaccg cggtgcaact      600
tacccgttcc tgactgacgg tgacgcacac ctgactgaag ttctggctt caacatcgtt       660 ctggttaaag acggcgtact gtacactccg gaccgcggtg ttctgcaggg cgtaactcgt      720
aagtctgtta tcaacgctgc tgaagcgttc ggtatcgaag ttcgcgttga gttcgttccg      780
gttgaactgg cttaccgctg cgacgaaatc ttcatgtgta ctactgcagg tggtatcatg      840
ccaatcacca ctctggacgg tatgccggtt aacggtggtc agatcggtcc gatcaccaag      900
aaaatctggg acggttactg ggcgatgcac tacgacgctg cttactcctt cgaaatcgac      960
tacaacgaac gtaattaa                                                     978
```

<210> SEQ ID NO 3
<211> LENGTH: 319
<212> TYPE: PRT
<213> ORGANISM: Penicillium chrysogenum

<400> SEQUENCE: 3

```
Met Ala Thr Met Glu Lys Ile Phe Ala Ala Tyr His Glu Arg Gln Lys
1               5                   10                  15

Leu Leu Ala Ala Asn Thr His Pro Phe Ala Lys Gly Val Ala Trp Val
            20                  25                  30

Glu Gly Glu Leu Thr Pro Leu His Glu Ala Arg Ile Pro Ile Leu Asp
        35                  40                  45

Gln Gly Phe Met His Ser Asp Leu Thr Tyr Asp Val Pro Ser Val Trp
    50                  55                  60

Asp Gly Arg Phe Phe Arg Leu Asp Asp His Ile Thr Arg Leu Glu Ala
65                  70                  75                  80

Ser Cys Thr Lys Leu Arg Met Lys Leu Pro Leu Pro Arg Asp Glu Val
                85                  90                  95

Lys Gln Ile Leu Val Asp Met Val Ala Lys Ser Gly Ile Arg Asp Ala
            100                 105                 110

Phe Val Glu Ile Ile Val Thr Arg Gly Leu Lys Gly Val Arg Gly Ser
        115                 120                 125

Arg Pro Glu Asp Ile Val Asn Arg Ile Tyr Met Phe Ile Gln Pro Tyr
    130                 135                 140

Val Trp Cys Met Glu Pro Glu Val Gln Pro Val Gly Gly Ser Ala Ile
145                 150                 155                 160

Ile Ala Arg Thr Val Arg Arg Val Pro Pro Gly Cys Ile Asp Pro Thr
                165                 170                 175

Val Lys Asn Leu Gln Trp Gly Asp Leu Val Arg Gly Leu Phe Glu Ala
            180                 185                 190

Ser Asp Arg Gly Ala Glu Tyr Pro Phe Leu Thr Asp Gly Asp Thr Asn
        195                 200                 205

Leu Thr Glu Gly Ser Gly Phe Asn Ile Val Leu Val Lys Asp Asn Ile
    210                 215                 220

Leu Tyr Thr Pro Ala Arg Gly Val Leu Glu Gly Val Thr Arg Lys Ser
225                 230                 235                 240

Val Ile Asp Val Ala Arg Ala Ser Gly Phe Asp Ile Lys Val Glu Leu
                245                 250                 255

Val Pro Val Gln Met Ala Tyr Asp Ala Asp Glu Ile Phe Met Cys Thr
            260                 265                 270

Thr Ala Gly Gly Ile Met Pro Ile Thr Ser Leu Asp Gly Lys Pro Val
        275                 280                 285
```

```
Asn Asp Gly Lys Val Gly Ser Val Thr Lys Lys Ile Trp Asp Gly Tyr
    290                 295                 300

Trp Ala Ile His Tyr Asp Pro Ala Tyr Ser Phe Glu Ile Ala Tyr
305                 310                 315
```

<210> SEQ ID NO 4
<211> LENGTH: 960
<212> TYPE: DNA
<213> ORGANISM: artificial sequence
<220> FEATURE:
<223> OTHER INFORMATION: codon optimized sequence coding for SEQ ID 3

<400> SEQUENCE: 4

```
atggcgacca tggaaaaaat cttcgctgct taccacgagc gtcagaaact gctggcagct    60
aacactcacc cgttcgctaa aggcgtagca tgggttgaag gtgaactgac tccgctgcac   120
gaagcgcgta tcccgattct ggatcagggc ttcatgcact ctgacctgac ttacgacgtt   180
ccgtctgtat gggacggtcg tttcttccgt ctggatgacc acatcactcg tctggaagcg   240
tcctgcacca aactgcgtat gaagctgccg ctgccgcgcg acgaagttaa gcagatcctg   300
gttgatatgg ttgctaaatc tggtatccgt gacgcattcg ttgaaatcat cgttactcgc   360
ggtctgaaag cgttcgtgg ttcccgtccg gaagatatcg ttaaccgtat ctacatgttc   420
atccagccgt acgtatggtg catggaaccg gaagttcagc cggtaggtgg ttctgctatc   480
atcgcgcgta ccgttcgtcg cgttccgcca ggttgcatcg acccgaccgt taaaaacctg   540
cagtggggcg aactggttcg tggtctgttc gaagcgtctg accgcggtgc agaatacccg   600
ttcctgactg acggtgacac caacctgact gaaggttctg gcttcaacat cgttctggtt   660
aaagacaaca tcctgtacac tccggcacgt ggtgttctgg aaggcgtaac tcgtaagtct   720
gttatcgacg ttgctcgcgc ttctggcttc gacatcaaag ttgagctggt tccggtacag   780
atggcttacg acgctgacga atcttcatg tgtactactg caggtggtat catgccaatc   840
acttctctgg acggtaagcc ggttaacgac ggtaaagttg ttctgttac caagaaaatc   900
tgggacggtt actgggcaat ccactacgac ccggcttact ccttcgaaat cgcttattaa   960
```

<210> SEQ ID NO 5
<211> LENGTH: 320
<212> TYPE: PRT
<213> ORGANISM: Nectria haematococca

<400> SEQUENCE: 5

```
Met Ala Thr Met Asp Lys Val Phe Ala Gly Tyr Ala Glu Arg Gln Ala
1               5                   10                  15

Val Leu Glu Ala Ser Lys Asn Pro Leu Ala Lys Gly Val Ala Trp Ile
            20                  25                  30

Gln Gly Glu Leu Val Pro Leu His Glu Ala Arg Ile Pro Leu Leu Asp
        35                  40                  45

Gln Gly Phe Met His Ser Asp Leu Thr Tyr Asp Val Pro Ser Val Trp
    50                  55                  60

Asp Gly Arg Phe Phe Arg Leu Glu Asp His Leu Asn Arg Leu Glu Ala
65                  70                  75                  80

Ser Cys Lys Lys Met Arg Leu Arg Met Pro Leu Pro Arg Glu Glu Val
                85                  90                  95

Ile Lys Thr Leu Val Asp Met Val Ala Lys Ser Gly Ile Arg Asp Ala
            100                 105                 110

Phe Val Glu Leu Ile Val Thr Arg Gly Leu Thr Gly Val Arg Gly Ala
        115                 120                 125
```

Lys Pro Glu Leu Leu Asn Asn Asn Leu Tyr Met Phe Ile Gln Pro
            130                 135                 140

Tyr Val Trp Val Met Asp Pro Asp Val Gln Tyr Thr Gly Gly Arg Ala
145                 150                 155                 160

Ile Val Ala Arg Thr Val Arg Arg Val Pro Pro Gly Ser Ile Asp Pro
                165                 170                 175

Thr Ile Lys Asn Leu Gln Trp Gly Asp Leu Val Arg Gly Leu Phe Glu
            180                 185                 190

Ala Asn Asp Arg Gly Ala Thr Tyr Pro Phe Leu Thr Asp Gly Asp Ala
        195                 200                 205

Asn Leu Thr Glu Gly Ser Gly Phe Asn Val Val Leu Ile Lys Asp Gly
210                 215                 220

Val Leu Tyr Thr Pro Asp Arg Gly Val Leu Gln Gly Ile Thr Arg Lys
225                 230                 235                 240

Ser Val Ile Asp Ala Ala Arg Ser Cys Gly Tyr Glu Ile Arg Val Glu
                245                 250                 255

His Val Pro Ile Glu Ala Thr Tyr Gln Ala Asp Glu Ile Leu Met Cys
            260                 265                 270

Thr Thr Ala Gly Gly Ile Met Pro Ile Thr Thr Leu Asp Asp Lys Pro
        275                 280                 285

Val Lys Asp Gly Lys Val Gly Pro Ile Thr Lys Ala Ile Trp Asp Arg
290                 295                 300

Tyr Trp Ala Met His Trp Glu Asp Glu Phe Ser Phe Lys Ile Asn Tyr
305                 310                 315                 320

<210> SEQ ID NO 6
<211> LENGTH: 963
<212> TYPE: DNA
<213> ORGANISM: artificial sequence
<220> FEATURE:
<223> OTHER INFORMATION: Codon optimized sequence coding for SEQ ID 5

<400> SEQUENCE: 6
atggcaacca tggacaaagt attcgctggt tacgctgaac gtcaggctgt tctggaagcg      60
tctaaaaacc cgctggcgaa aggcgttgca tggattcagg cgaactggt tccgctgcac      120 gaagcgcgta tcccgctgct ggatcagggc ttcatgcact ctgacctgac ttacgacgtt      180
ccgtctgtat gggacggtcg tttcttccgt ctgaagatc acctgaaccg tctggaagcg      240
tcctgcaaga aaatgcgtct gcgtatgccg ctgccgcgtg aagaagttat caaaactctg      300
gttgatatgg ttgctaaatc tggtatccgt gacgcattcg ttgaactgat cgttactcgc      360
ggtctgactg gcgttcgtgg tgcgaagccg aagagctgc tgaacaacaa cctgtacatg      420
ttcatccagc cgtacgtatg ggtaatggac ccggacgttc agtacaccgg tggtcgtgct      480
atcgttgctc gtaccgttcg tcgcgtaccg ccaggttcta tcgacccgac tatcaaaaac      540
ctgcagtggg gcgacctggt tcgtggtctg ttcgaagcta acgaccgcgg tgcaacttac      600
ccgttcctga ctgacggtga cgctaacctg actgaaggtt ctggcttcaa cgttgttctg      660
atcaaagacg gcgtactgta cactccggac cgcggtgttc tgcagggtat cactcgtaag      720
tctgttatcg acgctgcacg ttcctgcggt tacgaaatcc gcgttgaaca cgttccgatc      780
gaagcaactt accaggctga cgaaatcctg atgtgtacta ctgctggcgg tatcatgcca      840
atcaccactc tggatgacaa gccggttaaa gacggtaaag ttggtccgat caccaaagct      900
atctgggacc gttactgggc aatgcactgg gaagacgagt tctctttcaa gatcaactac      960
taa                                                                    963

<210> SEQ ID NO 7
<211> LENGTH: 327
<212> TYPE: PRT
<213> ORGANISM: Aspergillus niger

<400> SEQUENCE: 7

```
Met Ala Ser Met Asn Gln Val Leu Thr Glu Tyr Ala Thr Arg Arg Ala
1               5                   10                  15

Thr Leu Glu Ala Ser Lys Asn Pro Tyr Ala Lys Gly Ile Ala Trp Val
            20                  25                  30

Glu Gly Gln Leu Val Pro Leu Arg Glu Ala Arg Ile Pro Leu Ile Asp
        35                  40                  45

Gln Gly Phe Leu Arg Ser Asp Leu Thr Tyr Asp Val Ile Ser Val Trp
    50                  55                  60

Asp Gly Trp Phe Phe Arg Leu Asp Asp His Leu Ser Arg Leu Glu Leu
65                  70                  75                  80

Ala Cys Ala Lys Ser Arg Leu Lys Leu Pro Ile Ser Arg Asp Glu Val
                85                  90                  95

Lys Gln Ser Leu Val Arg Met Val Ala Gln Ser Gly Ile Arg Asp Ala
            100                 105                 110

Tyr Val Ala Leu Ile Val Thr Arg Gly Leu Gln Ser Val Arg Gly Ala
        115                 120                 125

Lys Pro Glu Asp Leu Val Asn Asn Leu Tyr Met Phe Val Gln Pro Tyr
    130                 135                 140

Val Trp Val Met Glu Pro Glu Val Gln Arg Val Gly Ser Ala Val
145                 150                 155                 160

Val Thr Arg Thr Val Arg Arg Val Pro Pro Gly Ala Ile Tyr Pro Thr
                165                 170                 175

Val Lys Asn Leu Gln Trp Gly Asp Leu Thr Arg Gly Met Leu Glu Ala
            180                 185                 190

Ala Asp Arg Gly Ser Met Tyr Pro Phe Leu Thr Asp Gly Asp Gly His
        195                 200                 205

Leu Thr Glu Gly Ser Gly Tyr Asn Ile Val Leu Ile Lys Ala Gly Ala
    210                 215                 220

Ile Tyr Thr Pro Asp Arg Gly Val Leu His Gly Val Thr Arg Thr Ser
225                 230                 235                 240

Val Ile Asp Val Ala Arg Ala Cys Gly Ile Gln Val His Leu Glu Ala
                245                 250                 255

Val Pro Val Glu Leu Val Tyr Gln Cys Asp Glu Ile Phe Met Cys Thr
            260                 265                 270

Thr Ala Gly Gly Ile Met Pro Ile Thr Glu Leu Asp Gly Lys Pro Val
        275                 280                 285

Asn Gly Gly Arg Ile Gly Pro Ile Thr Lys Lys Ile Trp Asp Gly Tyr
    290                 295                 300

Trp Gly Met His Tyr Asp Pro Ala Tyr Ser Phe Ala Val Ser Tyr Asp
305                 310                 315                 320

Asp Gly Ser Lys Ala Lys Leu
                325
```

<210> SEQ ID NO 8
<211> LENGTH: 984
<212> TYPE: DNA
<213> ORGANISM: Artificial sequence
<220> FEATURE:
<223> OTHER INFORMATION: Codon optimized sequence coding for SEQ ID 7

<400> SEQUENCE: 8

-continued

```
atggcttcta tgaaccaggt tctgactgaa tacgcaactc gtcgtgcaac tctggaagcg      60
tctaaaaacc cgtacgctaa aggtatcgca tgggttgaag gtcagctggt accgctgcgt     120
gaagcgcgta tcccgctgat cgaccagggc ttcctgcgtt ctgacctgac ttacgacgtt     180
atctccgtat gggacggctg gttcttccgt ctggatgacc acctgtctcg cctggaactg     240
gcatgtgcga atctcgcct gaaactgccg atctcccgtg acgaagttaa cagtctctg      300 gtacgtatgg ttgctcagtc tggtatccgt gacgcttacg ttgctctgat cgttactcgc     360
ggtctgcagt ctgtacgtgg tgcgaagccg aagatctgg ttaacaacct gtacatgttc     420
gttcagccgt acgtatgggt aatggaaccg aagttcagc gcgttggtgg ttctgctgtt     480
gttactcgta ctgttcgtcg cgttccgcca ggtgctatct acccgaccgt taaaaacctg     540
cagtggggcg acctgactcg cggtatgctg aagcagctg accgcggttc tatgtacccg     600
ttcctgactg acggtgacgg tcacctgact gaaggttctg gttacaacat cgttctgatc     660
aaagctggcg caatctacac tccgaccgt ggtgttctgc acggtgttac tcgtacttct     720
gttatcgacg ttgctcgcgc ttgcggtatt caggttcacc tggaagcggt accggttgag     780
ctggtttacc agtgcgacga atcttcatg tgtactactg caggtggtat catgccaatc     840
actgaactgg acggtaaacc ggttaacggt ggtcgtatcg gtccgatcac caagaaaatc     900
tgggacggtt actggggtat gcactacgac ccggcttact ccttcgctgt ttcttacgac     960
gacggttcta aagcgaagtt ataa                                            984
```

<210> SEQ ID NO 9
<211> LENGTH: 321
<212> TYPE: PRT
<213> ORGANISM: Hyphomonas neptunium

<400> SEQUENCE: 9

```
Met Leu Thr Phe Gln Lys Val Leu Thr Gly Phe Gln Thr Arg Ala Asp
1               5                  10                  15

Ala Arg Ala Glu Arg Thr Asp Ala Phe Ala Asp Gly Ile Ala Trp Ile
            20                  25                  30

Glu Asn Glu Phe Val Pro Ile Gly Lys Ala Arg Ile Pro Ile Leu Asp
        35                  40                  45

Gln Gly Phe Leu His Ser Asp Leu Thr Tyr Asp Val Pro Ala Val Trp
    50                  55                  60

Asn Gly Arg Ile Phe Arg Leu Asp Asp His Leu Asp Arg Leu Glu Val
65                  70                  75                  80

Ser Cys Ala Lys Met Arg Leu Pro Leu Pro Ile Ala Arg Pro Glu Leu
                85                  90                  95

Arg Arg Leu Val Met Glu Leu Val Ser Arg Ser Gly Leu Arg Asp Ala
            100                 105                 110

Tyr Val Glu Ile Ile Val Thr Arg Gly Leu Lys Phe Leu Arg Gly Ala
        115                 120                 125

Gln Ala Glu Asp Ile Ile Pro Asn Leu Tyr Leu Met Ala Val Pro Tyr
    130                 135                 140

Val Trp Ile Leu Pro Leu Glu Tyr Gln Asn His Gly Ala Pro Ala Val
145                 150                 155                 160

Val Thr Arg Thr Val Arg Arg Thr Pro Pro Gly Ala Leu Asp Pro Thr
                165                 170                 175

Ile Lys Asn Leu Gln Trp Gly Asp Leu Val Arg Gly Leu Met Glu Ala
            180                 185                 190
```

Gly Asp Arg Asp Ser Phe Phe Pro Ile Leu Pro Asp Gly Asn
            195                 200                 205

Ala Thr Glu Gly Ala Gly Tyr Asn Ile Val Leu Val Arg Asn Gly Glu
    210                 215                 220

Leu His Thr Pro Arg Arg Gly Val Leu Glu Gly Ile Thr Arg Arg Thr
225                 230                 235                 240

Val Leu Glu Ile Ala Ala Ala Arg Gly Leu Lys Thr His Val Thr Glu
                245                 250                 255

Ile Pro Ile Gln Ala Leu Tyr Glu Cys Asp Glu Leu Phe Met Cys Ser
            260                 265                 270

Thr Ala Gly Gly Ile Met Pro Leu Val Leu Leu Asp Gly Asn Ile Val
            275                 280                 285

Gly Asp Gly Thr Val Gly Pro Val Thr Arg Met Ile Trp Glu Ala Tyr
    290                 295                 300

Trp Asp Leu His Asp Asp Pro Gln Leu Ser Glu Pro Val Thr Tyr Ala
305                 310                 315                 320

Pro

<210> SEQ ID NO 10
<211> LENGTH: 966
<212> TYPE: DNA
<213> ORGANISM: Artificial sequence
<220> FEATURE:
<223> OTHER INFORMATION: Codon optimized sequence coding for SEQ ID 9

<400> SEQUENCE: 10
atgctgactt tccagaaagt tctgactggc ttccagactc gcgctgacgc tcgcgctgaa      60
cgtactgacg cattcgctga cggtatcgcc tggatcgaaa cgagttcgt tccgatcggt      120
aaagcgcgta tcccgatcct ggatcagggc ttcctgcact ctgacctgac ttacgacgtt     180
ccggcagtat ggaacggtcg tatcttccgt ctggataccc acctggaccg tctggaagtt    240
tcctgtgcga agatgcgtct gccgctgcca atcgcgcgtc cggaactgcg tcgtctggta    300
atggaactgg tttcccgttc tggtctgcgt gacgcttacg ttgaaatcat cgttactcgc    360
ggtctgaaat cctgcgcgg tgctcaggct gaagatatca tcccgaacct gtacctgatg    420
gctgttccgt acgtatggat tctgccgctg aataccaga ccacggtgc accggctgtt     480
gttactcgta ccgttcgtcg tactccgcca ggtgcgctgg acccgactat caaaaacctg    540
cagtggggcg acctggttcg tggtctgatg gaagctggcg accgtgactc cttcttcccg    600
atcctgccgg acggtgacgg taacgcaact gaaggtgcag gttacaacat cgttctggtt    660
cgtaacggtg aactgcacac tccgcgtcgc ggtgttctgg aaggtatcac tcgtcgtacc    720
gttctggaaa tcgctgctgc tcgcggtctg aaaactcacg ttactgaaat cccgattcag    780
gcgctgtacg agtgcgacga actgttcatg tgctccactg caggtggtat catgccgctg    840
gttctgctgg acggtaacat cgttggtgac ggtactgttg gtccggtaac tcgtatgatc    900
tgggaagcat actgggatct gcacgacgac ccgcagctgt ctgaaccggt aacttacgca    960
ccgtaa                                                                 966

<210> SEQ ID NO 11
<211> LENGTH: 317
<212> TYPE: PRT
<213> ORGANISM: Burkholderia cenocepacia

<400> SEQUENCE: 11

Met Pro Arg Glu Thr Arg Ser Ala His His Gly Ile Pro Ser Val Glu

```
 1               5                  10                 15
Ala Pro Ala Phe Pro Gln Gly Ala Ala Tyr Met Asn Gly Arg Phe Ile
             20                 25                 30

Pro Ile Ala Asp Ala Arg Val Ser Val Leu Asp Trp Gly Phe Leu His
             35                 40                 45

Ser Asp Val Thr Tyr Asp Thr Val His Val Trp Asn Gly Arg Phe Phe
 50                 55                 60

Arg Leu Asp Lys His Ile Glu Arg Phe Arg Ser Leu Ala Arg Leu
 65                 70                 75                 80

Arg Leu Asn Val Pro Leu Thr Asp Asp Ala Leu Arg Asp Ile Leu Val
             85                 90                 95

Glu Cys Val Arg Arg Ser Gly Leu Arg His Ala Tyr Val Glu Met Leu
            100                105                110

Cys Thr Arg Gly Val Ser Pro Thr Phe Ser Arg Asp Pro Arg Asp Ala
            115                120                125

Val Asn Gln Phe Ile Ala Phe Ala Val Pro Tyr Gly Ser Val Ala Asn
            130                135                140

Glu Arg Gln Leu Arg Glu Gly Leu His Leu His Val Ile Asp Asp Val
145                150                155                160

Arg Arg Ile Pro Pro Glu Ser Val Asp Pro Gln Ile Lys Asn Tyr His
                165                170                175

Trp Leu Asp Leu Val Ala Gly Leu Leu Lys Gly Tyr Asp Ala Gly Ala
            180                185                190

Glu Ser Val Leu Leu Lys Cys Thr Asp Gly Ser Ile Ala Glu Gly Pro
            195                200                205

Gly Phe Asn Val Phe Val Val Arg Asp Gly Arg Leu Arg Thr Pro Glu
            210                215                220

Arg Gly Val Leu His Gly Ile Thr Arg Gln Thr Val Phe Glu Leu Ala
225                230                235                240

Thr Ala Met Gly Ile Asp Ala Gln Ala Arg Ile Asp Asp Ala Gln
            245                250                255

Leu Arg Asp Ala Asp Glu Val Phe Ile Thr Ser Thr Ala Gly Gly Ile
            260                265                270

Met Pro Val Thr Arg Leu Asn Asp Ala Thr Ile Gly Asp Gly Arg Pro
            275                280                285

Gly Pro Met Thr Arg Arg Leu Phe Asp Ala Tyr Trp Ala Lys His Gly
            290                295                300

Asp Pro Ala Trp Ser Leu Ala Val Asp Tyr Ala Asp Gly
305                310                315

<210> SEQ ID NO 12
<211> LENGTH: 954
<212> TYPE: DNA
<213> ORGANISM: Artificial sequence
<220> FEATURE:
<223> OTHER INFORMATION: Codon optimized sequence coding for SEQ ID 11

<400> SEQUENCE: 12
atgccgcgtg aaactcgttc tgcacaccac ggtatcccgt ctgttgaagc gccggcattc      60
ccgcagggcg cagcttacat gaacggtcgt ttcatcccaa tcgctgacgc tcgcgttcct     120
gtactggact ggggcttcct gcactctgac gttacttacg acaccgttca cgtatggaac     180
ggtcgtttct ccgtctgga caagcacatc gaacgtttcc gtcgttctct ggcgcgtctg     240
cgtctgaacg ttccgctgac tgacgacgcg ctgcgtgaca tcctggttga gtgcgtacgt     300
```

```
cgttctggtc tgcgtcacgc ttacgttgaa atgctgtgca ctcgcggtgt ttctccgact    360
ttctctcgcg atccgcgcga cgctgttaac cagttcatcg cgttcgctgt tccgtacggt    420
tctgttgcta acgaacgtca gctgcgtgaa ggtctgcacc tgcacgttat cgacgacgtt    480
cgtcgtatcc cgccagaatc cgttgatccg cagatcaaaa actaccactg gctggatctg    540
gttgctggtc tgctgaaagg ttacgacgct ggcgcagaat ccgttctgct gaaatgcact    600
gacggttcta cgctgaaggt ccgggcttc aacgtattcg ttgttcgtga cggtcgtctg    660
cgtactccgg aacgtggtgt tctgcacggt atcactcgtc agactgtatt cgaactggca    720
actgcgatgg gtatcgacgc tcaggctgca cgtatcgacg acgctcagct gcgtgacgct    780
gacgaagttt tcatcacttc tactgcaggt ggtatcatgc cggtaactcg tctgaacgac    840
gcaactatcg gtgacggtcg tccgggtccg atgactcgtc gtctgttcga cgcttactgg    900
gcgaagcacg gtgacccggc atggtctctg gcggttgact acgctgacgg ataa          954
```

<210> SEQ ID NO 13
<211> LENGTH: 337
<212> TYPE: PRT
<213> ORGANISM: Mycobacterium vanbaalenii
<400> SEQUENCE: 13

```
Met Gly Ile Asp Thr Gly Thr Ser Asn Leu Val Ala Val Glu Pro Gly
1               5                   10                  15

Ala Ile Arg Glu Asp Thr Pro Ala Gly Ser Val Ile Gln Tyr Ser Asp
            20                  25                  30

Tyr Glu Ile Asp Tyr Ser Ser Pro Phe Ala Gly Gly Val Ala Trp Ile
        35                  40                  45

Glu Gly Glu Tyr Leu Pro Ala Glu Asp Ala Lys Ile Ser Ile Phe Asp
    50                  55                  60

Thr Gly Phe Gly His Ser Asp Leu Thr Tyr Thr Val Ala His Val Trp
65                  70                  75                  80

His Gly Asn Ile Phe Arg Leu Gly Asp His Leu Asp Arg Leu Leu Asp
                85                  90                  95

Gly Ala Arg Lys Leu Arg Leu Asp Ser Gly Tyr Thr Lys Asp Glu Leu
            100                 105                 110

Ala Asp Ile Thr Lys Lys Cys Val Ser Leu Ser Gln Leu Arg Glu Ser
        115                 120                 125

Phe Val Asn Leu Thr Ile Thr Arg Gly Tyr Gly Lys Arg Lys Gly Glu
    130                 135                 140

Lys Asp Leu Ser Lys Leu Thr His Gln Val Tyr Ile Tyr Ala Ile Pro
145                 150                 155                 160

Tyr Leu Trp Ala Phe Pro Pro Ala Glu Gln Ile Phe Gly Thr Thr Ala
                165                 170                 175

Val Val Pro Arg His Val Arg Arg Ala Gly Arg Asn Thr Val Asp Pro
            180                 185                 190

Thr Ile Lys Asn Tyr Gln Trp Gly Asp Leu Thr Ala Ala Ser Phe Glu
        195                 200                 205

Ala Lys Asp Arg Gly Ala Arg Thr Ala Ile Leu Met Asp Ala Asp Asn
    210                 215                 220

Cys Val Ala Glu Gly Pro Gly Phe Asn Val Cys Ile Val Lys Asp Gly
225                 230                 235                 240

Lys Leu Ala Ser Pro Ser Arg Asn Ala Leu Pro Gly Ile Thr Arg Lys
                245                 250                 255

Thr Val Phe Glu Ile Ala Gly Ala Met Gly Ile Glu Ala Ala Leu Arg
```

```
            260                 265                 270
Asp Val Thr Ser His Glu Leu Tyr Asp Ala Asp Glu Ile Met Ala Val
            275                 280                 285

Thr Thr Ala Gly Gly Val Thr Pro Ile Asn Thr Leu Asp Gly Val Pro
        290                 295                 300

Ile Gly Asp Gly Glu Pro Gly Pro Val Thr Val Ala Ile Arg Asp Arg
305                 310                 315                 320

Phe Trp Ala Leu Met Asp Glu Pro Gly Pro Leu Ile Glu Ala Ile Gln
                325                 330                 335

Tyr

<210> SEQ ID NO 14
<211> LENGTH: 1014
<212> TYPE: DNA
<213> ORGANISM: Artificial sequence
<220> FEATURE:
<223> OTHER INFORMATION: Codon optimized sequence coding for SEQ ID NO
      13

<400> SEQUENCE: 14
atgggtatcg acaccggtac ttctaacctg gttgctgttg agccgggtgc tatccgtgaa      60
gatactccgg caggttctgt tatccagtac tctgactacg aaatcgacta ctcttctccg     120
ttcgctggcg gcgttgcatg gatcgaaggt gaatacctgc cggcagaaga tgcgaagatc     180
tccatcttcg acactggctt cggtcactct gacctgactt acaccgttgc tcacgtatgg     240
cacggtaaca tcttccgtct gggtgaccac ctggaccgtc tgctggacgg tgcgcgtaag     300
ctgcgtctgg attccggtta caccaaagac gaactggctg acatcaccaa gaaatgcgta     360
tctctgtctc agctgcgtga atccttcgtt aacctgacta tcactcgcgg ttacggtaag     420
cgtaaaggtg aaaaagacct gtctaaactg actcaccagg tttacatcta cgcaatcccg     480
tacctgtggg cattcccgcc agcagagcag atcttcggta ctactgctgt tgttccgcgt     540
cacgttcgtc gcgctggtcg taacaccgtt gatccgacta tcaaaaacta ccagtggggc     600
gacctgactg cagcttcttt cgaagcgaaa gaccgcggtg cacgtactgc gattctgatg     660
gacgctgaca actgcgttgc tgaaggtccg ggcttcaacg tttgcatcgt taaagacggt     720
aaactggctt ctccgtcccg taacgcgctg ccaggtatca ctcgtaaaac cgtattcgaa     780
atcgctggcg caatgggtat cgaagctgca ctgcgtgacg taacttctca gaactgtac     840 gacgctgacg aaatcatggc ggtaactact gctggcggcg ttactccgat caacaccctg     900
gatggcgttc cgatcggtga cggtgaaccg ggtccggtta ccgttgctat ccgtgaccgc     960
ttctgggcgc tgatggacga accgggtccg ctgatcgaag cgattcagta ctaa          1014

<210> SEQ ID NO 15
<211> LENGTH: 305
<212> TYPE: PRT
<213> ORGANISM: Unknown
<220> FEATURE:
<223> OTHER INFORMATION: Organism isolated from soil

<400> SEQUENCE: 15

Met Val Ser Asp Ile Phe Pro Lys Gly Ser Ala Trp Met Asn Gly Glu
1               5                   10                  15

Phe Ile Gln Leu Ser Glu Ala Lys Ile Pro Ile Leu Asp Trp Gly Phe
            20                  25                  30

Leu Arg Ser Asp Ala Thr Tyr Asp Val Val His Val Trp Lys Gly Ser
        35                  40                  45
```

Phe Gln Leu Asp Lys His Ile Asp Arg Phe Phe Lys Ser Thr Glu
    50                  55                  60

Lys Leu Arg Met Pro Cys Arg Leu Ser Arg Glu Glu Ile Lys Arg Ile
65                  70                  75                  80

Leu Ala Gly Cys Val Lys Lys Ala Asp Leu Glu Asp Ser Tyr Val Glu
                85                  90                  95

Met Ile Gln Thr Arg Gly Met Ser Pro Asn Phe Val Arg Asp Pro Arg
            100                 105                 110

Lys Ala Thr Pro Arg Phe Met Ala Phe Ala Val Pro Phe Gly Trp Ile
            115                 120                 125

Leu Arg Pro Glu Asp Phe Glu Lys Gly Leu Asp Val Tyr Leu Thr Asp
            130                 135                 140

Ile Thr Arg Ile Pro Pro Ser Ser Val Asp Pro Thr Ile Lys Asn Tyr
145                 150                 155                 160

His Trp Met Asp Leu Val Thr Gly Met Leu Asp Ala Tyr Asp Arg Gly
                165                 170                 175

His His Thr Ala Ile Leu Val Asp Glu Asp Asn Asn Val Ser Glu Gly
            180                 185                 190

Pro Gly Phe Asn Ile Phe Ser Val Asp Glu Asn Glu Ile Asn Thr Pro
            195                 200                 205

Asp His Gly Val Leu Glu Gly Ile Thr Arg Gln Thr Val Ile Asp Leu
    210                 215                 220

Ala Lys Glu Leu Asn Ile Lys Val Asn Lys Lys Pro Ile Thr Ile Lys
225                 230                 235                 240

Met Leu Lys Ser Ser Glu Glu Leu Phe Ala Thr Ser Thr Ala Gly Gly
                245                 250                 255

Val Met Pro Ile Thr Lys Ile Ser Gly Lys Asn Ile Asn Lys Gly Thr
            260                 265                 270

Val Gly Asp Ile Thr Arg Lys Ile His Lys Leu Tyr Trp Asp Lys His
            275                 280                 285

Ser Asp Pro Asp Trp Ser Thr Ser Ile Asn Asp Ile Leu Leu Tyr Lys
    290                 295                 300

Val
305

<210> SEQ ID NO 16
<211> LENGTH: 915
<212> TYPE: DNA
<213> ORGANISM: Artificial seqience
<220> FEATURE:
<223> OTHER INFORMATION: Codon optimized sequence coding for SEQ ID NO
      15

<400> SEQUENCE: 16
atggtttctg acatcttccc gaaaggttct gcatggatga acgtgaatt catccagctg      60 tctgaagcga aaatcccgat cctcgactgg ggcttcctgc gttctgacgc aacttacgac     120
gttgttcacg tatggaaagg ttctttcttc agctggaca agcacatcga ccgcttcttc      180
aaatctactg aaaaactgcg tatgccatgc cgtctgtctc gtgaagaaat caagcgtatc     240
ctggctggct gcgttaagaa agctgacctg gaagactcct acgttgaaat gatccagact     300
cgcggtatgt ctccgaactt cgttcgtgac ccgcgtaaag caactccgcg cttcatggcg     360
ttcgctgttc cgttcggctg gattctgcgt ccggaagact cgaaaaaggg tctggacgtt     420
tacctgactg acatcactcg tatcccgccg tcttccgttg atccgactat caaaaactac     480

```
cactggatgg aacctggttac cggtatgctg gatgcttacg accgcggtca ccacactgcg    540
attctggttg acgaagataa caacgtttct gaaggtccgg gcttcaacat cttctctgtt    600
gacgaaaacg aaatcaacac tccggatcac ggcgtactgg aaggtatcac tcgtcagact    660
gttatcgacc tggctaaaga gctgaacatc aaagttaaca agaaaccaat cactatcaaa    720
atgctgaaat cttctgaaga gctgttcgca acttctactg ctggcggcgt aatgccgatc    780
accaagatct ccggtaaaaa catcaacaaa ggcaccgttg gtgacatcac tcgtaagatc    840
cacaaactgt actgggacaa gcactctgat ccggactggt ctacttccat caacgacatc    900
ctgctgtaca aggta                                                      915
```

<210> SEQ ID NO 17
<211> LENGTH: 291
<212> TYPE: PRT
<213> ORGANISM: Mesorhizobium loti

<400> SEQUENCE: 17

```
Met Ala Phe Met Asp Gly Gln Tyr Leu Pro Met Ser Glu Ala Lys Val
1               5                   10                  15

Ser Val Leu Asp Trp Gly Phe Leu His Ser Asp Ala Thr Tyr Asp Thr
            20                  25                  30

Val His Val Trp Asp Gly Arg Phe Phe Arg Leu Asn Leu His Val Asp
        35                  40                  45

Arg Phe Phe Arg Gly Met Glu Lys Leu Arg Met Lys Leu Pro Tyr Asn
    50                  55                  60

Arg Ser Glu Ile Glu Lys Ile Leu Ser Thr Cys Val Ala Leu Ser Gly
65                  70                  75                  80

His Lys Ser Ala Tyr Val Glu Met Ile Cys Thr Arg Gly Gly Ser Pro
                85                  90                  95

Thr Phe Ser Arg Asp Pro Arg Gln Ser Glu Asn Arg Phe Ile Ala Phe
            100                 105                 110

Ala Val Pro Phe Gly Ser Val Ala Asn Lys Glu Gln Leu Glu Arg Gly
        115                 120                 125

Leu His Val Ala Ile Ser Asn Thr Val Arg Ile Pro Pro Lys Ser Ile
130                 135                 140

Asp Pro Thr Ile Lys Asn Tyr His Trp Leu Asp Leu Val Lys Gly Leu
145                 150                 155                 160

Phe Asp Ala Tyr Asp Tyr Gly Ala Glu Thr Ala Leu Ile Val Asp Ile
                165                 170                 175

Asn Asp Asn Ile Ala Glu Gly Pro Gly Phe Asn Val Phe Thr Val Lys
            180                 185                 190

Asp Gly Arg Leu Lys Thr Pro Ala Tyr Gly Val Leu Ala Gly Ile Thr
        195                 200                 205

Arg Gln Thr Val Phe Asp Leu Cys Asp Glu Leu Gly Leu Ser Val Ser
    210                 215                 220

Ala Gly Asp Ile Asp Arg Asn Glu Leu Lys Gly Ala Asp Glu Val Phe
225                 230                 235                 240

Ile Thr Ser Thr Ala Gly Gly Ile Met Pro Val Ser Lys Ile Asp Glu
                245                 250                 255

Thr Val Val Gly Asp Gly Lys Val Gly Ala Leu Thr Arg Gln Leu Ala
            260                 265                 270

Asp Leu Tyr Trp Glu Lys His Ala Asp Pro Ala Trp Ser Thr Ala Val
        275                 280                 285

Asn Tyr Ala
```

<210> SEQ ID NO 18
<211> LENGTH: 876
<212> TYPE: DNA
<213> ORGANISM: Artificial sequence
<220> FEATURE:
<223> OTHER INFORMATION: Codon optimized sequence coding for SEQ ID NO 17

<400> SEQUENCE: 18

```
atggcgttca tggacggtca gtacctgccg atgtctgaag cgaaagtttc tgtactggac      60
tggggcttcc tgcactctga cgcaacttac gacaccgttc acgtatggga cggtcgtttc     120
ttccgtctga acctgcacgt tgaccgcttc ttccgcggta tggaaaaact gcgtatgaag     180
ctgccgtaca accgttctga aatcgaaaaa atcctgtcta cttgcgtagc gctgtctggt     240
cacaagtctg cttacgttga atgatctgt actcgcggtg ttctccgac tttctctcgc      300
gatccgcgtc agtctgaaaa ccgcttcatc gcgttcgctg ttccgttcgg ttctgttgct     360
aacaaagagc agctggaacg tggtctgcac gttgctatct ccaacaccgt tcgtatcccg     420
ccaaagtcta tcgacccgac tatcaaaaac taccactggc tggatctggt taaaggtctg     480
ttcgacgctt acgactacgg cgcagaaact gcactgatcg ttgatatcaa cgacaacatc     540
gctgaaggtc cgggcttcaa cgtattcacc gttaaagacg tcgtctgaa actccggct      600
tacggcgttc tggcaggtat cactcgtcag actgtattcg acctgtgcga cgaactgggt     660
ctgtctgttt ctgctggcga catcgaccgt aacgaactga aggtgctga cgaagttttc     720
atcacttcta ctgcaggtgg tatcatgccg gtttccaaga tcgacgaaac cgttgttggt     780
gacggtaaag ttggtgcgct gactcgtcag ctggctgacc tgtactggga aaaacacgct     840
gatccggcat ggtctactgc tgttaactac gcataa                              876
```

<210> SEQ ID NO 19
<211> LENGTH: 299
<212> TYPE: PRT
<213> ORGANISM: Unknown
<220> FEATURE:
<223> OTHER INFORMATION: Organism isolated from soil

<400> SEQUENCE: 19

```
Met Thr Tyr Ser Ala Gly Ala Ala Trp Met Asp Gly Lys Val Ile Pro
1               5                   10                  15

Val Ser Glu Ala Lys Ile Ser Val Phe Asp Trp Gly Leu Thr Arg Ser
            20                  25                  30

Asp Ile Thr Tyr Asp Val Val His Val Trp Glu Gly Ala Phe Phe Arg
        35                  40                  45

Leu Glu Asp Tyr Leu Asp Arg Phe Met Val Ser Met Lys Leu Arg
    50                  55                  60

Leu Asp Val Gly Met Thr Arg Ala Glu Ile Lys Ala Ala Leu Val Glu
65                  70                  75                  80

Leu Val Ala Thr Ser Gly Leu Lys Ser Ala Tyr Val Ser Met Val Ala
                85                  90                  95

Ser Arg Gly Thr Pro Gln Val Pro Gly Thr Arg Asp Pro Arg Ala Cys
            100                 105                 110

Thr Asn His Phe Tyr Ala Trp Ala Val Pro Phe Ile Trp Val Ile Pro
        115                 120                 125

Gln Glu Val Ala Gln Arg Gly Ala His Ile Ser Val Glu Glu Asn Leu
    130                 135                 140
```

```
Arg Arg Ile Pro Pro His Ser Val Asp Pro Thr Val Lys Asn Tyr His
145                 150                 155                 160

Trp Gly Asp Met Thr Ala Ala Leu Phe Asn Ala Leu Asp Ala Gly Tyr
                165                 170                 175

Asp Thr Thr Val Leu Leu Asp Thr Asp Gly Tyr Val Thr Glu Gly Pro
            180                 185                 190

Gly Phe Asn Ile Phe Ala Val Ile Asp Gly Lys Val Leu Thr Pro Arg
        195                 200                 205

Ser Gly Met Leu Glu Gly Ile Ser Arg Lys Thr Val Leu Glu Ile Cys
    210                 215                 220

Ala Asp Leu Gly Ile Pro Cys Ala Gln Thr Asp Ile Ser Leu Asp Glu
225                 230                 235                 240

Phe Leu Ser Ala Asp Glu Val Phe Thr Ala Thr Thr Ala Gly Gly Pro
                245                 250                 255

Val Pro Val Thr Arg Val Asn Lys Thr Ile Leu Gly Asn Asp Ala Val
            260                 265                 270

Gly Pro Ile Thr Ala Arg Leu Leu Lys Thr Tyr Trp Asp Trp His Asn
        275                 280                 285

Arg Asp Asp Leu Thr Glu Lys Ile Thr Tyr Val
    290                 295

<210> SEQ ID NO 20
<211> LENGTH: 900
<212> TYPE: DNA
<213> ORGANISM: Artificial sequence
<220> FEATURE:
<223> OTHER INFORMATION: Codon optimized sequence coding for SEQ ID NO
      19

<400> SEQUENCE: 20
atgacttact ccgcaggtgc tgcatggatg gacggtaaag ttatcccggt ttctgaagcg     60
aagatctccg tattcgactg gggtctgact cgttctgaca tcacttacga cgttgttcac    120
gtatgggaag gtgcattctt ccgtctggaa gactacctgg atcgcttcat ggtttccatg    180
gacaagctgc gtctggacgt tggtatgact cgcgctgaaa tcaaagctgc gctggttgaa    240
ctggttgcaa cttctggtct gaaatctgct tacgtttcca tggttgcttc tcgcggtact    300
ccgcaggttc cggtactcg tgacccgcgc gcttgcacca accacttcta cgcatgggcg    360
gtaccgttca tctgggttat cccgcaggaa gttgctcagc gtggtgctca catctccgtt    420
gaagaaaacc tgcgtcgtat cccgccgcac tctgttgatc cgaccgttaa aaactaccac    480
tggggcgaca tgactgctgc gctgttcaac gcgctggatg ctggttacga cactaccgtt    540
ctgctggata tgacggtta cgttactgaa ggtccgggct caacatcatt cgctgttatc    600
gacggtaaag ttctgactcc gcgttctggt atgctggaag gtatctcccg taaaaccgtt    660
ctggaaatct gcgcagacct gggtatccca tgcgcacaga ctgacatctc tctggacgag    720
ttcctgtctg ctgacgaagt attcactgca accactgctg gcggtccggt accggtaact    780
cgcgttaaca aaactattct gggtaacgac gctgttggtc cgatcactgc gcgtctgctg    840
aaaacttact gggactggca caaccgtgac gacctgaccg agaagatcac ttacgtctaa    900

<210> SEQ ID NO 21
<211> LENGTH: 299
<212> TYPE: PRT
<213> ORGANISM: Unknown
<220> FEATURE:
<223> OTHER INFORMATION: Organism isolated from soil
```

<400> SEQUENCE: 21

```
Met Thr Tyr Ala Thr Gly Ala Ala Trp Met Asp Gly Gln Val Ile Pro
1               5                   10                  15
Val Ser Glu Ala Lys Ile Ser Val Phe Asp Trp Gly Leu Thr Arg Ser
            20                  25                  30
Asp Ile Thr Tyr Asp Val Val His Val Trp Glu Gly Ala Phe Phe Arg
        35                  40                  45
Leu Glu Asp Tyr Leu Asp Arg Phe Thr Val Ser Met Asp Lys Leu Arg
    50                  55                  60
Leu Asp Val Gly Met Asn Arg Ala Asp Ile Lys Ala Ala Leu Val Glu
65                  70                  75                  80
Leu Val Ala Thr Ser Gly Leu Gln Ser Ala Tyr Val Ser Met Val Ala
                85                  90                  95
Ser Arg Gly Thr Pro Leu Val Pro Gly Thr Arg Asp Pro Arg Ala Cys
            100                 105                 110
Thr Asn His Phe Tyr Ala Trp Ala Val Pro Phe Ile Trp Val Ile Pro
        115                 120                 125
Gln Glu Val Ala Gln Arg Gly Ala His Ile Ser Val Glu Glu Asn Leu
    130                 135                 140
Arg Arg Ile Pro Pro His Ser Val Asp Pro Thr Val Lys Asn Tyr His
145                 150                 155                 160
Trp Gly Asp Met Thr Ala Ala Leu Phe Asn Ala Leu Asp Ala Gly Tyr
                165                 170                 175
Asp Thr Thr Val Leu Leu Asp Thr Asn Gly Tyr Ile Thr Glu Gly Pro
            180                 185                 190
Gly Phe Asn Ile Phe Ala Val Ile Asp Gly Lys Val Leu Thr Pro Arg
        195                 200                 205
Leu Gly Met Leu Glu Gly Ile Ser Arg Lys Thr Val Leu Glu Ile Cys
    210                 215                 220
Ala Asp Leu Gly Ile Pro Cys Ala Glu Ala Asp Ile Ser Leu Ala Glu
225                 230                 235                 240
Phe Leu Ser Ala Asp Glu Leu Phe Thr Ala Thr Thr Ala Gly Gly Pro
                245                 250                 255
Val Pro Val Thr Arg Val Asn Lys Thr Ile Leu Gly Asn Asp Ala Ile
            260                 265                 270
Gly Pro Ile Thr Ala Gln Val Leu Lys Thr Tyr Trp Asp Trp His His
        275                 280                 285
Arg Asp Asp Leu Thr Glu Lys Ile Ala Tyr Ile
    290                 295
```

<210> SEQ ID NO 22
<211> LENGTH: 900
<212> TYPE: DNA
<213> ORGANISM: Artificial sequence
<220> FEATURE:
<223> OTHER INFORMATION: Codon optimized sequence coding for SEQ ID NO 21

<400> SEQUENCE: 22

```
atgacttacg caactggcgc tgcatggatg gacggtcagg ttatcccggt ttctgaagcg    60
aagatctccg tattcgactg gggtctgact cgttctgaca tcacttacga cgttgttcac   120
gtatgggaag gtgcgttctt ccgtctggaa gactacctgg atcgcttcac cgtttccatg   180
gacaagctgc gtctggacgt tggtatgaac cgcgctgaca tcaaagcggc actggttgaa   240
```

```
ctggttgcaa cttctggtct gcagtctgct tacgtttcca tggttgcttc tcgcggtact    300
ccgctggtac cgggtactcg tgacccgcgc gcttgcacca accacttcta cgcatgggcg    360
gtaccgttca tctgggttat cccgcaggaa gttgctcagc gtggtgcgca catctccgtt    420
gaagaaaacc tgcgtcgtat cccgccgcac tctgttgatc cgaccgttaa gaactaccac    480
tggggcgaca tgactgctgc gctgttcaac gcgctggatg ctggttacga cactaccgtt    540
ctgctggata ccaacggtta catcactgaa ggtccgggct tcaacatctt cgctgttatc    600
gacggtaaag ttctgactcc gcgtctgggt atgctggaag gtatctcccg taaaaccgtt    660
ctggaaatct gcgcagacct gggtatccca tgcgcagaag ctgacatctc tctggctgag    720
ttcctgtctg ctgacgaact gttcactgca accactgcag gtggtccggt accggtaact    780
cgcgttaaca aaactattct gggtaacgac gctatcggtc cgatcactgc tcaggttctg    840
aaaacttact gggactggca ccaccgtgac gacctgactg aaaaaatcgc ttacatttaa    900
```

<210> SEQ ID NO 23
<211> LENGTH: 326
<212> TYPE: PRT
<213> ORGANISM: Unknown
<220> FEATURE:
<223> OTHER INFORMATION: Organism isolated from soil
<400> SEQUENCE: 23

```
Met Ala Ile Ile Gln Val Gln Gln Ile Met His Glu Asn Pro Leu His
1               5                   10                  15

Ala Arg Ala Pro His Glu Pro Arg Tyr Glu Asp Gly Ser Ala Phe Cys
            20                  25                  30

Asp Gly Lys Tyr Val Pro Ile Ser Glu Ala Thr Val Pro Leu Val Asp
        35                  40                  45

Ala Gly Phe Leu His Ala Asp Ala Ala Tyr Asp Val Val Thr Val Ser
    50                  55                  60

Arg Gly Asn Phe Phe Arg Leu Asp Asp His Leu Ala Arg Met Glu Glu
65                  70                  75                  80

Ser Ser Ala Lys Phe Phe Leu Glu Asn Pro Phe Asn Arg Asp Gln Val
                85                  90                  95

Arg Glu Ile Leu His Asn Leu Val Arg Asn Ala Gly Leu Lys Asp Ala
            100                 105                 110

Tyr Val Trp Trp Cys Val Thr Arg Gly Pro Leu Ser Val Asp Arg Arg
        115                 120                 125

Asp Arg Ser Ala Met Lys Asn Ala Met Phe Ala Phe Ala Val Pro Phe
    130                 135                 140

Phe Phe Gln Ala Asp Asp Glu Val Arg Thr Arg Gly Ser Asn Leu Leu
145                 150                 155                 160

Ile Ser Lys Arg Tyr Asn Arg Ile Ser Ala Lys Ala Val Asp Pro Thr
                165                 170                 175

Ala Lys Asn Phe His Trp Met Asp Met Lys Leu Ala Leu Phe Glu Ala
            180                 185                 190

Met Thr Gln Glu Lys Asp Trp Ala Val Leu Val Asp Glu His Asp Asn
        195                 200                 205

Leu Thr Glu Ala Ala Gly Ala Asn Val Phe Val Lys Asn Gly Glu
    210                 215                 220

Leu Tyr Thr Pro Ala Glu Gly Cys Leu Leu Gly Ile Thr Arg Gln Ser
225                 230                 235                 240

Val Phe Asp Ile Ala Ala Glu Leu Gly Ile Lys Val Asn Ile Gly Lys
                245                 250                 255
```

```
Tyr Thr Ala Thr Gln Leu Arg Glu Ala Asp Glu Ala Phe Thr Ser Ser
            260                 265                 270

Ser Ala Gly Gly Ile Met Pro Val Ser Ala Val Asp Asp Gln Pro Leu
        275                 280                 285

Gly Asn His Asn Gly Pro Gly Pro Ile Ser Glu Lys Ile His Asn Leu
    290                 295                 300

Tyr Trp Glu Lys Arg Trp Ala Gly Trp His Ala Gln Pro Ala Glu Tyr
305                 310                 315                 320

Phe Ser Ser Ile Pro Ala
                325

<210> SEQ ID NO 24
<211> LENGTH: 981
<212> TYPE: DNA
<213> ORGANISM: Artificial sequence
<220> FEATURE:
<223> OTHER INFORMATION: Codon optimized sequence coding for SEQ ID NO
      23

<400> SEQUENCE: 24
atggctatca tccaggttca gcagatcatg cacgaaaacc cgctgcacgc gcgtgctccg      60
cacgaaccgc gctacgaaga cggttctgca ttctgcgacg gtaaatacgt tccgatttct     120
gaagcaaccg ttccgctggt tgatgctggc ttcctgcacg ctgacgctgc ttacgacgtt     180
gttaccgttt ctcgcggtaa cttcttccgt ctggatgacc acctggcgcg tatggaagag     240
tcttctgcga aattcttcct ggaaaacccg ttcaaccgtg accaggttcg tgaaatcctg     300
cacaacctgg ttcgtaacgc aggtctgaaa gacgcttacg tatggtggtg cgtaactcgc     360
ggtccgctgt ctgttgaccg tcgtgaccgt tctgcgatga agaacgcaat gttcgctttc     420
gctgttccgt tcttcttcca ggctgacgac gaagttcgta ctcgcggttc taaccctgctg    480 atctccaagc gctacaaccg tatctctgcg aaagctgttg atccgactgc gaaaaacttc     540
cactggatgg acatgaagct ggcgctgttc gaagcgatga ctcaggaaaa agactgggcg     600
gtactggttg acgaacacga caacctgact gaagctgcag gtgctaacgt attcttcgtt     660
aaaaacggtg aactgtacac tccggcagaa ggttgcctgc tgggtatcac tcgtcagtct     720
gtattcgaca tcgctgctga actgggtatc aaagttaaca tcggtaaata cactgcaact     780
cagctgcgta agctgacga agcattcact tcttcttccg caggtggtat catgccggtt    840
tctgctgttg atgaccagcc gctgggtaac cacaacggtc cgggtccaat ctctgagaag     900
atccacaacc tgtactggga aaaacgctgg gctggctggc acgctcagcc ggcagaatac     960
ttctcttcca tcccggcata a                                              981

<210> SEQ ID NO 25
<211> LENGTH: 326
<212> TYPE: PRT
<213> ORGANISM: Burkholderia sp. 383

<400> SEQUENCE: 25

Met Ala Ile Ile Gln Val Gln Gln Ile Met His Glu Asn Pro Leu His
1               5                   10                  15

Ala Arg Ala Pro His Glu Pro Arg Tyr Glu Asp Gly Ser Ala Phe Cys
            20                  25                  30

Asp Gly Asn Tyr Val Pro Ile Thr Glu Ala Thr Val Pro Leu Val Asp
        35                  40                  45

Ala Gly Phe Leu His Ala Asp Ala Ala Tyr Asp Val Val Thr Val Ser
```

```
                    50                  55                  60
Arg Gly Asn Phe Phe Arg Leu Asp Asp His Leu Thr Arg Met Glu Glu
 65                  70                  75                  80

Ser Ser Ala Lys Phe Leu Glu Asn Pro Phe Asn Arg Asp Gln Val
                 85                  90                  95

Lys Glu Ile Leu His Asn Leu Val Arg Asn Ala Gly Leu Lys Asp Ala
                100                 105                 110

Tyr Val Trp Trp Cys Val Thr Arg Gly Pro Leu Ser Val Asp Arg Arg
                115                 120                 125

Asp Arg Gly Ala Met Lys Asn Ala Met Phe Ala Phe Ala Val Pro Phe
            130                 135                 140

Phe Phe Gln Ala Asp Asp Glu Val Arg Thr Arg Gly Ser Asn Leu Leu
145                 150                 155                 160

Ile Ser Lys Leu Tyr Asn Arg Ile Ser Ala Lys Ala Val Asp Pro Thr
                165                 170                 175

Ala Lys Asn Phe His Trp Met Asp Met Lys Leu Ala Leu Phe Glu Ala
                180                 185                 190

Met Thr Gln Glu Lys Asp Trp Ala Val Leu Val Asp Glu Ser Asp Asn
                195                 200                 205

Leu Thr Glu Ala Ala Gly Ala Asn Val Phe Phe Ala Lys Asn Gly Glu
    210                 215                 220

Leu Tyr Thr Pro Ala Glu Gly Cys Leu Leu Gly Ile Thr Arg Gln Ser
225                 230                 235                 240

Val Phe Asp Ile Ala Ala Glu Leu Gly Ile Lys Val Asn Ile Gly Lys
                245                 250                 255

Tyr Thr Ala Thr Gln Leu Arg Glu Ala Asp Glu Ala Phe Thr Ser Ser
                260                 265                 270

Ser Ala Gly Gly Ile Met Pro Val Ser Ala Ile Asp Asp Gln Pro Leu
                275                 280                 285

Gly Asn Arg Asn Gly Pro Gly Pro Ile Ser Glu Lys Ile His Asn Leu
            290                 295                 300

Tyr Trp Glu Lys Arg Trp Ala Gly Trp His Ala Gln Pro Ala Glu Tyr
305                 310                 315                 320

Phe Ser Ser Val Pro Ala
                325

<210> SEQ ID NO 26
<211> LENGTH: 981
<212> TYPE: DNA
<213> ORGANISM: Artificial sequence
<220> FEATURE:
<223> OTHER INFORMATION: Codon optimized sequence coding for SEQ ID NO
      25

<400> SEQUENCE: 26
atggctatca tccaggttca gcagatcatg cacgaaaacc cgctgcacgc gcgtgctccg      60
cacgaaccgc gctacgaaga cggttctgca ttctgcgacg gtaactacgt tccgatcact     120
gaagcaaccg ttccgctggt tgatgctggc ttcctgcacg ctgacgctgc ttacgacgtt     180
gttaccgttt ctcgcggtaa cttcttccgt ctggatgacc acctgactcg tatggaagag     240
tcttctgcga aattcttcct ggaaaacccg ttcaaccgtg accaggttaa agaaatcctg     300
cacaacctgg ttcgtaacgc aggtctgaaa gacgcttacg tatggtggtg cgtaactcgc     360
ggtccgctgt ctgttgaccg tcgtgaccgc ggtgcgatga agaacgcaat gttcgctttc     420
gctgttccgt tcttcttcca ggctgatgac gaagttcgta ctcgcggttc taacctgctg     480
```

```
atctccaagc tgtacaaccg tatctctgcg aaagcggttg atccgactgc gaaaaacttc    540
cactggatgg acatgaagct ggcgctgttc gaagcgatga ctcaggaaaa agactgggcg    600
gtactggttg acgaatctga caacctgact gaagctgcag gtgctaacgt attcttcgct    660
aaaaacggtg aactgtacac tccggcagaa ggttgcctgc tgggtatcac tcgtcagtct    720
gtattcgaca tcgctgctga actgggtatc aaagttaaca tcggtaaata cactgcaact    780
cagctgcgtg aagctgacga agcattcact tcttcttccg caggtggtat catgccggtt    840
tctgctatcg acgaccagcc gctgggtaac cgtaacggtc cgggtccgat ttctgagaag    900
atccacaacc tgtactggga aaacgctggg gctggctggc acgctcagcc ggcagaatac    960
ttctcttccg ttcccgcata a                                              981
```

```
<210> SEQ ID NO 27
<211> LENGTH: 283
<212> TYPE: PRT
<213> ORGANISM: Bacillus sp. YM-1

<400> SEQUENCE: 27

Met Gly Tyr Thr Leu Trp Asn Asp Gln Ile Val Lys Asp Glu Glu Val
1               5                   10                  15

Lys Ile Asp Lys Glu Asp Arg Gly Tyr Gln Phe Gly Asp Gly Val Tyr
                20                  25                  30

Glu Val Val Lys Val Tyr Asn Gly Glu Met Phe Thr Val Asn Glu His
            35                  40                  45

Ile Asp Arg Leu Tyr Ala Ser Ala Glu Lys Ile Arg Ile Thr Ile Pro
        50                  55                  60

Tyr Thr Lys Asp Lys Phe His Gln Leu Leu His Glu Leu Val Glu Lys
65                  70                  75                  80

Asn Glu Leu Asn Thr Gly His Ile Tyr Phe Gln Val Thr Arg Gly Thr
                85                  90                  95

Ser Pro Arg Ala His Gln Phe Pro Glu Asn Thr Val Lys Pro Val Ile
            100                 105                 110

Ile Gly Tyr Thr Lys Glu Asn Pro Arg Pro Leu Glu Asn Leu Glu Lys
        115                 120                 125

Gly Val Lys Ala Thr Phe Val Glu Asp Ile Arg Trp Leu Arg Cys Asp
130                 135                 140

Ile Lys Ser Leu Asn Leu Leu Gly Ala Val Leu Ala Lys Gln Glu Ala
145                 150                 155                 160

His Glu Lys Gly Cys Tyr Glu Ala Ile Leu His Arg Asn Asn Thr Val
                165                 170                 175

Thr Glu Gly Ser Ser Ser Asn Val Phe Gly Ile Lys Asp Gly Ile Leu
            180                 185                 190

Tyr Thr His Pro Ala Asn Asn Met Ile Leu Lys Gly Ile Thr Arg Asp
        195                 200                 205

Val Val Ile Ala Cys Ala Asn Glu Ile Asn Met Pro Val Lys Glu Ile
210                 215                 220

Pro Phe Thr Thr His Glu Ala Leu Lys Met Asp Glu Leu Phe Val Thr
225                 230                 235                 240

Ser Thr Thr Ser Glu Ile Thr Pro Val Ile Glu Ile Asp Gly Lys Leu
                245                 250                 255

Ile Arg Asp Gly Lys Val Gly Glu Trp Thr Arg Lys Leu Gln Lys Gln
            260                 265                 270

Phe Glu Thr Lys Ile Pro Lys Pro Leu His Ile
        275                 280
```

<210> SEQ ID NO 28
<211> LENGTH: 852
<212> TYPE: DNA
<213> ORGANISM: Artificial sequence
<220> FEATURE:
<223> OTHER INFORMATION: Codon optimized sequence coding for SEQ ID NO
      27

<400> SEQUENCE: 28

| | | |
|---|---|---|
| atgggttaca ctctgtggaa cgaccagatc gttaaagacg aagaagttaa gatcgacaaa | 60 |
| gaagaccgtg ttaccagtt cggtgacggt gtttacgaag ttgttaaagt ttacaacggt | 120 |
| gaaatgttca ccgttaacga acacatcgac cgtctgtacg cttctgctga aaaaatccgt | 180 |
| atcactatcc cgtacaccaa agacaaattc caccagctgc tgcacgaact ggttgaaaaa | 240 |
| aacgaactga acaccggtca catctacttc caggtaactc gcggtacttc ccgcgcgct | 300 |
| caccagttcc cggaaaacac cgttaagccg gttatcatcg gttacaccaa agagaacccg | 360 |
| cgtccgctgg aaaacctgga aaaggcgtt aaagcaactt tcgttgaaga tatccgctgg | 420 |
| ctgcgctgcg acatcaagtc tctgaacctg ctgggtgcgg tactggcgaa gcaggaagca | 480 |
| cacgaaaaag ctgctacga agctatcctg caccgtaaca acaccgtaac tgaaggttct | 540 |
| tcttctaacg tattcggtat caaagacggt attctgtaca ctcacccggc taacaacatg | 600 |
| atcctgaaag gtatcactcg tgacgttgtt atcgcttgcg caaacgaaat caacatgccg | 660 |
| gttaaagaga tcccgttcac cactcacgaa gcgctgaaaa tggacgaact gttcgtaact | 720 |
| tctaccactt ctgaaatcac tccggttatc gaaatcgacg gtaaactgat ccgtgacggt | 780 |
| aaagttggcg agtggactcg taagctgcag aagcagttcg aaaccaagat cccgaagccg | 840 |
| ctgcacatat aa | 852 |

<210> SEQ ID NO 29
<211> LENGTH: 918
<212> TYPE: DNA
<213> ORGANISM: Curtobacterium pusillum
<220> FEATURE:
<221> NAME/KEY: CDS
<222> LOCATION: (1)..(918)

<400> SEQUENCE: 29

| | |
|---|---|
| atg acc cgt gcg acc ctc ctg acc gtg acc gcg ccg acc cgt ccc gcc<br>Met Thr Arg Ala Thr Leu Leu Thr Val Thr Ala Pro Thr Arg Pro Ala<br>1               5                   10                  15 | 48 |
| tcg gcg gac gag cac ggg gcg gac cgt gcc gcc ggc gac gcc ggc ttc<br>Ser Ala Asp Glu His Gly Ala Asp Arg Ala Ala Gly Asp Ala Gly Phe<br>            20                  25                  30 | 96 |
| gtc ctc gcc gac ttc ggc gca ccg cag gtc cgc atc acc gac ctc ggc<br>Val Leu Ala Asp Phe Gly Ala Pro Gln Val Arg Ile Thr Asp Leu Gly<br>        35                  40                  45 | 144 |
| atc acg cgc ggc gac ggg gtg ttc gag acc atc gcc gtg atc gac ggg<br>Ile Thr Arg Gly Asp Gly Val Phe Glu Thr Ile Ala Val Ile Asp Gly<br>    50                  55                  60 | 192 |
| cac ccg cag gcg ctg gaa ctg cac ctc gga cgg ctg gcc cac tcg gcg<br>His Pro Gln Ala Leu Glu Leu His Leu Gly Arg Leu Ala His Ser Ala<br>65                  70                  75                  80 | 240 |
| gcg ctc ctc gac ctc ccc gaa ccg gat gcg gcg gtg tgg cgg gag gcc<br>Ala Leu Leu Asp Leu Pro Glu Pro Asp Ala Ala Val Trp Arg Glu Ala<br>                85                  90                  95 | 288 |
| gtc ctc gcg ggc gtg gcg gac tac cgg tcc cgc aac ggc gac ggc ggc | 336 |

```
gaa ctg ttc gcc aag ctc atc ctg acc cgc ggc atc gag ggc gag ggc      384
Glu Leu Phe Ala Lys Leu Ile Leu Thr Arg Gly Ile Glu Gly Glu Gly
        115                 120                 125 cgg ccg agc ggg tgg gtg ttc gtg gac gag ggc gag gac ttc tcg cag      432
Arg Pro Ser Gly Trp Val Phe Val Asp Glu Gly Glu Asp Phe Ser Gln
130                 135                 140 cag cgc ctc ggg atc cgc gtc gtc acg ctc gac cgc ggc tac cgt cac      480
Gln Arg Leu Gly Ile Arg Val Val Thr Leu Asp Arg Gly Tyr Arg His
145                 150                 155                 160 gac gtg gcg gag acg tcc ccg tgg ctg ctg gcc gga gcg aag tcc ctg      528
Asp Val Ala Glu Thr Ser Pro Trp Leu Leu Ala Gly Ala Lys Ser Leu
                165                 170                 175 tcg tac gcg acc aat cgc gcc gcc ggc cgg gag gcg gcc cgc cgg ggc      576
Ser Tyr Ala Thr Asn Arg Ala Ala Gly Arg Glu Ala Ala Arg Arg Gly
            180                 185                 190 gcc gac gac gtg atc ttc gtc agc tcc gac gga tac gca ctg gag ggg      624
Ala Asp Asp Val Ile Phe Val Ser Ser Asp Gly Tyr Ala Leu Glu Gly
        195                 200                 205 ccg acc tcg aac gtc atc gtg ctt gcg gac ggc gtc gtg cgc acc ccg      672
Pro Thr Ser Asn Val Ile Val Leu Ala Asp Gly Val Val Arg Thr Pro
    210                 215                 220 cag acg gac cag ggc atc ctg gcc ggc acc acc cag gcg gcc gtg ttc      720
Gln Thr Asp Gln Gly Ile Leu Ala Gly Thr Thr Gln Ala Ala Val Phe
225                 230                 235                 240 gac ttc ttc gag gag cgc ggc tac ccc acc gag tac cgc cgc atc tcc      768
Asp Phe Phe Glu Glu Arg Gly Tyr Pro Thr Glu Tyr Arg Arg Ile Ser
                245                 250                 255 gcg gac gag ctg cgc gac gcg gag gcg ctg tgg ctc gtc tcc agc gtg      816
Ala Asp Glu Leu Arg Asp Ala Glu Ala Leu Trp Leu Val Ser Ser Val
            260                 265                 270 cgc cag gcc gca ccg atc acg gcg ctc gac gac cgc gag tac ccg gtc      864
Arg Gln Ala Ala Pro Ile Thr Ala Leu Asp Asp Arg Glu Tyr Pro Val
        275                 280                 285 gac gcg gcg ctc acg gcc gac ctg aac gcg tac ctg ctc gcc cgc acc      912
Asp Ala Ala Leu Thr Ala Asp Leu Asn Ala Tyr Leu Leu Ala Arg Thr
    290                 295                 300 gac tga                                                              918
Asp
305
```

<210> SEQ ID NO 30
<211> LENGTH: 305
<212> TYPE: PRT
<213> ORGANISM: Curtobacterium pusillum

<400> SEQUENCE:

```
                         85                  90                  95
Val Leu Ala Gly Val Ala Asp Tyr Arg Ser Arg Asn Gly Asp Gly Gly
                100                 105                 110

Glu Leu Phe Ala Lys Leu Ile Leu Thr Arg Gly Ile Glu Gly Glu Gly
                115                 120                 125

Arg Pro Ser Gly Trp Val Phe Val Asp Glu Gly Glu Asp Phe Ser Gln
            130                 135                 140

Gln Arg Leu Gly Ile Arg Val Val Thr Leu Asp Arg Gly Tyr Arg His
145                 150                 155                 160

Asp Val Ala Glu Thr Ser Pro Trp Leu Leu Ala Gly Ala Lys Ser Leu
                165                 170                 175

Ser Tyr Ala Thr Asn Arg Ala Ala Gly Arg Glu Ala Ala Arg Arg Gly
                180                 185                 190

Ala Asp Asp Val Ile Phe Val Ser Ser Asp Gly Tyr Ala Leu Glu Gly
                195                 200                 205

Pro Thr Ser Asn Val Ile Val Leu Ala Asp Gly Val Val Arg Thr Pro
            210                 215                 220

Gln Thr Asp Gln Gly Ile Leu Ala Gly Thr Thr Gln Ala Ala Val Phe
225                 230                 235                 240

Asp Phe Phe Glu Glu Arg Gly Tyr Pro Thr Glu Tyr Arg Arg Ile Ser
                245                 250                 255

Ala Asp Glu Leu Arg Asp Ala Glu Ala Leu Trp Leu Val Ser Ser Val
                260                 265                 270

Arg Gln Ala Ala Pro Ile Thr Ala Leu Asp Asp Arg Glu Tyr Pro Val
            275                 280                 285

Asp Ala Ala Leu Thr Ala Asp Leu Asn Ala Tyr Leu Leu Ala Arg Thr
            290                 295                 300

Asp
305

<210> SEQ ID NO 31
<211> LENGTH: 918
<212> TYPE: DNA
<213> ORGANISM: Artificial
<220> FEATURE:
<223> OTHER INFORMATION: Codon-optimized sequence encoding SEQ ID NO 30

<400> SEQUENCE: 31
atgacccgtg caaccctgct gaccgttacc gcaccgaccc gtccggcaag cgcagatgaa     60
catggtgcag atcgtgcagc cggtgatgca ggttttgttc tggcagattt tggtgcaccg    120
caggttcgta ttaccgatct gggtattacc cgtggtgatg tgttttttga aaccattgca    180
gttattgatg tcatccgca ggcactggaa ctgcatctgg tcgtctggc acatagcgca     240 gcactgctgg atctgccgga accggatgca gcagtttggc gtgaagccgt gctggcaggc    300
gttgcagatt atcgtagccg taatggtgat ggcggtgaac tgtttgcaaa actgattctg    360
acccgtggta ttgaaggtga aggtcgtccg agcggttggg ttttttgtga tgaaggcgaa    420
gattttagcc agcagcgcct gggtattcgt gttgttaccc tggatcgtgg ttatcgtcat    480
gatgttgcag aaaccagccc gtggctgctg gctggtgcaa aaagcctgag ctatgcaacc    540
aatcgtgccg caggtcgtga agcagcacgt cgtggtgccg atgatgttat ttttgttagc    600
agtgatggtt atgcactgga aggtccgacc agcaatgtta ttgtgctggc cgatggtgtt    660
gttcgtacac cgcagaccga tcagggcatt ctggcaggca ccacccaggc agccgttttt    720 gattttttg aagaacgcgg ttatccgacc gaatatcgtc gtatttcagc cgatgaactg    780
```

```
cgtgatgccg aagcactgtg gctggttagc agcgttcgtc aggcagcacc gattacagca    840
ctggatgatc gtgaatatcc ggttgatgca gcactgaccg cagatctgaa tgcatatctg    900
ctggcacgta ccgattaa                                                   918

<210> SEQ ID NO 32
<211> LENGTH: 1131
<212> TYPE: DNA
<213> ORGANISM: Curtobacterium pusillum
<220> FEATURE:
<221> NAME/KEY: CDS
<222> LOCATION: (1)..(1131)

<400> SEQUENCE: 32 atg act tct acc agc atc tcc ctt acc agc ggc ccc acc gag acg agc        48
Met Thr Ser Thr Ser Ile Ser Leu Thr Ser Gly Pro Thr Glu Thr Ser
1               5                  10                  15 ggc ctg ctc tgg cag gtc acc cgc aac gag gcg gcg cgc gac gcc gcc        96
Gly Leu Leu Trp Gln Val Thr Arg Asn Glu Ala Ala Arg Asp Ala Ala
            20                  25                  30 gag cgc gag gag atc ctc gcc gat ccc ggt ttc ggc aac cac ttc acc       144
Glu Arg Glu Glu Ile Leu Ala Asp Pro Gly Phe Gly Asn His Phe Thr
        35                  40                  45 gac cac atg gtc gac atc tgc tgg tcg gcg aag gga ggc tgg cac cgg       192
Asp His Met Val Asp Ile Cys Trp Ser Ala Lys Gly Gly Trp His Arg
    50                  55                  60 ccg cgc gtc tcg ccg tac ggc ccg atc cag ctc gac ccg tcg gcc gcc       240
Pro Arg Val Ser Pro Tyr Gly Pro Ile Gln Leu Asp Pro Ser Ala Ala
65                  70                  75                  80 gtg ctg cac tac gcg cag gag atc ttc gag ggg ctg aag gcg tac cgc       288
Val Leu His Tyr Ala Gln Glu Ile Phe Glu Gly Leu Lys Ala Tyr Arg
                85                  90                  95 cac gag gac ggc tcg atc tgg aca ttc cgc ccg gag gcc aac gcc gcc       336
His Glu Asp Gly Ser Ile Trp Thr Phe Arg Pro Glu Ala Asn Ala Ala
            100                 105                 110 cgc atg cag cgc tcg gcc tat cgc ctg gcg ctg ccc gag ctc ccg gtc       384
Arg Met Gln Arg Ser Ala Tyr Arg Leu Ala Leu Pro Glu Leu Pro Val
        115                 120                 125 gag cac ttc ctc gac tcg ttg aag cag ctc gtc gcg gtg gac ggc gat       432
Glu His Phe Leu Asp Ser Leu Lys Gln Leu Val Ala Val Asp Gly Asp
    130                 135                 140 tgg gtg ccg acc gcg ccg gag acc agc ctc tac ctg cgt ccg ttc atg       480
Trp Val Pro Thr Ala Pro Glu Thr Ser Leu Tyr Leu Arg Pro Phe Met
145                 150                 155                 160 ttc gcc aag gag gcg ttc ctg ggc gtg cgc ccg gcg aac aag gtc gcg       528
Phe Ala Lys Glu Ala Phe Leu Gly Val Arg Pro Ala Asn Lys Val Ala
                165                 170                 175 tac tac ctg atc gcg agc ccg gcg ggc gcc tat ttc tcg ggc ggc gtc       576
Tyr Tyr Leu Ile Ala Ser Pro Ala Gly Ala Tyr Phe Ser Gly Gly Val
            180                 185                 190 gca ccc gtc tcg atc tgg ctg tcc gac cgc tgg tcg cgc gcc ggc cac       624
Ala Pro Val Ser Ile Trp Leu Ser Asp Arg Trp Ser Arg Ala Gly His
        195                 200                 205 ggt ggc acc ggg gcg gcg aag acc ggc ggc aac tac gcc tcc agc ctc       672
Gly Gly Thr Gly Ala Ala Lys Thr Gly Gly Asn Tyr Ala Ser Ser Leu
    210                 215                 220 ctg cct cag gcc gag gcg gcc gag cac ggc tgc gca cag gtg ctg ttc       720
Leu Pro Gln Ala Glu Ala Ala Glu His Gly Cys Ala Gln Val Leu Phe
225                 230                 235                 240 ctc gac tcg gtc gaa ggc cga tac ctc gag gag ctc ggc ggg atg aac       768
Leu Asp Ser Val Glu Gly Arg Tyr Leu Glu Glu Leu Gly Gly Met Asn
```

```
Leu Asp Ser Val Glu Gly Arg Tyr Leu Glu Leu Gly Gly Met Asn
                245                 250                 255 gtg gtc gtc tac aag gac ggc acg gtg gtg acc ccg gag tcc gac      816
Val Leu Val Tyr Lys Asp Gly Thr Val Val Thr Pro Glu Ser Asp
        260                 265                 270 agc atc ctg gag ggc atc acg ctg gac tcg atc ctg cag ctc gcg cgt  864
Ser Ile Leu Glu Gly Ile Thr Leu Asp Ser Ile Leu Gln Leu Ala Arg
            275                 280                 285 gat cgc ggc cac cgg gtc gag cgc cgc gtg acg atc gac gag tgg      912
Asp Arg Gly His Arg Val Glu Arg Arg Val Thr Ile Asp Glu Trp
    290                 295                 300 cgc gac ggc gtc gag agc ggc gac atc gtc gag gtg ttc gcc tgc ggc  960
Arg Asp Gly Val Glu Ser Gly Asp Ile Val Glu Val Phe Ala Cys Gly
305                 310                 315                 320 acg gcc gcg gtg atc acc ccg atc ggc gag ctc aag tcg gac acc ttc 1008
Thr Ala Ala Val Ile Thr Pro Ile Gly Glu Leu Lys Ser Asp Thr Phe
                325                 330                 335 acc gtc ggc gac atc acc gcg cct ccc ggt gag ctg acg atg gcg ctg 1056
Thr Val Gly Asp Ile Thr Ala Pro Pro Gly Glu Leu Thr Met Ala Leu
            340                 345                 350 cgc cag gag ctc acc gac atc cag tac ggc cgc gtc cac gac cgg cac 1104
Arg Gln Glu Leu Thr Asp Ile Gln Tyr Gly Arg Val His Asp Arg His
        355                 360                 365 aac tgg atg acg cgc ctc gac gcg tag                              1131
Asn Trp Met Thr Arg Leu Asp Ala
    370                 375

<210> SEQ ID NO 33
<211> LENGTH: 376
<212> TYPE: PRT
<213> ORGANISM: Curtobacterium pusillum

<400> SEQUENCE: 33

Met Thr Ser Thr Ser Ile Ser Leu Thr Ser Gly Pro Thr Glu Thr Ser
1               5                   10                  15

Gly Leu Leu Trp Gln Val Thr Arg Asn Glu Ala Ala Arg Asp Ala Ala
            20                  25                  30

Glu Arg Glu Glu Ile Leu Ala Asp Pro Gly Phe Gly Asn His Phe Thr
        35                  40                  45

Asp His Met Val Asp Ile Cys Trp Ser Ala Lys Gly Gly Trp His Arg
    50                  55                  60

Pro Arg Val Ser Pro Tyr Gly Pro Ile Gln Leu Asp Pro Ser Ala Ala
65                  70                  75                  80

Val Leu His Tyr Ala Gln Glu Ile Phe Glu Gly Leu Lys Ala Tyr Arg
                85                  90                  95

His Glu Asp Gly Ser Ile Trp Thr Phe Arg Pro Glu Ala Asn Ala Ala
            100                 105                 110

Arg Met Gln Arg Ser Ala Tyr Arg Leu Ala Leu Pro Glu Leu Pro Val
        115                 120                 125

Glu His Phe Leu Asp Ser Leu Lys Gln Leu Val Ala Val Asp Gly Asp
    130                 135                 140

Trp Val Pro Thr Ala Pro Glu Thr Ser Leu Tyr Leu Arg Pro Phe Met
145                 150                 155                 160

Phe Ala Lys Glu Ala Phe Leu Gly Val Arg Pro Ala Asn Lys Val Ala
                165                 170                 175

Tyr Tyr Leu Ile Ala Ser Pro Ala Gly Ala Tyr Phe Ser Gly Gly Val
            180                 185                 190
```

```
Ala Pro Val Ser Ile Trp Leu Ser Asp Arg Trp Ser Arg Ala Gly His
        195                 200                 205

Gly Gly Thr Gly Ala Ala Lys Thr Gly Gly Asn Tyr Ala Ser Ser Leu
    210                 215                 220

Leu Pro Gln Ala Glu Ala Ala Glu His Gly Cys Ala Gln Val Leu Phe
225                 230                 235                 240

Leu Asp Ser Val Glu Gly Arg Tyr Leu Glu Glu Leu Gly Gly Met Asn
                245                 250                 255

Val Val Leu Val Tyr Lys Asp Gly Thr Val Val Thr Pro Glu Ser Asp
            260                 265                 270

Ser Ile Leu Glu Gly Ile Thr Leu Asp Ser Ile Leu Gln Leu Ala Arg
        275                 280                 285

Asp Arg Gly His Arg Val Glu Arg Arg Val Thr Ile Asp Glu Trp
290                 295                 300

Arg Asp Gly Val Glu Ser Gly Asp Ile Val Glu Val Phe Ala Cys Gly
305                 310                 315                 320

Thr Ala Ala Val Ile Thr Pro Ile Gly Glu Leu Lys Ser Asp Thr Phe
                325                 330                 335

Thr Val Gly Asp Ile Thr Ala Pro Pro Gly Glu Leu Thr Met Ala Leu
            340                 345                 350

Arg Gln Glu Leu Thr Asp Ile Gln Tyr Gly Arg Val His Asp Arg His
        355                 360                 365

Asn Trp Met Thr Arg Leu Asp Ala
    370                 375

<210> SEQ ID NO 34
<211> LENGTH: 795
<212> TYPE: DNA
<213> ORGANISM: Curtobacterium pusillum
<220> FEATURE:
<221> NAME/KEY: CDS
<222> LOCATION: (1)..(795)

<400> SEQUENCE: 34 atg gac gcg agc agc acc ctc ttc gac tgg gcg ggc ggc gag ctc gtc      48
Met Asp Ala Ser Ser Thr Leu Phe Asp Trp Ala Gly Gly Glu Leu Val
1               5                   10                  15 gcc cgg gac tcc tgc gag gtc gcc gag acc gcg ctg ctc gtc gcg gac      96
Ala Arg Asp Ser Cys Glu Val Ala Glu Thr Ala Leu Leu Val Ala Asp
                20                  25                  30 tcc ttc ctc gtc gcc gac ggc acc gct ctc gcc ctc ggt ctg cac ggc     144
Ser Phe Leu Val Ala Asp Gly Thr Ala Leu Ala Leu Gly Leu His Gly
            35                  40                  45 tcc cgg ttc cag gac tcc gcg cgt ctg cag ggg cac ccc gac cga gcg     192
Ser Arg Phe Gln Asp Ser Ala Arg Leu Gln Gly His Pro Asp Arg Ala
        50                  55                  60 gag ctg cag cgg ttc tgg gag gcg ggc gtc gcc gcg ctg ccg cgc acc     240
Glu Leu Gln Arg Phe Trp Glu Ala Gly Val Ala Ala Leu Pro Arg Thr
65                  70                  75                  80 ggc gcc tgg ttc ccg cgg ttc gag ctg gtg cgc acc cgc gac gcg ctg     288
Gly Ala Trp Phe Pro Arg Phe Glu Leu Val Arg Thr Arg Asp Ala Leu
                85                  90                  95 cgg ttg cga ttc cgg ttg cgc acc gcg ccg gcg ttg acg agc gag ctg     336
Arg Leu Arg Phe Arg Leu Arg Thr Ala Pro Ala Leu Thr Ser Glu Leu
            100                 105                 110 gtc gtc gcc acg gcg gcc tcc gac ccg cga cgg gct ccc gac atc aaa     384
Val Val Ala Thr Ala Ala Ser Asp Pro Arg Arg Ala Pro Asp Ile Lys
        115                 120                 125
```

```
ggg ccc gac atc gac cgg ctg tcg gtg ctg cgc cag cgc gca cag gcg    432
Gly Pro Asp Ile Asp Arg Leu Ser Val Leu Arg Gln Arg Ala Gln Ala
130                 135                 140 gcc ggc gcc cag gag gcg atc ctg ctc gac gag gga ttc gtg gcc gac    480
Ala Gly Ala Gln Glu Ala Ile Leu Leu Asp Glu Gly Phe Val Ala Asp
145                 150                 155                 160 ggt gcg acc acc gcc ctg ctc tgg tgg cgc ggc gac acg ctc tac acg    528
Gly Ala Thr Thr Ala Leu Leu Trp Trp Arg Gly Asp Thr Leu Tyr Thr
                165                 170                 175 ccc ccg ctg tcc ctg ccc cgg gtg gac agc gtc gcc gcg cgc acc gtc    576
Pro Pro Leu Ser Leu Pro Arg Val Asp Ser Val Ala Ala Arg Thr Val
            180                 185                 190 cgc ggc atc gcc gcc gcc ctg cgg gtg ccg gtc gac gag gag gag gcg    624
Arg Gly Ile Ala Ala Ala Leu Arg Val Pro Val Asp Glu Glu Glu Ala
        195                 200                 205 cgc ccc gcg cag ctg gac ggc gtg acg ctc tgg gcc gtc aac gcc ctg    672
Arg Pro Ala Gln Leu Asp Gly Val Thr Leu Trp Ala Val Asn Ala Leu
210                 215                 220 cac ggc atc cgg gcc gtc acg gcc tgg gtg gac ggc ccc gga ctg tcg    720
His Gly Ile Arg Ala Val Thr Ala Trp Val Asp Gly Pro Gly Leu Ser
225                 230                 235                 240 cag gat ccg gca cgc acg gac gcg tgg cgc gcc cgc ttc gcg atg ctg    768
Gln Asp Pro Ala Arg Thr Asp Ala Trp Arg Ala Arg Phe Ala Met Leu
                245                 250                 255 tcg cgt ccg ctg ccg ctc gca gcc tga                                795
Ser Arg Pro Leu Pro Leu Ala Ala
            260

<210> SEQ ID NO 35
<211> LENGTH: 264
<212> TYPE: PRT
<213> ORGANISM: Curtobacterium pusillum

<400> SEQUENCE: 35

Met Asp Ala Ser Ser Thr Leu Phe Asp Trp Ala Gly Gly Glu Leu Val
1               5                   10                  15

Ala Arg Asp Ser Cys Glu Val Ala Glu Thr Ala Leu Leu Val Ala Asp
            20                  25                  30

Ser Phe Leu Val Ala Asp Gly Thr Ala Leu Ala Leu Gly Leu His Gly
        35                  40                  45

Ser Arg Phe Gln Asp Ser Ala Arg Leu Gln Gly His Pro Asp Arg Ala
    50                  55                  60

Glu Leu Gln Arg Phe Trp Glu Ala Gly Val Ala Ala Leu Pro Arg Thr
65                  70                  75                  80

Gly Ala Trp Phe Pro Arg Phe Glu Leu Val Arg Thr Arg Asp Ala Leu
                85                  90                  95

Arg Leu Arg Phe Arg Leu Arg Thr Ala Pro Ala Leu Thr Ser Glu Leu
            100                 105                 110

Val Val Ala Thr Ala Ala Ser Asp Pro Arg Arg Ala Pro Asp Ile Lys
        115                 120                 125

Gly Pro Asp Ile Asp Arg Leu Ser Val Leu Arg Gln Arg Ala Gln Ala
    130                 135                 140

Ala Gly Ala Gln Glu Ala Ile Leu Leu Asp Glu Gly Phe Val Ala Asp
145                 150                 155                 160

Gly Ala Thr Thr Ala Leu Leu Trp Trp Arg Gly Asp Thr Leu Tyr Thr
                165                 170                 175

Pro Pro Leu Ser Leu Pro Arg Val Asp Ser Val Ala Ala Arg Thr Val
            180                 185                 190
```

Arg Gly Ile Ala Ala Ala Leu Arg Val Pro Val Asp Glu Glu Ala
        195                 200                 205

Arg Pro Ala Gln Leu Asp Gly Val Thr Leu Trp Ala Val Asn Ala Leu
    210                 215                 220

His Gly Ile Arg Ala Val Thr Ala Trp Val Asp Gly Pro Gly Leu Ser
225                 230                 235                 240

Gln Asp Pro Ala Arg Thr Asp Ala Trp Arg Ala Arg Phe Ala Met Leu
                245                 250                 255

Ser Arg Pro Leu Pro Leu Ala Ala
            260

<210> SEQ ID NO 36
<211> LENGTH: 795
<212> TYPE: DNA
<213> ORGANISM: Artificial
<220> FEATURE:
<223> OTHER INFORMATION: Codon optimized sequence of SEQ ID NO 35

<400> SEQUENCE: 36
atggatgcaa gcagcaccct gtttgattgg gcaggcggtg aactggttgc acgtgatagc      60
tgtgaagttg cagaaaccgc actgctggtt cagatagct ttctggttgc cgatggcacc     120
gcactggcac tgggtctgca tggtagccgt tttcaggata gcacgtct gcagggtcat       180 ccggatcgtg cagaactgca gcgttttttgg gaagccggtg ttgcagcact gcctcgtacc   240
ggtgcatggt ttccgcgttt tgaactggtg cgtacccgtg atgcactgcg tctgcgtttt    300
cgtctgcgta cagcaccggc actgaccagc gaactggtgg ttgccaccgc agcaagcgat   360
ccgcgtcgtg caccggatat taaaggtccg gatattgatc gtctgagcgt tctgcgtcag    420
cgtgcacagg cagccggtgc acaagaggca attctgctgg atgaaggttt tgttgcagat    480
ggtgcaacca cagccctgct gtggtggcgt ggtgataccc tgtataccc tccgctgagc    540 ctgcctcgtg ttgatagcgt tgcagcccgt accgttcgtg gtattgcagc agccctgcgt    600
gttccggttg atgaagaaga agcacgtccg gcacagctgg atggtgtgac cctgtgggca   660
gttaatgcac tgcatggcat tcgtgcagtt accgcatggg ttgatggtcc gggtctgagc   720
caggatccgg cacgtaccga tgcctggcgt gcacgttttg caatgctgag ccgtccgctg   780
ccgctggcag cataa                                                      795

<210> SEQ ID NO 37
<211> LENGTH: 930
<212> TYPE: DNA
<213> ORGANISM: Rahnella aquatilis
<220> FEATURE:
<221> NAME/KEY: CDS
<222> LOCATION: (1)..(930)

<400> SEQUENCE: 37 atg acg aag aaa gct gat tac att tgg ttc aac ggc gag atg gtt cca       48
Met Thr Lys Lys Ala Asp Tyr Ile Trp Phe Asn Gly Glu Met Val Pro
1               5                   10                  15 tgg gca gaa gct aaa gtc cat gtc atg tca cac gca ctg cat tac ggc       96
Trp Ala Glu Ala Lys Val His Val Met Ser His Ala Leu His Tyr Gly
                20                  25                  30 act tcc gtt ttc gaa ggc gtg cgt tgc tac gac tcc cat aaa ggc cca      144
Thr Ser Val Phe Glu Gly Val Arg Cys Tyr Asp Ser His Lys Gly Pro
            35                  40                  45 gtc gta ttc cgt cac cgt gaa cat atg cag cgt ctg cgc gat tcc gca      192
Val Val Phe Arg His Arg Glu His Met Gln Arg Leu Arg Asp Ser Ala

```
            50                  55                  60
aaa att tac cgt atg cct gtt tcc cag agt gtg gat gag ctg atg gaa       240
Lys Ile Tyr Arg Met Pro Val Ser Gln Ser Val Asp Glu Leu Met Glu
 65                  70                  75                  80 gct tgc cgc gaa acc ctg cgt aaa aac aat ctg gtc agc gcg tat atc       288
Ala Cys Arg Glu Thr Leu Arg Lys Asn Asn Leu Val Ser Ala Tyr Ile
                 85                  90                  95 cgt ccg ctg gtg ttt gtc ggc gat gtg ggt atg ggc gtt aat ccg ccg       336
Arg Pro Leu Val Phe Val Gly Asp Val Gly Met Gly Val Asn Pro Pro
            100                 105                 110 gac ggc tac aaa act gat gtg atc atc gcc gcc ttc ccg tgg ggc gcg       384
Asp Gly Tyr Lys Thr Asp Val Ile Ile Ala Ala Phe Pro Trp Gly Ala
        115                 120                 125 tat ctg ggt gaa gaa gcg ctg gag cag ggt atc gac gcg atg gtg tct       432
Tyr Leu Gly Glu Glu Ala Leu Glu Gln Gly Ile Asp Ala Met Val Ser
    130                 135                 140 tca tgg aac cgc gtt gct gca aac acc att cca acc gct gcg aaa gcc       480
Ser Trp Asn Arg Val Ala Ala Asn Thr Ile Pro Thr Ala Ala Lys Ala
145                 150                 155                 160 ggt ggt aac tac ctg tcc tcc ctg ctg gtc ggc agc gaa gca cgt cgt       528
Gly Gly Asn Tyr Leu Ser Ser Leu Leu Val Gly Ser Glu Ala Arg Arg
                165                 170                 175 cac ggt tat cag gaa ggt atc gcg ctg gac att cac ggc tat gtg tct       576
His Gly Tyr Gln Glu Gly Ile Ala Leu Asp Ile His Gly Tyr Val Ser
            180                 185                 190 gaa ggc gct ggc gaa aac ctg ttt gaa gtg aaa gaa ggc att ctg ttc       624
Glu Gly Ala Gly Glu Asn Leu Phe Glu Val Lys Glu Gly Ile Leu Phe
        195                 200                 205 aca ccg cca ttt acc tct tct gcc ctg cca ggt atc acc cgt gac gct       672
Thr Pro Pro Phe Thr Ser Ser Ala Leu Pro Gly Ile Thr Arg Asp Ala
    210                 215                 220 att att aaa ctg gca aaa gac ctg ggt ctt gaa gtg cgt gag caa gtt       720
Ile Ile Lys Leu Ala Lys Asp Leu Gly Leu Glu Val Arg Glu Gln Val
225                 230                 235                 240 ctg tcc cgt gaa tcc ctg tat ctg gca gac gaa gtc ttc atg tcc ggt       768
Leu Ser Arg Glu Ser Leu Tyr Leu Ala Asp Glu Val Phe Met Ser Gly
                245                 250                 255 acc gct gca gaa atc acc ccg gtg cgc agc gtt gac ggc att cag gtc       816
Thr Ala Ala Glu Ile Thr Pro Val Arg Ser Val Asp Gly Ile Gln Val
            260                 265                 270 ggt atc ggt aaa cgt ggt ccg gtg acc aaa caa att cag gat gca ttc       864
Gly Ile Gly Lys Arg Gly Pro Val Thr Lys Gln Ile Gln Asp Ala Phe
        275                 280                 285 ttc ggc ctg ttc acc ggc aaa acc gaa gat aaa tgg ggt tgg ctg gat       912
Phe Gly Leu Phe Thr Gly Lys Thr Glu Asp Lys Trp Gly Trp Leu Asp
    290                 295                 300 cca atc aac cca caa taa                                               930
Pro Ile Asn Pro Gln
305

<210> SEQ ID NO 38
<211> LENGTH: 309
<212> TYPE: PRT
<213> ORGANISM: Rahnella aquatilis

<400> SEQUENCE: 38

Met Thr Lys Lys Ala Asp Tyr Ile Trp Phe Asn Gly Glu Met Val Pro
  1               5                  10                  15

Trp Ala Glu Ala Lys Val His Val Met Ser His Ala Leu His Tyr Gly
                 20                  25                  30
```

Thr Ser Val Phe Glu Gly Val Arg Cys Tyr Asp Ser His Lys Gly Pro
        35                  40                  45

Val Val Phe Arg His Arg Glu His Met Gln Arg Leu Arg Asp Ser Ala
    50                  55                  60

Lys Ile Tyr Arg Met Pro Val Ser Gln Ser Val Asp Glu Leu Met Glu
65                  70                  75                  80

Ala Cys Arg Glu Thr Leu Arg Lys Asn Asn Leu Val Ser Ala Tyr Ile
                85                  90                  95

Arg Pro Leu Val Phe Val Gly Asp Val Gly Met Gly Val Asn Pro Pro
            100                 105                 110

Asp Gly Tyr Lys Thr Asp Val Ile Ile Ala Ala Phe Pro Trp Gly Ala
        115                 120                 125

Tyr Leu Gly Glu Glu Ala Leu Glu Gln Gly Ile Asp Ala Met Val Ser
    130                 135                 140

Ser Trp Asn Arg Val Ala Ala Asn Thr Ile Pro Thr Ala Ala Lys Ala
145                 150                 155                 160

Gly Gly Asn Tyr Leu Ser Ser Leu Leu Val Gly Ser Glu Ala Arg Arg
                165                 170                 175

His Gly Tyr Gln Glu Gly Ile Ala Leu Asp Ile His Gly Tyr Val Ser
            180                 185                 190

Glu Gly Ala Gly Glu Asn Leu Phe Glu Val Lys Glu Gly Ile Leu Phe
        195                 200                 205

Thr Pro Pro Phe Thr Ser Ser Ala Leu Pro Gly Ile Thr Arg Asp Ala
    210                 215                 220

Ile Ile Lys Leu Ala Lys Asp Leu Gly Leu Glu Val Arg Glu Gln Val
225                 230                 235                 240

Leu Ser Arg Glu Ser Leu Tyr Leu Ala Asp Glu Val Phe Met Ser Gly
                245                 250                 255

Thr Ala Ala Glu Ile Thr Pro Val Arg Ser Val Asp Gly Ile Gln Val
            260                 265                 270

Gly Ile Gly Lys Arg Gly Pro Val Thr Lys Gln Ile Gln Asp Ala Phe
        275                 280                 285

Phe Gly Leu Phe Thr Gly Lys Thr Glu Asp Lys Trp Gly Trp Leu Asp
    290                 295                 300

Pro Ile Asn Pro Gln
305

<210> SEQ ID NO 39
<211> LENGTH: 930
<212> TYPE: DNA
<213> ORGANISM: Artificial
<220> FEATURE:
<223> OTHER INFORMATION: Codon-optimized sequence coding for SEQ ID NO
      38

<400> SEQUENCE: 39
atgaccaaaa aagccgacta catttggttt aatggtgaaa tggttccgtg ggctgaagca        60
aaagttcatg ttatgagcca tgcactgcat tatggcacca gcgttttga aggtgttcgt       120 tgttatgata gccataaagg tccggttgtt tttcgtcatc gtgaacacat gcagcgtctg       180
cgtgatagcg caaaaatcta tcgtatgccg gttagccaga gcgttgatga actgatggaa       240
gcatgtcgtg aaaccctgcg taaaaacaat ctggttagcg catatattcg tccgctggtt       300
tttgttggtg atgttggtat gggtgttaat ccgcctgatg gttataaaac cgatgttatt       360
attgcagcat ttccgtgggg tgcatatctg ggtgaagaag cactggaaca gggtattgat       420

-continued

```
gcaatggtta gcagctggaa tcgtgttgca gcaaatacca ttccgaccgc agcaaaagcc      480
ggtggtaatt atctgagcag cctgctggtt ggtagcgaag cacgtcgtca tggttatcaa      540
gaaggtattg cactggatat tcatggctat gttagcgaag gtgccggtga aaacctgttt      600
gaagttaaag aaggcattct gtttacccca ccgtttaccg cagcgcact gcctggtatt       660 acccgtgatg caattatcaa actggcaaaa gatctgggtc tggaagttcg tgaacaggtt      720
ctgagccgtg aaagcctgta tctggcagat gaagttttta tgagcggcac cgcagcagaa      780
attacaccgg ttcgtagcgt ggatggtatt caggttggta ttggtaaacg tggtccggtt      840
accaaacaaa ttcaggatgc attttttggc ctgtttaccg caaaaccga agataaatgg       900 ggttggctgg atccgattaa tccgcagtaa                                      930

<210> SEQ ID NO 40
<211> LENGTH: 798
<212> TYPE: DNA
<213> ORGANISM: Rahnella aquatilis
<220> FEATURE:
<221> NAME/KEY: CDS
<222> LOCATION: (1)..(798)

<400> SEQUENCE: 40 atg tgg att aat ggt gtg gcg gcc gcg atg ttg tcg gca agt gac cgt        48
Met Trp Ile Asn Gly Val Ala Ala Ala Met Leu Ser Ala Ser Asp Arg
1               5                   10                  15 tca gtg cag ttt ggc gac ggt tgc ttt acc aca gcc agg gtg tca gac        96
Ser Val Gln Phe Gly Asp Gly Cys Phe Thr Thr Ala Arg Val Ser Asp
                20                  25                  30 ggt gtg att gtg ttt ctg gcc ggg cat att cag cgt ctg caa cgt gct       144
Gly Val Ile Val Phe Leu Ala Gly His Ile Gln Arg Leu Gln Arg Ala
            35                  40                  45 gcg tcg gta ctg cgg att gaa ggt gtg gac tgg acg gct ctg gaa cag       192
Ala Ser Val Leu Arg Ile Glu Gly Val Asp Trp Thr Ala Leu Glu Gln
        50                  55                  60 gaa atg gtt ctg gct gcc gga cag cag aaa gag gca gtg gtt aaa gcc       240
Glu Met Val Leu Ala Ala Gly Gln Gln Lys Glu Ala Val Val Lys Ala
65                  70                  75                  80 gtc gtg acg cgc ggg cag ggc ggc cga ggt tac agc gcc gca ggt tgc       288
Val Val Thr Arg Gly Gln Gly Gly Arg Gly Tyr Ser Ala Ala Gly Cys
                85                  90                  95 tct gcg ccg acg cgt att gtt tct gcg tct gat tat ccg gtg cat tat       336
Ser Ala Pro Thr Arg Ile Val Ser Ala Ser Asp Tyr Pro Val His Tyr
                100                 105                 110 cac gcg tgg cgg caa cag ggc gtg aaa ctc gcg ctg agc ccg gtc aca       384
His Ala Trp Arg Gln Gln Gly Val Lys Leu Ala Leu Ser Pro Val Thr
            115                 120                 125 ctg agt aag aac ccg ttg ctg gcc gga ata aaa cat ctt aac cgg ctg       432
Leu Ser Lys Asn Pro Leu Leu Ala Gly Ile Lys His Leu Asn Arg Leu
        130                 135                 140 gaa cag gta atg atc cgc atg cat ctt gac cag aca gat gcc aat gaa       480
Glu Gln Val Met Ile Arg Met His Leu Asp Gln Thr Asp Ala Asn Glu
145                 150                 155                 160 gcg ctg gtg gtt gac acc tcg ggc tgc ctg gtg gaa tgc tgt gcg gca       528
Ala Leu Val Val Asp Thr Ser Gly Cys Leu Val Glu Cys Cys Ala Ala
                165                 170                 175 aat tta ttc tgg cgt aag gga aat cag gtg ttt act ccg gat tta tcg       576
Asn Leu Phe Trp Arg Lys Gly Asn Gln Val Phe Thr Pro Asp Leu Ser
                180                 185                 190 cag tcc ggc gtt gat ggt ctt atg cgt cag cac gtc atc cgc gta ctt       624
Gln Ser Gly Val Asp Gly Leu Met Arg Gln His Val Ile Arg Val Leu
```

```
Gln Ser Gly Val Asp Gly Leu Met Arg Gln His Val Ile Arg Val Leu
            195                 200                 205 gaa gcg aca tcc ccc tgg gtt gtg aac atc gtc agt gaa tct gcg gaa      672
Glu Ala Thr Ser Pro Trp Val Val Asn Ile Val Ser Glu Ser Ala Glu
210                 215                 220 aca tta tca gat gct gac gaa atc ctg att tgt aac gcc ctg atg ccc      720
Thr Leu Ser Asp Ala Asp Glu Ile Leu Ile Cys Asn Ala Leu Met Pro
225                 230                 235                 240 gtt ctg ccg gtg aat cag gtc gat gac aaa tat tac att tca cgg cgt      768
Val Leu Pro Val Asn Gln Val Asp Asp Lys Tyr Tyr Ile Ser Arg Arg
                245                 250                 255 ttg tgc gat ttc ctg ctc cag agc tgt taa                              798
Leu Cys Asp Phe Leu Leu Gln Ser Cys
            260                 265

<210> SEQ ID NO 41
<211> LENGTH: 265
<212> TYPE: PRT
<213> ORGANISM: Rahnella aquatilis

<400> SEQUENCE: 41

Met Trp Ile Asn Gly Val Ala Ala Met Leu Ser Ala Ser Asp Arg
1               5                   10                  15

Ser Val Gln Phe Gly Asp Gly Cys Phe Thr Thr Ala Arg Val Ser Asp
                20                  25                  30

Gly Val Ile Val Phe Leu Ala Gly His Ile Gln Arg Leu Gln Arg Ala
            35                  40                  45

Ala Ser Val Leu Arg Ile Glu Gly Val Asp Trp Thr Ala Leu Glu Gln
50                  55                  60

Glu Met Val Leu Ala Ala Gly Gln Gln Lys Glu Ala Val Val Lys Ala
65                  70                  75                  80

Val Val Thr Arg Gly Gln Gly Arg Gly Tyr Ser Ala Ala Gly Cys
                85                  90                  95

Ser Ala Pro Thr Arg Ile Val Ser Ala Ser Asp Tyr Pro Val His Tyr
            100                 105                 110

His Ala Trp Arg Gln Gln Gly Val Lys Leu Ala Leu Ser Pro Val Thr
        115                 120                 125

Leu Ser Lys Asn Pro Leu Leu Ala Gly Ile Lys His Leu Asn Arg Leu
130                 135                 140

Glu Gln Val Met Ile Arg Met His Leu Asp Gln Thr Asp Ala Asn Glu
145                 150                 155                 160

Ala Leu Val Val Asp Thr Ser Gly Cys Leu Val Glu Cys Cys Ala Ala
                165                 170                 175

Asn Leu Phe Trp Arg Lys Gly Asn Gln Val Phe Thr Pro Asp Leu Ser
            180                 185                 190

Gln Ser Gly Val Asp Gly Leu Met Arg Gln His Val Ile Arg Val Leu
        195                 200                 205

Glu Ala Thr Ser Pro Trp Val Val Asn Ile Val Ser Glu Ser Ala Glu
210                 215                 220

Thr Leu Ser Asp Ala Asp Glu Ile Leu Ile Cys Asn Ala Leu Met Pro
225                 230                 235                 240

Val Leu Pro Val Asn Gln Val Asp Asp Lys Tyr Tyr Ile Ser Arg Arg
                245                 250                 255

Leu Cys Asp Phe Leu Leu Gln Ser Cys
            260                 265
```

```
<210> SEQ ID NO 42
<211> LENGTH: 867
<212> TYPE: DNA
<213> ORGANISM: Achromobacter spanius
<220> FEATURE:
<221> NAME/KEY: CDS
<222> LOCATION: (1)..(867)

<400> SEQUENCE: 42 atg att ccg ggc gtg ccg ggc gaa agc cag gtg tat ctc aac ggc gag      48
Met Ile Pro Gly Val Pro Gly Glu Ser Gln Val Tyr Leu Asn Gly Glu
1               5                   10                  15 ttc ctg cgt gtc gac gag gcg aaa gtc tcc gtc ctg gac cgc ggt ttt      96
Phe Leu Arg Val Asp Glu Ala Lys Val Ser Val Leu Asp Arg Gly Phe
            20                  25                  30 att ttt ggc gac ggc atc tac gaa gtc gtt ccc gtg tac cag ggc aag     144
Ile Phe Gly Asp Gly Ile Tyr Glu Val Val Pro Val Tyr Gln Gly Lys
        35                  40                  45 gca ttc cgc atg gcg gag cac ctt aac cgc ctg gac cgc agc ctg gcc     192
Ala Phe Arg Met Ala Glu His Leu Asn Arg Leu Asp Arg Ser Leu Ala
    50                  55                  60 gcc ttg cgc atc acg ccg ccg atg gat cgc gcg ggc tgg gtc gac ctg     240
Ala Leu Arg Ile Thr Pro Pro Met Asp Arg Ala Gly Trp Val Asp Leu
65                  70                  75                  80 atc gaa cag ttg ctg gcg cgc acc acg ctg gac acc tgc atc gtg tac     288
Ile Glu Gln Leu Leu Ala Arg Thr Thr Leu Asp Thr Cys Ile Val Tyr
                85                  90                  95 ttg cag gtc acg cgc ggc gtt gcc aag cgc gac cac cag ttc ccg gcc     336
Leu Gln Val Thr Arg Gly Val Ala Lys Arg Asp His Gln Phe Pro Ala
            100                 105                 110 acg ccg gtt acg ccc acc gtg ttc ggc atg att tcg gcg tgg tcc cct     384
Thr Pro Val Thr Pro Thr Val Phe Gly Met Ile Ser Ala Trp Ser Pro
        115                 120                 125 ccg ccc gcc gcg caa cgc acg cag ggc ttg acc gcc atc agc att ccc     432
Pro Pro Ala Ala Gln Arg Thr Gln Gly Leu Thr Ala Ile Ser Ile Pro
    130                 135                 140 gac gaa cgc tgg ctg cat tgc gag atc aag tcg gtg tcg ctg ttg ggt     480
Asp Glu Arg Trp Leu His Cys Glu Ile Lys Ser Val Ser Leu Leu Gly
145                 150                 155                 160 aac gtg ctg gcc aag cag cag gcg gtg gat gcg aac gcc gac gaa gtc     528
Asn Val Leu Ala Lys Gln Gln Ala Val Asp Ala Asn Ala Asp Glu Val
                165                 170                 175 gtg cag ttt cgc gat ggc tat ctg acc gaa ggc tcg tcc acc aac atc     576
Val Gln Phe Arg Asp Gly Tyr Leu Thr Glu Gly Ser Ser Thr Asn Ile
            180                 185                 190 tgg gtg gtg tct ggc ggc aag ttg ttg gcg ccg ccc aag aac aac ctg     624
Trp Val Val Ser Gly Gly Lys Leu Leu Ala Pro Pro Lys Asn Asn Leu
        195                 200                 205 atc ctg gaa ggc atc cgc tac ggt ctg atg ggc gag ctg gcc gaa gca     672
Ile Leu Glu Gly Ile Arg Tyr Gly Leu Met Gly Glu Leu Ala Glu Ala
    210                 215                 220 gcg ggc atc cca ttc gag tcg cgc cgc atc acc cag caa gag gtg gaa     720
Ala Gly Ile Pro Phe Glu Ser Arg Arg Ile Thr Gln Gln Glu Val Glu
225                 230                 235                 240 tcc gcc gac gaa ttg atg ctg tct tcc gcc acc aag gaa gtg ctg gcg     768
Ser Ala Asp Glu Leu Met Leu Ser Ser Ala Thr Lys Glu Val Leu Ala
                245                 250                 255 att gtt tcc ttg gac gga aag ccg gtg ggt tcg ggc aag ccc ggc cct     816
Ile Val Ser Leu Asp Gly Lys Pro Val Gly Ser Gly Lys Pro Gly Pro
            260                 265                 270 gtt ttt gag cag ttg cga gcg ggt tat gat gcc cgc atc gcc gcg ctg     864
Val Phe Glu Gln Leu Arg Ala Gly Tyr Asp Ala Arg Ile Ala Ala Leu
```

```
Val Phe Glu Gln Leu Arg Ala Gly Tyr Asp Ala Arg Ile Ala Ala Leu
            275                 280                 285 taa                                                                  867

<210> SEQ ID NO 43
<211> LENGTH: 288
<212> TYPE: PRT
<213> ORGANISM: Achromobacter spanius

<400> SEQUENCE: 43

Met Ile Pro Gly Val Pro Gly Glu Ser Gln Val Tyr Leu Asn Gly Glu
1               5                   10                  15

Phe Leu Arg Val Asp Glu Ala Lys Val Ser Val Leu Asp Arg Gly Phe
            20                  25                  30

Ile Phe Gly Asp Gly Ile Tyr Glu Val Val Pro Val Tyr Gln Gly Lys
        35                  40                  45

Ala Phe Arg Met Ala Glu His Leu Asn Arg Leu Asp Arg Ser Leu Ala
    50                  55                  60

Ala Leu Arg Ile Thr Pro Pro Met Asp Arg Ala Gly Trp Val Asp Leu
65                  70                  75                  80

Ile Glu Gln Leu Leu Ala Arg Thr Thr Leu Asp Thr Cys Ile Val Tyr
                85                  90                  95

Leu Gln Val Thr Arg Gly Val Ala Lys Arg Asp His Gln Phe Pro Ala
            100                 105                 110

Thr Pro Val Thr Pro Thr Val Phe Gly Met Ile Ser Ala Trp Ser Pro
        115                 120                 125

Pro Pro Ala Ala Gln Arg Thr Gln Gly Leu Thr Ala Ile Ser Ile Pro
    130                 135                 140

Asp Glu Arg Trp Leu His Cys Glu Ile Lys Ser Val Ser Leu Leu Gly
145                 150                 155                 160

Asn Val Leu Ala Lys Gln Gln Ala Val Asp Ala Asn Ala Asp Glu Val
                165                 170                 175

Val Gln Phe Arg Asp Gly Tyr Leu Thr Glu Gly Ser Ser Thr Asn Ile
            180                 185                 190

Trp Val Val Ser Gly Gly Lys Leu Leu Ala Pro Pro Lys Asn Asn Leu
        195                 200                 205

Ile Leu Glu Gly Ile Arg Tyr Gly Leu Met Gly Glu Leu Ala Glu Ala
    210                 215                 220

Ala Gly Ile Pro Phe Glu Ser Arg Arg Ile Thr Gln Gln Glu Val Glu
225                 230                 235                 240

Ser Ala Asp Glu Leu Met Leu Ser Ser Ala Thr Lys Glu Val Leu Ala
                245                 250                 255

Ile Val Ser Leu Asp Gly Lys Pro Val Gly Ser Gly Lys Pro Gly Pro
            260                 265                 270

Val Phe Glu Gln Leu Arg Ala Gly Tyr Asp Ala Arg Ile Ala Ala Leu
        275                 280                 285

<210> SEQ ID NO 44
<211> LENGTH: 867
<212> TYPE: DNA
<213> ORGANISM: Artificial
<220> FEATURE:
<223> OTHER INFORMATION: Codon-optimized sequence coding for SEQ ID NO
      43

<400> SEQUENCE: 44
atgattccgg gtgttccagg tgaaagccag gtttatctga atggtgaatt tctgcgtgtt    60
```

```
gatgaagcaa aagttagcgt tctggatcgc ggttttatct ttggtgatgg tatttatgaa      120
gtggtgccgg tttatcaggg taaagcattt cgtatggcag aacatctgaa tcgtctggat      180
cgtagcctgg cagcactgcg tattaccccct ccgatggatc gtgcaggttg ggttgatctg     240
attgaacagc tgctggcacg taccaccctg gatacctgta ttgtttatct gcaggttacc      300
cgtggtgttg caaaacgtga tcatcagttt ccggcaacac cggttacccc gaccgttttt     360
ggcatgatta gcgcatggtc accgcctccg gcagcccagc gtacccaggg tctgaccgca      420
attagcattc cggatgaacg ttggctgcat tgtgaaatca aaagcgttag cctgctgggt      480
aatgttctgg caaaacagca ggcagttgat gcaaatgcag atgaagttgt tcagtttcgt     540
gatggttatc tgaccgaagg tagcagcacc aatattttggg ttgttagcgg tggtaaactg    600
ctggctccgc ctaaaaacaa tctgattctg gaaggtattc gctatggtct gatgggtgaa    660
ctggcagaag cagcaggtat tccgtttgaa agccgtcgta ttacacagca agaggttgaa     720
agcgcagata aactgatgct gagcagcgca accaaagaag ttctggccat tgttagcctg     780
gatggtaaac cggttggtag cggcaaaccg ggtccggttt ttgagcagct gcgtgccggt    840
tatgatgcac gtattgcagc actgtaa                                         867

<210> SEQ ID NO 45
<211> LENGTH: 885
<212> TYPE: DNA
<213> ORGANISM: Microbacterium ginsengisoli
<220> FEATURE:
<221> NAME/KEY: CDS
<222> LOCATION: (1)..(885)

<400> SEQUENCE: 45 atg acc tgg cgt ttc gcg ctc atc atc gag ccc gtg gca tcc gat gac      48
Met Thr Trp Arg Phe Ala Leu Ile Ile Glu Pro Val Ala Ser Asp Asp
1               5                   10                  15 ccc cgc acc gac ttc gac acg acc ttc gcg ccc gtc gac gcc tcg gcc      96
Pro Arg Thr Asp Phe Asp Thr Thr Phe Ala Pro Val Asp Ala Ser Ala
            20                  25                  30 ccc gcc ctc agc atc ggc gag ctc agc acc cag cgc gga gac gga atc     144
Pro Ala Leu Ser Ile Gly Glu Leu Ser Thr Gln Arg Gly Asp Gly Ile
        35                  40                  45 ttc gag tcg atc ggt gtc gtc gac agg cac ccg cag gag gtc gag gcg     192
Phe Glu Ser Ile Gly Val Val Asp Arg His Pro Gln Glu Val Glu Ala
    50                  55                  60 cac ctg gcg cgg ctc gcg cac tcc gcc gag atc tgc gac ctt ccg gtg     240
His Leu Ala Arg Leu Ala His Ser Ala Glu Ile Cys Asp Leu Pro Val
65                  70                  75                  80 ccg aac ctc gcc cag tgg cgc gcc gcc gtc gcc cgc gcg gcg gcg cag     288
Pro Asn Leu Ala Gln Trp Arg Ala Ala Val Ala Arg Ala Ala Ala Gln
                85                  90                  95 tgc ccg gag ggc gag gcg gtc atc aag ctc atc ctg agt cgc ggc atc     336
Cys Pro Glu Gly Glu Ala Val Ile Lys Leu Ile Leu Ser Arg Gly Ile
            100                 105                 110 gag cac ggt ccg acc ccg acc gcg tgg gtg acc gcg tcg gcc gcg ccc     384
Glu His Gly Pro Thr Pro Thr Ala Trp Val Thr Ala Ser Ala Ala Pro
        115                 120                 125 aac tat gcc cgc ccg cgc gcc gaa ggc atc tcc gtc gtc gtg ctc gat     432
Asn Tyr Ala Arg Pro Arg Ala Glu Gly Ile Ser Val Val Val Leu Asp
    130                 135                 140 cgc ggg ctc gac ctc gcc gca ccc gcc cgc gcc ccc tgg ctg ctg ctc     480
Arg Gly Leu Asp Leu Ala Ala Pro Ala Arg Ala Pro Trp Leu Leu Leu
145                 150                 155                 160
```

```
ggt gcg aag acg ttg tcg tat gcg acc aac atg gcg gcg ctg cgc gag    528
Gly Ala Lys Thr Leu Ser Tyr Ala Thr Asn Met Ala Ala Leu Arg Glu
            165                 170                 175 gcg cac cga cgc ggc gcg gat gac gcc gtc ttc gcc acg tcc gat gga    576
Ala His Arg Arg Gly Ala Asp Asp Ala Val Phe Ala Thr Ser Asp Gly
        180                 185                 190 ttc ctg ctc gag gcg ccg acc gcg tcg ctc gtg ctg cgc cgc ggc gat    624
Phe Leu Leu Glu Ala Pro Thr Ala Ser Leu Val Leu Arg Arg Gly Asp
    195                 200                 205 gtg ttc gtg acc ccc gag ccc gcc gcc ggc atc ctg cac ggc acc act    672
Val Phe Val Thr Pro Glu Pro Ala Ala Gly Ile Leu His Gly Thr Thr
210                 215                 220 cag ctg agc ctg ttc gcc cac ctc gcc gag cgg ggg ttc acg acc gcc    720
Gln Leu Ser Leu Phe Ala His Leu Ala Glu Arg Gly Phe Thr Thr Ala
225                 230                 235                 240 tac gag acc ctt ccg acg gcg gcc ctc gcc gac gcg gat gcc gcg tgg    768
Tyr Glu Thr Leu Pro Thr Ala Ala Leu Ala Asp Ala Asp Ala Ala Trp
            245                 250                 255 ctc gtc tcg agc gtc cgc ctc gcg gcc ccg atc acg gcc gtc gac ggc    816
Leu Val Ser Ser Val Arg Leu Ala Ala Pro Ile Thr Ala Val Asp Gly
        260                 265                 270 cgg gct ctc ccg cat gat gcg gcc ttc acg gcc gag ctg aac gcc tac    864
Arg Ala Leu Pro His Asp Ala Ala Phe Thr Ala Glu Leu Asn Ala Tyr
    275                 280                 285 ctg ctc tcg ccg cgc gac tga                                        885
Leu Leu Ser Pro Arg Asp
290
```

<210> SEQ ID NO 46
<211> LENGTH: 294
<212> TYPE: PRT
<213> ORGANISM: Microbacterium ginsengisoli

<400> SEQUENCE: 46

```
Met Thr Trp Arg Phe Ala Leu Ile Ile Glu Pro Val Ala Ser Asp Asp
1               5                   10                  15

Pro Arg Thr Asp Phe Asp Thr Thr Phe Ala Pro Val Asp Ala Ser Ala
            20                  25                  30

Pro Ala Leu Ser Ile Gly Glu Leu Ser Thr Gln Arg Gly Asp Gly Ile
        35                  40                  45

Phe Glu Ser Ile Gly Val Val Asp Arg His Pro Gln Glu Val Glu Ala
    50                  55                  60

His Leu Ala Arg Leu Ala His Ser Ala Glu Ile Cys Asp Leu Pro Val
65                  70                  75                  80

Pro Asn Leu Ala Gln Trp Arg Ala Ala Val Ala Arg Ala Ala Gln
            85                  90                  95

Cys Pro Glu Gly Glu Ala Val Ile Lys Leu Ile Leu Ser Arg Gly Ile
            100                 105                 110

Glu His Gly Pro Thr Pro Thr Ala Trp Val Thr Ala Ser Ala Ala Pro
        115                 120                 125

Asn Tyr Ala Arg Pro Arg Ala Glu Gly Ile Ser Val Val Leu Asp
    130                 135                 140

Arg Gly Leu Asp Leu Ala Ala Pro Ala Arg Ala Pro Trp Leu Leu Leu
145                 150                 155                 160

Gly Ala Lys Thr Leu Ser Tyr Ala Thr Asn Met Ala Ala Leu Arg Glu
            165                 170                 175

Ala His Arg Arg Gly Ala Asp Asp Ala Val Phe Ala Thr Ser Asp Gly
        180                 185                 190
```

| | | | | | | | | | | | | | | |
|---|---|---|---|---|---|---|---|---|---|---|---|---|---|---|
| Phe | Leu | Leu 195 | Glu | Ala | Pro | Thr | Ala 200 | Ser | Leu | Val | Leu 205 | Arg | Gly | Asp |
| Val | Phe 210 | Val | Thr | Pro | Glu | Pro 215 | Ala | Ala | Gly | Ile | Leu 220 | His | Gly | Thr | Thr |
| Gln 225 | Leu | Ser | Leu | Phe | Ala 230 | His | Leu | Ala | Glu | Arg 235 | Gly | Phe | Thr | Thr | Ala 240 |
| Tyr | Glu | Thr | Leu | Pro 245 | Thr | Ala | Ala | Leu | Ala 250 | Asp | Ala | Asp | Ala 255 | Ala | Trp |
| Leu | Val | Ser | Ser 260 | Val | Arg | Leu | Ala | Ala 265 | Pro | Ile | Thr | Ala | Val 270 | Asp | Gly |
| Arg | Ala | Leu 275 | Pro | His | Asp | Ala | Ala 280 | Phe | Thr | Ala | Glu | Leu 285 | Asn | Ala | Tyr |
| Leu | Leu | Ser 290 | Pro | Arg | Asp |